(12) United States Patent
Wu

(10) Patent No.: US 10,519,251 B2
(45) Date of Patent: *Dec. 31, 2019

(54) FABS-IN-TANDEM IMMUNOGLOBULIN AND USES THEREOF

(71) Applicant: EPIMAB BIOTHERAPEUTICS, Pinghu, Zhejiang (CN)

(72) Inventor: Chengbin Wu, Shanghai (CN)

(73) Assignee: EpimAb Biotherapeutics, Inc., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/732,088

(22) PCT Filed: Dec. 24, 2014

(86) PCT No.: PCT/US2014/072336
§ 371 (c)(1),
(2) Date: Jun. 5, 2015

(87) PCT Pub. No.: WO2015/103072
PCT Pub. Date: Jul. 9, 2015

(65) Prior Publication Data
US 2016/0289341 A1    Oct. 6, 2016

(30) Foreign Application Priority Data

Dec. 30, 2013  (WO) ............... PCT/CN2013/090923

(51) Int. Cl.
| | | |
|---|---|---|
| *C07K 16/46* | (2006.01) | |
| *A61K 39/00* | (2006.01) | |
| *A61K 39/395* | (2006.01) | |
| *C07K 16/00* | (2006.01) | |
| *C07K 16/28* | (2006.01) | |
| *C07K 16/24* | (2006.01) | |
| *A61K 45/06* | (2006.01) | |

(52) U.S. Cl.
CPC ........ *C07K 16/468* (2013.01); *A61K 39/3955* (2013.01); *A61K 39/39558* (2013.01); *A61K 45/06* (2013.01); *C07K 16/241* (2013.01); *C07K 16/244* (2013.01); *C07K 16/2803* (2013.01); *C07K 16/2809* (2013.01); *C07K 16/2818* (2013.01); *C07K 16/2887* (2013.01); *A61K 2039/505* (2013.01); *C07K 2317/21* (2013.01); *C07K 2317/31* (2013.01); *C07K 2317/35* (2013.01); *C07K 2317/52* (2013.01); *C07K 2317/522* (2013.01); *C07K 2317/55* (2013.01); *C07K 2317/56* (2013.01); *C07K 2317/64* (2013.01); *C07K 2317/66* (2013.01); *C07K 2317/76* (2013.01); *C07K 2317/90* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,006,309 A | 4/1991 | Khalil et al. |
| 5,063,081 A | 11/1991 | Cozzette et al. |
| 5,089,424 A | 2/1992 | Khalil et al. |
| 5,294,404 A | 3/1994 | Grandone et al. |
| 7,419,821 B2 | 9/2008 | Davis et al. |
| 7,682,833 B2 | 3/2010 | Miller et al. |
| 7,838,638 B2 | 11/2010 | Allan et al. |
| 8,722,859 B2 | 5/2014 | Miller |
| 2002/0004587 A1* | 1/2002 | Miller .................... C07K 16/00 530/388.8 |
| 2004/0018577 A1 | 1/2004 | Emerson Campbell et al. |
| 2005/0042664 A1 | 2/2005 | Wu et al. |
| 2005/0074821 A1 | 4/2005 | Wild et al. |
| 2005/0250185 A1 | 11/2005 | Murphy et al. |
| 2006/0160164 A1 | 7/2006 | Miller et al. |
| 2006/0206947 A1 | 9/2006 | Scallon et al. |
| 2006/0235208 A1 | 10/2006 | Lazar et al. |
| 2007/0071675 A1 | 3/2007 | Wu et al. |
| 2008/0269467 A1 | 10/2008 | Allen et al. |
| 2009/0155275 A1* | 6/2009 | Wu ...................... C07K 16/468 424/136.1 |
| 2009/0162360 A1* | 6/2009 | Klein .................... C07K 16/22 424/136.1 |
| 2009/0311253 A1 | 12/2009 | Ghayur et al. |
| 2010/0260668 A1 | 10/2010 | Ghayur et al. |
| 2012/0301400 A1 | 11/2012 | Williams et al. |
| 2013/0058937 A1 | 3/2013 | Auer et al. |
| 2013/0066054 A1 | 3/2013 | Humphreys et al. |
| 2013/0078249 A1* | 3/2013 | Ast ...................... C07K 16/468 424/136.1 |
| 2014/0194599 A1 | 7/2014 | Pass et al. |
| 2016/0289343 A1* | 10/2016 | Wu ...................... C07K 16/241 |

FOREIGN PATENT DOCUMENTS

| | | |
|---|---|---|
| EP | 2443154 | 12/2013 |
| JP | 2003-531588 A | 10/2003 |
| JP | 2010-535032 A | 11/2010 |
| JP | 2012-530088 A | 11/2012 |
| RU | 2011 121419 A | 12/2012 |
| WO | WO 01/77342 A1 | 10/2001 |
| WO | WO 2005/095457 A2 | 10/2005 |
| WO | WO 2009/018386 A1 | 2/2009 |
| WO | WO 2009/080253 A1 | 7/2009 |
| WO | WO 2010/112193 A1 | 10/2010 |

(Continued)

OTHER PUBLICATIONS

Curran et al. (PNAS, 2010 107:4275-4280).*

(Continued)

Primary Examiner — Julie Wu
(74) Attorney, Agent, or Firm — Leon R. Yankwich, Esq.; Thomas R. Berka, Esq.; Yankwich & Associates, P.C.

(57) ABSTRACT

The present invention provides multivalent and multispecific binding proteins that are capable of binding two or more antigens, or two or more epitopes. The present invention also provides methods of making and using such multivalent and multispecific binding proteins, including methods of using such binding proteins for prevention or treatment of various diseases, or for detecting specific antigens in vitro or in vivo.

3 Claims, 7 Drawing Sheets

Specification includes a Sequence Listing.

(56) References Cited

FOREIGN PATENT DOCUMENTS

| WO | WO 2010/115589 A1 | 10/2010 |
|---|---|---|
| WO | WO 2010/145792 A1 | 12/2010 |
| WO | WO 2011/117330 A1 | 9/2011 |
| WO | WO 2012/025525 A1 | 3/2012 |
| WO | WO 2013/026831 A1 | 2/2013 |
| WO | WO 2013/150043 | 10/2013 |
| WO | WO 2014/144357 A1 | 9/2014 |
| WO | WO 2014/161845 A1 | 10/2014 |
| WO | WO 2014/167022 A1 | 10/2014 |

OTHER PUBLICATIONS

International Search Report and Written Opinion, PCT/US2014/072336. dated Apr. 28, 2015, 13 pages.
Aoki et al., "Endothelial Progenitor Cell Capture by Stents Coated With Antibody Against CD34," *J. Am. Coll. Cardiol.*, 45(10): 1574-1579 (2005).
Arancio et al., "RAGE potentiates Aβ-induced perturbation of neuronal function in transgenic mice," *EMBO J.*, 23: 4096-4105 (2004).
Arndt et al., "Bispecific Diabodies for Cancer Therapy," *Methods Mol. Biol.*, 207: 305-321 (2003).
Bargou et al., "Tumor Regression in Cancer Patients by Very Low Doses of a T-Cell-Engaging Antibody," *Science*, 321: 974-977 (2008).
Bornemann et al., "Aβ-Induced Inflammatory Processes in Microglia Cells of APP23 Transgenic Mice," *Am. J. Pathol.*, 158(1): 63-73 (2001).
Bostrom et al., "Variants of the Antibody Herceptin That Interact with HER2 and VEGF at the Antigen Binding Site," *Science*, 323: 1610-1614 (2009).
Boyce et al., "No audible wheezing: nuggets and conundrums from mouse asthma models," *J. Exp. Med.*, 201(12): 1869-1873 (2005).
Brand, D.D., "Rodent Models of Rheumatoid Arthritis," *Comparative Medicine*, 55(2): 114-122 (2005).
Brennan et al., "Preparation of Bispecific Antibodies by Chemical Recombination of Monoclonal Immunoglobulin $G_1$ Fragments," *Science*, 229: 81-83 (1985).
Brinkmann et al., "The making of bispecific antibodies," *mAbs*, 9(2): 182-212 (2017) http://dx.doi.org/10.1080/19420862.2016.1268307.
Buras et al., "Animal Models of Sepsis: Setting the Stage," *Nat. Rev. Drug Discovery*, 4: 854-865 (2005).
Burke et al., "Zotarolimus (ABT-578) eluting stents," *Adv. Drug Del. Rev.*, 58: 437-446 (2006).
Calandra et al., "Protection from septic shock by neutralization of macrophage migration inhibitory factor," *Nature Med.*, 6(2): 164-170 (2000).
Coffman et al., "Nonhuman primate models of asthma," *J. Exp. Med.*, 201(12): 1875-1879 (2005).
Coloma and Morrison, "Design and production of novel tetravalent bispecific antibodies," *Nature Biotechnol.*, 15: 159-163 (1997).
Deane et al., "Rage mediates amyloid-β peptide transport across the blood-brain barrier and accumulation in brain," *Nature Med.*, 9(7): 907-913 (2003).
Descotes J., "Immunotoxicology of Immunomodulators," *Develop. Biol. Standard*, 77: 99-102 (1992).
Dickson, B.J., "Molecular Mechanisms of Axon Guidance," *Science*, 298: 1959-1964 (2002.
DiGiammarino et al., "Ligand association rates to the inner-variable-domain of a dual-variable domain immunoglobulin are significantly impacted by linker design," *mAbs*, 3(5): 487-494 (Sep.-Oct. 2011).
Domeniconi et al., "Overcoming inhibitors in myelin to promote axonal regeneration," *J. Neurolog. Sciences*, 233: 43-47 (2005).
Dong et al., "A stable IgG-like bispecific antibody targeting the epidermal growth factor receptor and the type I insulin-like growth factor receptor demonstrates superior anti-tumor activity," *mAbs* 3: 273-288 (2011).

Doppalapudi et al., "Chemical generation of bispecific antibodies," *Proc. Natl. Acad. Sci. USA*, 107: 22611-22616 (2010).
Durocher et al., "High-level and high-throughput recombinant protein production by transient transfection of suspension-growing human 293-EBNA1 cells," *Nucl. Acids Res.*, 30(2e9): 1-9 (2002).
Economides et al., "Cytokine traps: multi-component, high-affinity blockers of cytokine action," *Nature Med.*, 9(1): 47-52 (2003).
Finotto et al., "Asthmatic changes in mice lacking T-bet are mediated by IL-13," *Int. Immunol.*, 17(8): 993-1007 (2005).
Genain et al., "Creation of a model for multiple sclerosis in *Callithrix jacchus* marmosets," *J. Mol. Med.*, 75(3): 187-197 (1997).
Genovese et al., "Abatacept for Rheumatoid Arthritis Refractory to Tumor Necrosis Factor α Inhibition," *N. Engl. J. Med.*, 353: 1114-1123 (2005).
Glennie et al., "Preparation and Performance of Bispecific F(ab' γ)$_2$ Antibody Containing Thioether-Linked Fab' γ Fragments," *J. Immunol.*, 139(7): 2367-2375 (1987).
Goldspiel et al., "Human Gene Therapy," *Clin. Pharm.*, 12: 488-505 (1993).
Gracie et al., "A proinflammatory role for IL-18 in rheumatoid arthritis," *J. Clin. Invest.*, 104(10): 1393-1401 (1999).
Griffin et al., "Blockade of T Cell Activation Using a Surface-Linked Single Chain Antibody to CTLA-4 (CD152)," *J. Immunol.*, 164: 4433-4442 (2000).
Harriman et al., "Summary of clinical trials in rheumatoid arthritis using infliximab, an anti-TNFα treatment," *Ann. Rheum. Dis.*, 58: (Suppl. I) 161-164 (1999).
Hart et al., "Preclinical efficacy and safety of mepolizumab (SB-240563), a humanized monoclonal antibody to IL-5, in cynomolgus monkeys," *J. Allergy Clin. Immunol.*, 108(2): 250-257 (2001).
Hildebrand et al., "Surface coatings for biological activation and functionalization of medical devices," *Surface & Coatings Technology*, 200: 6318-6324 (2006).
Holliger et al., "'Diabodies': Small bivalent and bispecific antibody fragments," *Proc. Natl. Acad. Sci. USA*, 90: 6444-6448 (1993).
Holliger et al., "Diabodies: small bispecific antibody fragments," *Cancer Immunol. Immunother.*, 45: 128-130 (1997).
Hwang et al., "Cutting Edge: Targeted Ligation of CTLA-4 In Vivo by Membrane-Bound Anti-CTLA-4 Antibody Prevents Rejection of Allogeneic Cells," *J. Immunol.*, 163: 633-637 (2002).
Ito et al., "Transfer of Severe Experimental Autoimmune Encephalomyelitis by IL-12- and IL-18-Potentiated T Cells is Estrogen Sensitive," *J. Immunol.*, 170(9): 4802-4809 (2003).
Jakob et al., "Structure reveals function of the dual variable domain immunoglobulin (DVD-Ig™) molecule," *mAbs*, 5(3): 358-363 (May-Jun. 2013).
Janelsins et al., "Early correlation of microglial activation with enhanced tumor necrosis factor-alpha and monocyte chemoattractant protein-I expression specifically within the entorhinal cortex of triple transgenic Alzheimer's disease mice," *J. Neuroinflammation*, 2(23): 1-12 (2005).
Jones, R., "Rovelizumab—ICOS Corp," *IDrugs*, 3(4): 442-446 (2000).
Karnezis et al., "The neurite outgrowth inhibitor Nogo A is involved in autoimmune-mediated demyelination," *Nature Neurosci.*, 7: 736 (2004).
Karni et al., "IL-18 is linked to raised IFN-y in multiple sclerosis and is induced by activated CD4T cells via CD40-CD40 ligand interactions," *J. Neuroimmunol.*, 125: 134-140 (2002).
Klein, W. L., "Aβtoxicity in Alzheimer's disease: globular oligomers (ADDLs) as new vaccine and drug targets," *Neurochem. Int.*, 41: 345-352 (2002).
Klyubin et al., "Amyloid β protein immunotherapy neutralizes Aβ oligomers that disrupt synaptic plasticity in vivo," *Nature Med.*, 11: 556-561 (2005).
Kriangkum et al., "Bispecific and bifunctional single chain recombinant antibodies," *Biomol. Eng.*, 18: 31-40 (2001).
Leung et al., "Combined Effects of IL-12 and IL-18 on the Induction of Collagen-Induced Arthritis," *J. Immunol.*, 164(12): 6495-6502 (2000).

(56) References Cited

OTHER PUBLICATIONS

Lindhofer et al., "Preferential species-restricted heavy/light chain pairing in rat/mouse quadromas. Implications for a single-step purification of bispecific antibodies," *J. Immunol.*, 155: 219-225 (1995).
Lloyd et al., "Mouse Models of Allergic Airway Disease," *Adv. Immunol.*, 77: 263-295 (2001).
Lu, Dan, et al., "Fab-scFv fusion protein: an efficient approach to production of bispecific antibody fragments," *J. Immunol. Methods*, 267: 213-226 (2002).
Lu et al., "Simultaneous blockade of both the epidermal growth factor receptor and the insulin-like growth factor receptor signaling pathways in cancer cells with a fully human recombinant bispecific antibody," *J. Biol. Chem.*, 279(4): 2856-2865 (2004).
Lublin, F.D., "Relapsing experimental allergic encephalomyelitis an autoimmune model of multiple sclerosis," *Springer Semin. Immunopathol.*, 8: 197-208 (1985).
Luster et al., "Use of animal studies in risk assessment for immunotoxicology," *Toxicology*, 92(1-3): 229-243 (1994).
Mack et al., "A small bispecific antibody construct expressed as a functional single-chain molecule with high tumor cell cytotoxicity," *Proc. Natl. Acad. Sci. USA*, 92: 7021-7025 (1995).
Makwana et al., "Molecular mechanisms in successful peripheral regeneration," *FEBS J.*, 272: 2628-2638 (2005).
Marques et al., "Mediation of the cytokine network in the implantation of orthopedic devices," Chapter 21, In *Biodegradable Systems in Tissue Engineering and Regenerative Medicine*, (Reis et al., eds.) (CRC Press LLC, Boca Raton, 2005) pp. 377-397.
Masliah et al., "Effects of α-Synuclein Immunization in a Mouse Model of Parkinson's Disease," *Neuron*, 46: 857-868 (2005).
McDonnell et al., "TNF Antagonism," In *New Drugs for Asthma, Allergy and COPD* (*Prog Respir Res.*, vol. 31), (Hansel et al., eds.) (Karger, Basel, 2001) pp. 247-250.
McGee et al., "The Nogo-66 receptor: focusing myelin inhibition of axon regeneration," *Trends Neurosciences*, 26(4): 193-198 (2003).
Miller et al., "Design, Construction, and In Vitro Analyses of Multivalent Antibodies," *J. Immunol.*, 170: 4854-4861 (2003).
Milstein et al., "Hybrid hybridomas and their use in immunohistochemistry," *Nature*, 305: 537-540 (1983).
Mizushima et al., "pEF-BOS, a powerful mammalian expression vector," *Nucl. Acids Res.*, 18(17): 5322 (1990).
Morgan and Anderson, "Human Gene Therapy," *Annu. Rev. Biochem.*, 62:191-217 (1993).
Mulligan, R.C., "The Basic Science of Gene Therapy," *Science*, 260: 926-932 (1993).
Nakanishi et al., "Interleukin-18 Regulates Both TH1 and TH2 Responses," *Annu. Rev Immunol.*, 19: 423-474 (2001).
Nelson, R.B., "The Dualistic Nature of Immune Modulation in Alzheimer's Disease: Lessons from the Transgenic Models," *Curr. Pharm. Des.*, 11: 3335-3352 (2005).
Okamoto et al., "Rituximab for Rheumatoid Arthritis," *N. Engl. J. Med.*, 351: 1909 (2004).
Owens et al., "The Immunology of Multiple Sclerosis and Its Animal Model, Experimental Allergic Encephalomyelitis," *Neurol. Clin.*, 13(1): 51-73 (1995).
Padilla et al., "IL-13 Regulates the Immune Response to Inhaled Antigens," *J. Immunol.*, 174(12): 8097-8105 (2005).
Peipp et al., "Bispecific antibodies targeting cancer cells," *Biochem. Soc. Trans.*, 30(4): 507-511 (2002).
Peng, S.L., "Experimental Use of Murine Lupus Models," *Methods Mol. Med.*, 102: 227-272 (2004).
Plückthun and Pack, "New protein engineering approaches to multivalent and bispecific antibody fragments," *Immunotechnology*, 3: 83-105 (1997).
Ridgway et al., "'Knobs-into-holes' engineering of antibody $C_H3$ domains for heavy chain heterodimerization," *Protein Eng.*, 9(7): 617-621 (1996).
Robinson, C., "Gene therapy—proceeding from laboratory to clinic," *Trends Biotechnol.*, 11(5): 155 (1993).

Schaefer et al., "Immunoglobulin domain crossover as a generic approach for the production of bispecific IgG antibodies," *Proc. Natl. Acad. Sci. USA*, 108: 11187-11192 (2011).
Sfikakis et al., "Rituximab anti-B-cell therapy in systemic lupus erythematosus: pointing to the future," *Curr. Opin. Rheumatol.*, 17: 550-557 (2005).
Shepherd et al., "Novel 'inflammatory plaque' pathology in presenilin-1 Alzheimer's disease," *Neuropathol. Appl. Neurobiol.*, 31: 503-511 (2005).
Snibson et al., "Airway remodelling and inflammation in sheep lungs after chronic airway challenge with house dust mite," *Clin. Exp. Allergy* 35: 146-152 (2005).
Soloman, B., "Alzheimer's Disease and Immunotherapy," *Curr. Alzheimer. Res.*, 1: 149-163 (2004).
Staerz et al., "Hybrid antibodies can target sites for attack by T cells," *Nature*, 314: 628-631 (1985).
Stamper et al., "Crystal structure of the B7-1/CTLA-4 complex that inhibits human immune responses," *Nature*, 410: 608-611 (2001).
Steinman et al., "Virtues and pitfalls of EAE for the development of therapies for multiple sclerosis," *Trends Immunol.*, 26(11):565-571 (2005).
Stubenrauch et al., "Impact of Molecular Processing in the Hinge Region of Therapeutic IgG4 Antibodies on Disposition Profiles in Cynomolgus Monkeys," *Drug Metab. Dispos.*, 38: 84-91 (2010).
't Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Teng et al., "Nogo Signaling and Non-Physical Injury-Induced Nervous System Pathology," *J. Neurosci. Res.*, 79: 273-278 (2005).
Tolstoshev, P., "Gene Therapy, Concepts, Current Trials and Future Directions," *Annu. Rev. Pharmacol. Toxicol.*, 32: 573-596 (1993).
Tuohy et al., "Spontaneous Regression of Primary Autoreactivity during Chronic Progression of Experimental Autoimmune Encephalomyelitis and Multiple Sclerosis," *J. Exp Med.*, 189(7): 1033-1042 (1999).
van der Neut Kolfschoten, et al., "Anti-Inflammatory Activity of Human IgG4 Antibodies by Dynamic Fab Arm Exchange," *Science*, 317: 1554-1557 (2007).
von Mehren et al., "Monoclonal Antibody Therapy for Cancer," *Annu. Rev. Med.*, 54: 343-369 (2003).
Wu and Wu., "Delivery systems for gene therapy," *Biotherapy*, 3: 87-95 (1991).
Wu, A.M., et al., "Tumor localization of anti-CEA single-chain Fvs: improved targeting by non-covalent dimers," *Immunotechnology*, 2(1): 21-36 (1996).
Wu, Peng, et al., "Drug/device combinations for local drug therapies and infection prophylaxis," *Biomaterials*, 27: 2450-2467 (2006).
Xu, Gang, et al., "Recombinant DNA vaccine encoding multiple domains related to inhibition of neurite outgrowth: a potential strategy for axonal regeneration," *J. Neurochem.*, 91: 1018-1023 (2004).
Zola et al., "CD molecules 2005: human cell differentiation molecules," *Blood*, 106: 3123-3126 (2005).
EPO Communication dated Aug. 9, 2017, enclosing Extended European Search Report, which includes (pursuant to Rule 62 EPC) the supplementary European search report, and the European search opinion dated Jul. 28, 2017, issued in corresponding EP Application No. 14 87 7308.8.
Griffin et al., "IL-17 and TNF-a Sustain Neutrophil Recruitment during Inflammation through Synergistic Effects on Endothelial Activation," *J. Immunol.*, 188(12): 6287-6299 (2012).
Stanglmaier et al., "Bi20 (FBTA05), a novel trifunctional bispecific antibody (anti-CD20 x anti-CD3), mediates efficient killing of B-cell lymphoma cells even with very low CD20 expression levels," *Int. J. Cancer*, 123(5): 1181-1189 (2008).
Baker et al., "NF-κB, inflammation and metabolic disease," *Cell Metab.*, 13(1): 11-22 (2011) (doi:10.1016/j.cmet.2010.12.008).
Kadomatsu et al., "Angiopoietin-like proteins: emerging targets for treatment of obesity and related metabolic diseases," *FEBS J.*, 278: 559-564 (2010).
Oike et al., "Angiopoietin-Like Syndrome and Cardiovascular Proteins—Potential Therapeutic Targets for Metabolic Disease," *Cir. J.*, 73: 2192-2197 (2009).

(56) References Cited

OTHER PUBLICATIONS

Peterson et al., "Macrophage-Targeted Therapeutics for Metabolic Disease," *Trends Pharmacol. Sci.*, (doi.org/10.1016/j.tips.2018.03.001).

Shan et al., "The Angiopoietin-like Proteins ANGPTL3 and ANGPTL4 Inhibit Lipoprotein Lipase Activity through Distinct Mechanisms," *J. Biol. Chem.*, 284(3): 1419-1424 (2009).

\* cited by examiner

D:Days. IX 1-15: clone numbers

FABS-IN-TANDEM IMMUNOGLOBULIN AND USES THEREOF

INCORPORATION BY REFERENCE

This application is a national stage application of International Application No. PCT/US2014/072336, filed Dec. 24, 2014, which claims priority to International Application No. PCT/CN2013/090923, filed Dec. 30, 2013, each of which is herein incorporated by reference in its entirety.

FIELD OF INVENTION

The present invention relates to multivalent and multispecific binding proteins, and to methods of making and using multivalent and multispecific binding proteins.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EPBI_001_01US_SeqList_ST25.txt, date recorded: Jun. 1, 2015, file size 98 KB).

BACKGROUND OF THE INVENTION

Bispecific or multispecific antibodies have been generated in attempts to prepare molecules useful for the treatment of various inflammatory diseases, cancers, and other disorders.

Bispecific antibodies have been produced using the quadroma technology (see Milstein, C. and A. C. Cuello, Nature, 1983. 305(5934): p. 537-40) based on the somatic fusion of two different hybridoma cell lines expressing murine monoclonal antibodies with the desired specificities of the bispecific antibody. Bispecific antibodies can also be produced by chemical conjugation of two different mAbs (see Staerz, U. D., et al., Nature, 1985. 314(6012): p. 628-31). Other approaches have used chemical conjugation of two different monoclonal antibodies or smaller antibody fragments (see Brennan, M., et al., Science, 1985. 229 (4708): p. 81-3).

Another method is the coupling of two parental antibodies with a hetero-bifunctional crosslinker. In particular, two different Fab fragments have been chemically crosslinked at their hinge cysteine residues in a site-directed manner (see Glennie, M. J., et al., J Immunol, 1987. 139(7): p. 2367-75).

Other recombinant bispecific antibody formats have been developed in the recent past (see Kriangkum, J., et al., Biomol Eng, 2001. 18(2): p. 31-40). Amongst them tandem single-chain Fv molecules and diabodies, and various derivatives thereof, have been used for the construction of recombinant bispecific antibodies. Normally, construction of these molecules starts from two single-chain Fv (scFv) fragments that recognize different antigens (see Economides, A. N., et al., Nat Med, 2003. 9(1): p. 47-52). Tandem scFv molecules (taFv) represent a straightforward format simply connecting the two scFv molecules with an additional peptide linker. The two scFv fragments present in these tandem scFv molecules form separate folding entities. Various linkers can be used to connect the two scFv fragments and linkers with a length of up to 63 residues (see Nakanishi, K., et al Annu Rev Immunol, 2001. 19: p. 423-74).

In a recent study, in vivo expression by transgenic rabbits and cattle of a tandem scFv directed against CD28 and a melanoma-associated proteoglycan was reported (see Gracie, J. A., et al., J Clin Invest, 1999. 104(10): p. 1393-401). In this construct the two scFv molecules were connected by a CH1 linker and serum concentrations of up to 100 mg/L of the bispecific antibody were found. A few studies have now reported expression of soluble tandem scFv molecules in bacteria (see Leung, B. P., et al., J Immunol, 2000. 164(12): p. 6495-502; Ito, A., et al., J Immunol, 2003. 170(9): p. 4802-9; Karni, A., et al., J Neuroimmunol, 2002. 125(1-2): p. 134-40) using either a very short Ala3 linker or long glycine/serine-rich linkers.

In a recent study, phage display of a tandem scFv repertoire containing randomized middle linkers with a length of 3 or 6 residues enriched those molecules which are produced in soluble and active form in bacteria. This approach resulted in the isolation of a preferred tandem scFv molecule with a 6 amino acid residue linker (see Arndt, M. and J. Krauss, Methods Mol Biol, 2003. 207: p. 305-21).

Bispecific diabodies (Db) utilize the diabody format for expression. Diabodies are produced from scFv fragments by reducing the length of the linker connecting the VH and VL domain to approximately 5 residues (see Peipp, M. and T. Valerius, Biochem Soc Trans, 2002. 30(4): p. 507-11). This reduction of linker size facilitates dimerization of two polypeptide chains by crossover pairing of the VH and VL domains. Bispecific diabodies are produced by expressing two polypeptide chains with either the structure VHA-VLB and VHB-VLA (VH-VL configuration) or VLA-VHB and VLB-VHA (VL-VH configuration) within the same cell. A recent comparative study demonstrates that the orientation of the variable domains can influence expression and formation of active binding sites (see Mack, M., G. Riethmuller, and P. Kufer, Proc Natl Acad Sci USA, 1995. 92(15): p. 7021-5).

One approach to force the generation of bispecific diabodies is the production of knob-into-hole diabodies (see Holliger, P., T. Prospero, and G. Winter, Proc Natl Acad Sci USA, 1993. 90(14): p. 6444-8.18). This was demonstrated for a bispecific diabody directed against HER2 and CD3. A large knob was introduced in the VH domain by exchanging Val37 with Phe and Leu45 with Trp and a complementary hole was produced in the VL domain by mutating Phe98 to Met and Tyr87 to Ala, either in the anti-HER2 or the anti-CD3 variable domains. By using this approach the production of bispecific diabodies could be increased from 72% by the parental diabody to over 90% by the knob-into-hole diabody.

Single-chain diabodies (scDb) represent an alternative strategy to improve the formation of bispecific diabody-like molecules (see Holliger, P. and G. Winter, Cancer Immunol Immunother, 1997. 45(3-4): p. 128-30; Wu, A. M., et al., Immunotechnology, 1996. 2(1): p. 21-36). Bispecific single-chain diabodies are produced by connecting the two diabody-forming polypeptide chains with an additional middle linker with a length of approximately 15 amino acid residues. Consequently, all molecules with a molecular weight corresponding to monomeric single-chain diabodies (50-60 kDa) are bispecific. Several studies have demonstrated that bispecific single chain diabodies are expressed in bacteria in soluble and active form with the majority of purified molecules present as monomers (see Holliger, P. and G. Winter, Cancer Immunol Immunother, 1997. 45(3-4): p. 128-30; Wu, A. M., et al., Immunotechnology, 1996. 2(1): p. 21-36; Pluckthun, A. and P. Pack, Immunotechnology, 1997. 3(2): p. 83-105; Ridgway, J. B., et al., Protein Eng, 1996. 9(7): p. 617-21).

Diabody have been fused to Fc to generate more Ig-like molecules, named di-diabody (see Lu, D., et al., J Biol Chem, 2004. 279(4): p. 2856-65). In addition, multivalent antibody construct comprising two Fab repeats in the heavy chain of an IgG and capable of binding four antigen molecules has been described (see U.S. Pat. No. 8,722,859 B2, and Miller, K., et al., J Immunol, 2003. 170(9): p. 4854-61).

The most recent examples are tetravalent IgG-single-chain variable fragment (scFv) fusions (Dong J, et al. 2011 MAbs 3:273-288; Coloma M J, Morrison S L 1997 Nat Biotechnol 15:159-163; Lu D, et al. 2002 J Immunol Methods 267:213-226), catumaxomab, a trifunctional rat/mouse hybrid bispecific epithelial cell adhesion molecule-CD3 antibody (Lindhofer H, et al 1995 J Immunol 155:219-225), the bispecific CD19-CD3 scFv antibody blinatumomab (Bargou R, et al. 2008 Science 321:974-977), "dual-acting Fab" (DAF) antibodies (Bostrom J, et al. 2009 Science 323:1610-1614), covalently linked pharmacophore peptides to catalytic anti-bodies (Doppalapudi V R, et al. 2010 Proc Natl Acad Sci USA 107:22611-22616), use of the dynamic exchange between half IgG4 molecules to generate bispecific antibodies (van der Neut Kolfschoten M, et al. 2007 Science 317:1554-1557; Stubenrauch K, et al. 2010 Drug Metab Dispos 38:84-91), or by exchange of heavy-chain and light-chain domains within the antigen binding fragment (Fab) of one half of the bispecific antibody (CrossMab format) (Schaefer W et al 2011 Proc Natl Acad Sci 108: 11187-92).

There is a need in the art for single molecular entities with dual antigen binding function, and for methods of generating such multivalent and multispecific binding proteins. The present invention addresses these and other needs.

SUMMARY OF THE INVENTION

The present invention provides multivalent and multispecific binding proteins, and methods of making and using such binding proteins. In one embodiment, the multivalent and multispecific binding proteins provided herein are Fabs-in-tandem immunoglobulins (FIT-Ig), and are capable of binding two or more antigens, or two or more epitopes of the same antigen, or two or more copies of the same epitope. The multivalent and multispecific binding proteins provided herein are useful for treatment and/or prevention of acute and chronic inflammatory diseases and disorders, autoimmune diseases, cancers, spinal cord injuries, sepsis, and other diseases, disorders, and conditions. Pharmaceutical compositions comprising the multivalent and multispecific binding proteins are provided herein. In addition, nucleic acids, recombinant expression vectors, and host cells for making such FIT-Igs are provided herein. Methods of using the FIT-Igs of the invention to detect specific antigens, in vivo or in vitro, are also encompassed by the invention.

The present invention provides a family of binding proteins that are capable of binding two or more antigens, e.g., with high affinity. In one aspect, the present invention provides an approach to construct a bispecific binding protein using two parental monoclonal antibodies: mAb A, which binds to antigen A, and mAb B, which binds to antigen B. The binding proteins disclosed herein, in one embodiment, are capable of binding antigens, cytokines, chemokines, cytokine receptors, chemokine receptors, cytokine- or chemokine-related molecules, or cell surface proteins.

Thus, in one aspect, binding proteins capable of binding two or more antigens are provided. In one embodiment, the present invention provides a binding protein comprising at least two polypeptide chains, wherein the polypeptide chains pair to form IgG-like molecules capable of binding two or more antigens. In one embodiment, the binding protein comprises two, three, four, five, or more polypeptide chains. In one embodiment, the binding protein comprises at least one $VL_A$, at least one $VL_B$, at least one $VH_A$, at least one $VH_B$, at least one CL, and at least one CH1, wherein VL is a light chain variable domain, VH is a heavy chain variable domain, CL is a light chain constant domain, CH1 is the first constant domain of the heavy chain, A is a first antigen, and B is a second antigen. In a further embodiment, the first polypeptide chain comprises a $VL_A$, a CL, a $VH_B$, and a CH1. In a further embodiment, the binding protein further comprises an Fc. In another embodiment, the Fc region is a variant Fc region. In a further embodiment, the variant Fc region exhibits modified effector function, such as ADCC or CDC. In another embodiment, the variant Fc region exhibits modified affinity or avidity for one or more FcγR.

In one embodiment, the binding protein comprises three polypeptide chains, wherein the first polypeptide chain comprises a $VL_A$, a CL, a $VH_B$, and a CH1, the second polypeptide chain comprises $VH_A$ and CH1, and the third polypeptide chain comprises $VL_B$ and CL. In a further embodiment, the first polypeptide chain of the binding protein further comprises an Fc. In another embodiment, the binding protein comprises two polypeptide chains, wherein the first polypeptide chain comprises a $VL_A$, a CL, a $VH_B$, and a CH1, the second polypeptide chain comprises $VH_A$, CH1, $VL_B$, and CL. In a further embodiment, the first polypeptide chain further comprises an Fc.

In one embodiment, the binding protein comprises three polypeptide chains, and their corresponding cDNA during co-transfection are present at a molar ratio of first:second: third of 1:1:1, 1:1.5:1, 1:3:1, 1:1:1.5, 1:1:3, 1:1.5:1.5, 1:3: 1.5, 1:1.5:3, or 1:3:3. In another embodiment, the binding protein comprises two polypeptide chains, and their corresponding cDNA during co-transfection are present at a molar ratio of first:second of 1:1, 1:1.5, or 1:3, or any other ratios, through optimization, in an effort to maximize the monomeric FIT-Ig fraction in any given transfection.

In one embodiment, the binding protein of the present invention does not comprise a peptide linker. In one embodiment, the binding protein of the present invention comprises at least one amino acid or polypeptide linker. In a further embodiment, the linker is selected from the group consisting of G, GS, SG, GGS, GSG, SGG, GGG, GGGS, SGGG, GGGGS, GGGGSGS, GGGGSGS, GGGGSGGS, GGGGSGGGS, GGGGSGGGSGGGS, AKTTP-KLEEGEFSEAR, AKTTPKLEEGEFSEARV, AKTTP-KLGG, SAKTTPKLGG, AKTTPKLEEGEFSEARV, SAK-TTP, SAKTTPKLGG, RADAAP, RADAAPTVS, RADAAAGGPGS, RADAAAA($G_4S$)$_4$, SAKTTP, SAK-TTPKLGG, SAKTTPKLEEGEFSEARV, ADAAP, ADAAPTVSIFPP, TVAAP, TVAAPSVFIFPP, QPKAAP, QPKAAPSVTLFPP, AKTTPP, AKTTPPSVTPLAP, AKT-TAP, AKTTAPSVYPLAP, ASTKGP, ASTKGPSVFPLAP, GENKVEYAPALMALS, GPAKELTPLKEAKVS, and GHEAAAVMQVQYPAS. The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions.

In one embodiment, the binding protein comprises a first polypeptide comprising, from amino to carboxyl terminus, $VL_A$-CL-$VH_B$-CH1-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VH_B$-CH1-$VL_A$-CL-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VL_A$-CL-$VH_B$-CH1-Fc, and a second polypeptide chain comprising, from amino to carboxyl terminus, $VH_A$-CH1-$VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, binding protein comprises a first polypeptide comprising, from amino to carboxyl terminus, $VH_B$-CH1-$VL_A$-CL-Fc, and a second polypeptide chain comprising, from amino to carboxyl terminus, $VL_B$-CL-$VH_A$-CH1; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

The binding proteins of the present invention are capable of binding pairs of cytokines. For example, the binding proteins of the present invention are capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; PDGFR and VEGF, IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2. In one embodiment, the binding proteins of the present invention are capable of binding IL-17 and IL-20. The binding proteins of the present invention, in one embodiment, are capable of binding IL-17 and IL-20 and comprise variable heavy and light chains derived from the anti-IL-17 antibody LY and the anti-IL-20 antibody 15D2. In one embodiment, the binding proteins of the present invention are capable of binding IL-17 and TNF. The binding proteins of the present invention, in one embodiment, are capable of binding IL-17 and TNF and comprise variable heavy and light chains derived from the anti-IL-17 antibody LY and the TNF antibody golimumab.

In one embodiment, the binding proteins of the present invention bind IL-17 and IL-20 and comprise a first polypeptide comprising, consisting essentially of, or consisting of an amino acid sequence selected from the group consisting of SEQ ID NOs: 15, 25, and 27; a second polypeptide chain comprising, consisting essentially of, or consisting of an amino acid sequence according to SEQ ID NO: 21; and a third polypeptide chain comprising, consisting essentially of, or consisting of a sequence according to SEQ ID NO: 23. In another embodiment, the binding proteins of the present invention bind IL-27 and IL-20 and comprise a first polypeptide chain comprising, consisting essentially of, or consisting of an amino acid sequence selected from the group consisting of SEQ ID NOs: 15, 25, and 27, and a second polypeptide chain comprising, consisting essentially of, or consisting of an amino acid sequence selected from the group consisting of SEQ ID NOs: 29, 30, and 31.

In one embodiment, the binding proteins of the present invention bind TNF and IL-17 and comprise a first polypeptide comprising, consisting essentially of, or consisting of an amino acid sequence according to SEQ ID NOs: 87; a second polypeptide chain comprising, consisting essentially of, or consisting of an amino acid sequence according to SEQ ID NO: 89; and a third polypeptide chain comprising, consisting essentially of, or consisting of a sequence according to SEQ ID NO: 91.

In another embodiment, the binding protein is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, CD138 and CD20; CD138 and CD40; CD19 and CD20; CD20 and CD3; CD3 and CD33; CD3 and CD133; CD47 and CD20, CD38 and CD138; CD38 and CD20; CD20 and CD22; CD38 and CD40; CD40 and CD20; CD-8 and IL-6; CSPGs and RGM A; CTLA-4 and BTNO2; IGF1 and IGF2; IGF1/2 and Erb2B; IGF-1R and EGFR; EGFR and CD13; IGF-1R and ErbB3; EGFR-2 and IGFR; VEGFR-2 and Met; VEGF-A and Angiopoietin-2 (Ang-2); IL-12 and TWEAK; IL-13 and IL-1beta; PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A; NgR and RGM A; NogoA and RGM A; OMGp and RGM A; PDL-1 and CTLA-4; CTLA-4 and PD-1; PD-1 and TIM-3; RGM A and RGM B; Te38 and TNFα; TNFα and Blys; TNFα and CD-22; TNFα and CTLA-4 domain; TNFα and GP130; TNFα and IL-12p40; and TNFα and RANK ligand, Factor IXa, Factor X. In one embodiment, the binding proteins of the present invention are capable of binding CD3 and CD20. The binding proteins of the present invention, in one embodiment, are capable of binding CD3 and CD20 and comprise variable heavy and light chains derived from the anti-CD3 antibody OKT3 and the anti-CD20 antibody ofatumumab. In one embodiment, the binding proteins of the present invention are capable of binding CTLA-4 and PD-1. The binding proteins of the present invention, in one embodiment, are capable of binding CTLA-4 and PD-1 and comprise variable heavy and light chains derived from the CTLA-4 antibody ipilimumab and the PD-1 antibody nivolumab.

In one embodiment, the binding proteins of the present invention bind CD3 and CD20 and comprise a first polypeptide chain comprising, consisting essentially of, or consisting of an amino acid sequence selected from the group consisting of SEQ ID NOs: 41 and 48; a second polypeptide chain comprising, consisting essentially of, or consisting of an amino acid sequence according to SEQ ID NO: 44; and a third polypeptide chain comprising, consisting essentially of, or consisting of an amino acid sequence according to SEQ ID NO: 46.

In one embodiment, the binding proteins of the present invention bind CTLA-4 and PD-1 and comprise a first polypeptide chain comprising, consisting essentially of, or consisting of an amino acid sequence according to SEQ ID NO: 92; a second polypeptide chain comprising, consisting essentially of, or consisting of an amino acid sequence according to SEQ ID NO: 95; and a third polypeptide chain comprising, consisting essentially of, or consisting of an amino acid sequence according to SEQ ID NO: 97.

In one embodiment, the binding protein provided herein is capable of binding one or more epitopes on CTLA-4. In one embodiment, the binding protein provided herein is capable of binding one or more peptides on PD-1.

In one embodiment, the binding protein is capable of binding one or more epitopes on one or more immune checkpoint protein on T cells such as, for example, TIM-3, Lag3, ICOS, BTLA, CD160, 2B4, KIR, CD137, CD27, OX40, CD40L, and A2aR. In another embodiment, the binding protein is capable of binding one or more epitopes on one or more tumor cell surface protein that is involved with immune checkpoint pathways, such as, for example, PD-L1, PD-L2, Galectin9, HVEM, CD48, B7-1, B7-2, ICOSL, B7-H3, B7-H4, CD137L, OX40L, CD70, and CD40.

In one aspect, the present invention provides pharmaceutical compositions comprising the binding proteins described herein. In one embodiment, provided herein are pharmaceutical compositions comprising the binding protein of any one of the preceding claims and one or more pharmaceutically acceptable carrier.

In another aspect, the present invention provides methods of treating or preventing an inflammatory disease, autoimmune disease, neurodegenerative disease, cancer, sepsis, or spinal cord injury in a subject in need thereof. In one embodiment, the method comprises administering to a subject an effective amount of one or more of the binding proteins provided herein, or one or more pharmaceutical compositions comprising the binding proteins provided herein and a pharmaceutically acceptable carrier. Uses of the binding proteins described herein in the manufacture of a medicament for treatment or prevention of an inflammatory disease, autoimmune disease, neurodegenerative disease, cancer, or spinal cord injury are also provided herein. In one embodiment, the inflammatory disease, autoimmune disease, or neurodegenerative disease is selected from the group consisting of asthma, rheumatoid arthritis, systemic lupus erythematosus, multiple sclerosis, Alzheimer's disease, or Parkinson's disease.

In one embodiment, the present disclosure provides methods for treating or preventing rheumatoid arthritis, psoriasis, osteoporosis, stroke, liver disease, or oral cancer to a subject in need thereof, the method comprising administering to the subject a FIT-Ig binding protein described herein, wherein the binding protein is capable of binding IL-17 and IL-20. In a further embodiment, the FIT-Ig binding protein comprises an amino acid sequence selected from SEQ ID NOs: 15, 25, and 27; and amino acid sequence according to SEQ ID NO: 21; and an amino acid sequence according to SEQ ID NO: 23. In another embodiment, the FIT-Ig binding protein comprises an amino acid sequence selected from SEQ ID NOs: 15, 25, and 27; and an amino acid sequence selected from SEQ ID NOs: 29, 30 and 31.

In one embodiment, the present disclosure provides methods for treating or preventing a B cell cancer in a subject in need thereof, the method comprising administering to the subject a FIT-Ig binding protein, wherein the FIT-Ig binding protein is capable of binding one or more B cell antigen. In a further embodiment, the FIT-Ig binding protein is capable of binding CD20. In a further embodiment, the FIT-Ig binding protein is capable of binding CD20 and another antigen. In a further embodiment, the binding protein is capable of binding CD3 and CD20. In a further embodiment, the cancer is a B cell cancer. In a still further embodiment, the B cell cancer is selected from the group consisting of Hodgkin's lymphoma, non-Hodgkin's lymphoma [NHL], precursor B cell lymphoblastic leukemia/lymphoma, mature B cell neoplasms, B cell chronic lymphocytic leukemia/small lymphocytic lymphoma, B cell prolymphocytic leukemia, lymphoplamacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma. In one embodiment, the present disclosure provides methods for treating or preventing a B cell cancer in a subject in need thereof, the method comprising administering to the subject a FIT-Ig binding protein, wherein the FIT-Ig binding protein comprises an amino acid sequence according to SEQ ID NOs: 41 or 48; and amino acid sequence according to SEQ ID NO: 44, and an amino acid sequence according to SEQ ID NO: 46.

In one embodiment, the present disclosure provides methods for treating or preventing an autoimmune disease, inflammatory disease, or infection in a subject in need thereof, the method comprising administering to the subject a FIT-Ig binding protein described herein, wherein the binding protein is capable of binding TNF and IL-17. In a further embodiment, the FIT-Ig binding protein comprises sequences according to SEQ ID NOs: 87, 89, and 91. In another embodiment, the present disclosure provides methods for treating or preventing an autoimmune or inflammatory disease, the method comprising administering to the subject a FIT-Ig binding protein, wherein the binding protein is capable of binding TNF and IL-17, and wherein the autoimmune or inflammatory disease is selected from the group consisting of Crohn's disease, psoriasis (including plaque psoriasis), arthritis (including rheumatoid arthritis, psoriatic arthritis, osteoarthritis, or juvenile idiopathic arthritis), multiple sclerosis, ankylosing spondylitis, spondylosing arthropathy, systemic lupus erythematosus, uveitis, sepsis, neurodegenerative diseases, neuronal regeneration, spinal cord injury, primary and metastatic cancers, a respiratory disorder; asthma; allergic and nonallergic asthma; asthma due to infection; asthma due to infection with respiratory syncytial virus (RSV); chronic obstructive pulmonary disease (COPD); a condition involving airway inflammation; eosinophilia; fibrosis and excess mucus production; cystic fibrosis; pulmonary fibrosis; an atopic disorder; atopic dermatitis; urticaria; eczema; allergic rhinitis; allergic enterogastritis; an inflammatory and/or autoimmune condition of the skin; an inflammatory and/or autoimmune condition of gastrointestinal organs; inflammatory bowel diseases (IBD); ulcerative colitis; an inflammatory and/or autoimmune condition of the liver; liver cirrhosis; liver fibrosis; and liver fibrosis caused by hepatitis B and/or C virus; scleroderma. In another embodiment, In another embodiment, the present disclosure provides methods for treating or preventing cancer in a subject in need thereof, the method comprising administering to the subject a FIT-Ig binding protein described herein, wherein the binding protein is capable of binding TNF and IL-17. In a further embodiment, the cancer is hepatocellular carcinoma; glioblastoma; lymphoma; or Hodgkin's lymphoma. In another embodiment, the present disclosure provides methods for treating or preventing and infection in a subject in need thereof, the method comprising administering to the subject a FIT-Ig binding protein described herein, wherein the infection is a viral infection, a bacterial infection, a parasitic infection, HTLV-1 infection. In one embodiment, the present disclosure provides methods for suppression of expression of protective type 1 immune responses, and suppression of expression of a protective type 1 immune response during vaccination.

In one embodiment, the present disclosure provides methods for treating rheumatoid arthritis in a subject in need thereof, the method comprising administering to the subject a FIT-Ig binding protein, wherein the binding protein comprises sequences according to SEQ ID NOs: 87, 89, and 91.

In one embodiment, the present disclosure provides methods for treating or preventing cancer in a subject in need thereof, the method comprising administering to the subject a FIT-Ig binding protein described herein, wherein the binding protein is capable of binding CTLA-4 and PD-1. In a further embodiment, the FIT-Ig binding protein comprises an amino acid sequence comprising SEQ ID NOs: 92, 95, and 97. In another embodiment, the present disclosure provides methods for treating or preventing cancer in a subject in need thereof, wherein the binding protein is capable of binding CTLA-4 and PD-1, and wherein the cancer is a cancer typically responsive to immunotherapy. In another embodiment, the cancer is a cancer that has not been associated with immunotherapy. In another embodiment, the cancer is a cancer that is a refractory or recurring malignancy. In another embodiment, the binding protein inhibits the growth or survival of tumor cells. In another embodiment, the cancer is selected from the group consisting of melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

In one embodiment, the present disclosure provides methods for treating or preventing melanoma in a subject in need thereof, the method comprising administering to the subject a FIT-Ig binding protein described herein, wherein the binding protein is capable of binding CTLA-4 and PD-1. In a further embodiment, the present disclosure provides methods for treating or preventing melanoma in a subject in need thereof, wherein the method comprises administering to the subject a FIT-Ig binding protein comprising amino acid sequences according to SEQ ID NOs: 92, 95, and 97.

In another embodiment, the present disclosure provides methods for treating or preventing infections or infectious disease in a subject in need thereof, the method comprising administering to the subject a FIT-Ig binding protein described herein, wherein the binding protein is capable of binding CTLA-4 and PD-1. In one embodiment, the FIT-Ig binding protein is administered alone, or in combination with vaccines, to stimulate the immune response to pathogens, toxins, and self-antigens. Therefore, in one embodiment, the binding proteins provided herein can be used to stimulate immune response to viruses infectious to humans, such as, but not limited to, human immunodeficiency viruses, hepatitis viruses class A, B and C, Epstein Barr virus, human cytomegalovirus, human papilloma viruses, herpes viruses, bacteria, fungal parasites, or other pathogens.

DETAILED DESCRIPTION

Figure 1:
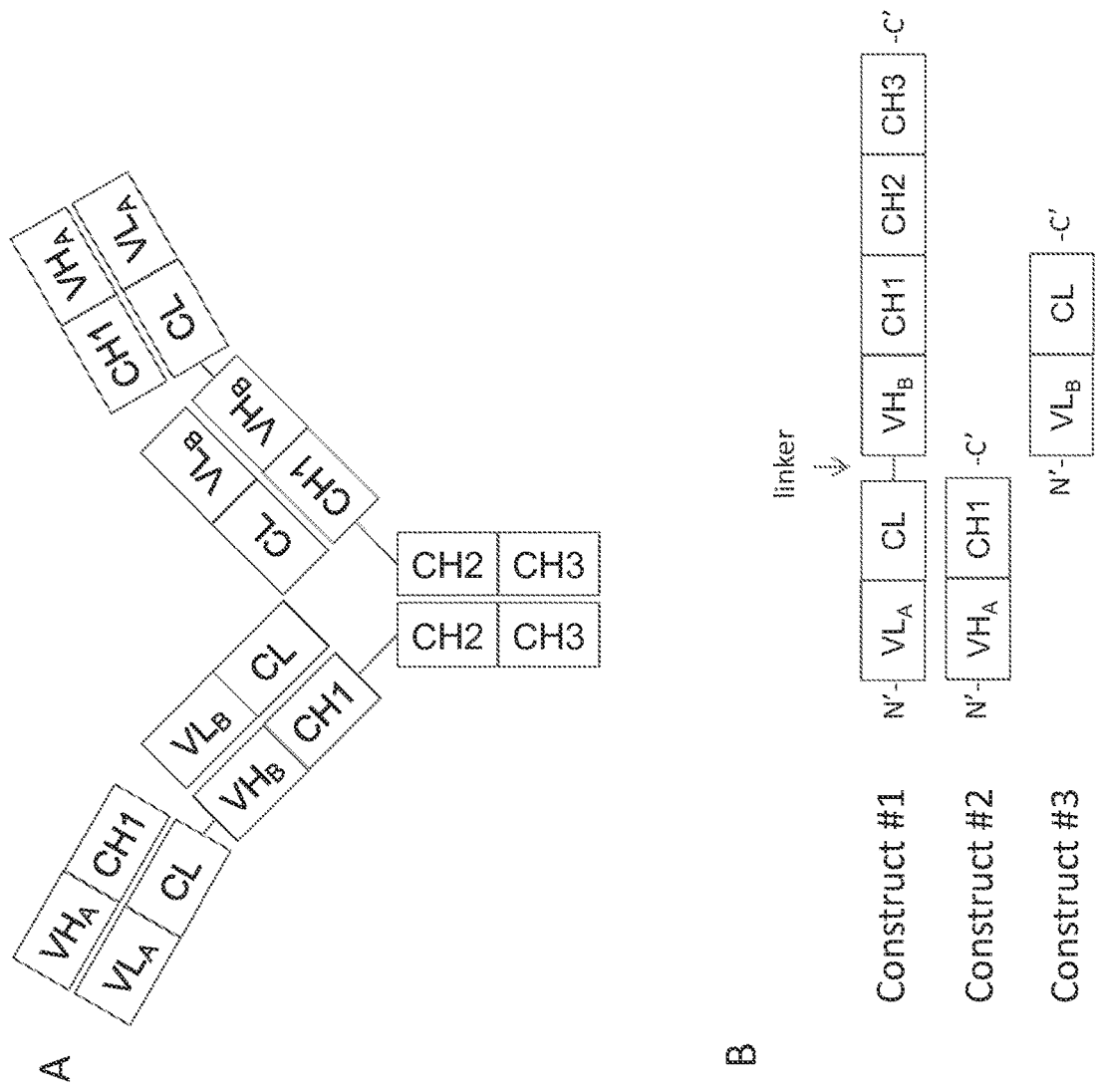
FIG. 1A shows the structure of FIT-Igs that are made up of three constructs, such as FIT1-Ig, FIT2-Ig, and FIT3-Ig.
FIG. 1B shows the three constructs used to prepare such FIT1-Igs.

The present invention relates to multivalent and multi-specific binding proteins, methods of making the binding proteins, and to their uses in the prevention and/or treatment of acute and chronic inflammatory diseases and disorders, cancers, and other diseases. This invention pertains to multivalent and/or multispecific binding proteins capable of binding two or more antigens. Specifically, the invention relates to Fabs-in-tandem immunoglobulins (FIT-Ig), and pharmaceutical compositions thereof, as well as nucleic acids, recombinant expression vectors and host cells for making such FIT-Igs. Methods of using the FIT-Igs of the invention to detect specific antigens, either in vitro or in vivo are also encompassed by the invention.

The novel family of binding proteins provided herein are capable of binding two or more antigens, e.g., with high affinity. Specifically, the present invention provides an approach to construct a bispecific binding protein using 2 parental monoclonal antibodies: mAb A, which binds to antigen a; and mAb B, which binds to antigen b.

In one aspect, the present invention provides a binding protein comprising a variable light chain specific for a first antigen or epitope, a first light chain constant domain, a variable heavy chain specific for a second antigen or epitope, a first heavy chain CH1, a variable heavy chain specific for the first antigen or epitope, a second heavy chain CH1, a variable heavy chain specific for the second antigen or epitope, and a second light chain constant domain. In one embodiment, the binding protein further comprises an Fc region. The binding protein may further comprise one or more amino acid or polypeptide linker linking two or more of the components of the binding protein. For example, the binding protein may comprise a polypeptide linker linking the light chain variable region to the light chain constant region.

In one embodiment, the present disclosure provides a binding protein comprising a polypeptide chain comprising $VL_A$-CL-(X1)n-$VH_B$-CH1-(X2)n, wherein VLA is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1.

In one embodiment, the invention provides a binding protein comprising three different polypeptide chains (FIG. 1), wherein the first polypeptide chain (construct #1) comprises $VL_A$-CL-(X1)n-$VH_B$-CH1-(X2)n, wherein VLA is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #2) comprises $VH_A$-CH1, wherein $VH_A$ is the heavy chain variable domain of mAb A, and CH1 is the first constant domain of the heavy chain. The third polypeptide chain (construct #3) comprises $VL_B$-CL, wherein $VL_B$ is the light chain variable domain of mAb B, and CL is the constant domain of the light chain.

In another embodiment, the invention provides a binding protein comprising three different polypeptide chains with the overall molecular design similar to the previous embodiment except the order of the variable domains are reversed. In the embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VH_A$-CH1, wherein $VH_A$ is the heavy chain variable domain of mAb A and CH1 is the first constant domain of the heavy chain. The third polypeptide chain comprises $VL_B$-CL, wherein $VL_B$ is the light chain variable domain of mAb B and CL is the constant domain of the light chain.

In another embodiment the invention provides a binding protein comprising two different polypeptide chains (FIG. 2), wherein the first polypeptide chain (construct #1) comprises $VL_A$-CL-(X1)n-$VH_B$-CH1-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #4) comprises $VH_A$-CH1-(X3)n-$VL_B$-CL, wherein $VH_A$ is the heavy chain variable domain of mAb A, CH1 is the first constant domain of the heavy chain, X3 represents an amino acid or polypeptide that is not a constant domain, n is 0 or 1, $VL_B$ is the light chain variable domain of mAb B, and CL is the constant domain of the light chain.

In another embodiment the invention provides a binding protein comprising two polypeptide chains with the overall molecular design similar to the previous embodiment except the order of the variable domains are reversed. In this embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VL_B$-CL-(X3)n-$VH_A$-CH1, wherein $VH_A$ is the heavy chain variable domain of mAb A, CH1 is the first constant domain of the heavy chain, X3 represents an amino acid or an oligopeptide linker, n is 0 or 1, $VL_B$ is the light chain variable domain of mAb B, and CL is the constant domain of the light chain.

In one embodiment, the VH and VL domains in the binding protein are selected from the group consisting of murine heavy/light chain variable domains, fully human heavy/light chain variable domains, CDR grafted heavy/light chain variable domains, humanized heavy/light chain variable domains, and mixtures thereof. In a preferred embodiment $VH_A/VL_A$ and $VH_B/VL_B$ are capable of binding the same antigen. In another embodiment $VH_A/VL_A$ and $VH_B/VL_B$ are capable of binding different antigens.

In one embodiment, the first polypeptide chain comprises $VL_A$-CL-$VH_B$-CH1-Fc, and the CL and $VH_B$ of the first polypeptide chain are directly fused together. In another embodiment, the CL and $VH_B$ are linked by an amino acid or an oligopeptide linker. In another embodiment, the first polypeptide chain comprises $VH_B$-CH1-$VL_A$-CL-Fc, and the CH1 and $VL_A$ are directly fused together. In another embodiment, the CH1 and $VL_A$ are linked by an amino acid or an oligopeptide linker. In a further embodiment, the oligo- or poly-peptide linker comprises 1 or more amino acids of any reasonable sequence that provides flexibility. Preferably the linker is selected from the group consisting of G, GS, SG, GGS, GSG, SGG, GGG, GGGS, SGGG, GGGGS, GGGGSGS, GGGGSGS, GGGGSGGS, GGGGSGGGGS, GGGGSGGGGSGGGGS, AKTTPKLEEGEFSEAR, AKTTPKLEEGEFSEARV, AKTTPKLGG, SAKTTP-KLGG, AKTTPKLEEGEFSEARV, SAKTTP, SAKTTP-KLGG, RADAAP, RADAAPTVS, RADAAAAGGPGS, RADAAAA($G_4$S)$_4$, SAKTTP, SAKTTPKLGG, SAKTTP-KLEEGEFSEARV, ADAAP, ADAAPTVSIFPP, TVAAP, TVAAPSVFIFPP, QPKAAP, QPKAAPSVTLFPP, AKTTPP, AKTTPPSVTPLAP, AKTTAP, AKTTAPSVY-PLAP, ASTKGP, ASTKGPSVFPLAP, GENKVEYAPAL-MALS, GPAKELTPLKEAKVS, and GHEAAAVMQVQY-PAS. In one embodiment, the amino acid sequence of the linker may be selected from the group consisting of SEQ ID NOs. 26, 28, and 49-86. In one embodiment, the linker is GSG (SEQ ID NO: 26) or GGGGSGS (SEQ ID NO: 28). The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions. In one embodiment, the binding protein comprises an Fc region. As used herein, the term "Fc region" refers to the C-terminal region of an IgG heavy chain. An example of the amino acid sequence containing the human IgG1 Fc region is SEQ ID NO: 20. The Fc region of an IgG comprises two constant domains, CH2 and CH3.

In one embodiment, the Fc region is a variant Fc region. In one embodiment, the variant Fc region has one or more amino acid modifications, such as substitutions, deletions, or insertions, relative to the parent Fc region. In a further embodiment, amino acid modifications of the Fc region alter the effector function activity relative to the parent Fc region activity. For example, in one embodiment, the variant Fc region may have altered (i.e., increased or decreased) antibody-dependent cytotoxicity (ADCC), complement-mediated cytotoxicity (CDC), phagocytosis, opsonization, or cell binding. In another embodiment, amino acid modifications of the Fc region may alter (i.e., increase or decrease) the affinity of the variant Fc region for an FcγR relative to the parent Fc region. For example, the variant Fc region may alter the affinity for FcγRI, FcγRII, FcγRIII.

In one preferred embodiment, the binding proteins provided herein are capable of binding one or more targets. In one embodiment, the target is selected from the group consisting of cytokines, cell surface proteins, enzymes and receptors. Preferably the binding protein is capable of modulating a biological function of one or more targets. More preferably the binding protein is capable of neutralizing one or more targets.

In one embodiment, the binding protein of the invention is capable of binding cytokines selected from the group consisting of lymphokines, monokines, and polypeptide hormones. In a further embodiment, the binding protein is capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2.

In another embodiment, the binding protein of the invention is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, VEGF and EGFR, HGF and VEGF, VEGF and VEGF (same or a different epitope), VEGF and Ang2, EGFR and cMet, PDGF and VEGF, VEGF and DLL-4, OX40 and PD-L1, ICOS and PD-1, ICOS and PD-L1, Lag-3 and PD-1, Lag-3 and PD-L1, Lag-3 and CTLA-4, ICOS and CTLA-4, CD138 and CD20; CD138 and CD40; CD19 and CD20; CD20 and CD3; CD3 and CD33; CD3 and CD133; CD38 & CD138; CD38 and CD20; CD20 and CD22; CD38 and CD40; CD40 and CD20; CD47 and CD20, CD-8 and IL-6; CSPGs and RGM A; CTLA-4 and BTNO2; CTLA-4 and PD-1; IGF1 and IGF2; IGF1/2 and Erb2B; IGF-1R and EGFR; EGFR and CD13; IGF-1R and ErbB3; EGFR-2 and IGFR; Her2 and Her2 (same or a different epitope); Factor IXa, Factor X, VEGFR-2 and Met; VEGF-A and Angiopoietin-2 (Ang-2); IL-12 and TWEAK; IL-13 and IL-1beta; MAG and RGM A; NgR and RGM A; NogoA and RGM A; OMGp and RGM A; PDL-1 and CTLA-4; PD-1 and TIM-3; RGM A and RGM B; Te38 and TNFα; TNFα and Blys; TNFα and CD-22; TNFα and CTLA-4 domain; TNFα and GP130; TNFα and IL-12p40; and TNFα and RANK ligand.

In one embodiment, the binding protein is capable of binding human IL-17 and human IL-20. In a further embodiment, the binding protein is capable of binding human IL-17 and human IL-20 and comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; a polypeptide chain #2 sequence that is about 65%, about 70%, about 75%, about 80%, about 85%, about 90%, about 95%, about 99%, or 100% identical to SEQ ID NO. 21; and a polypeptide chain #3 sequence that is about 65%, about 70%, about 75%, about 80%, about 85%, about 90%, about 95%, about 99%, or 100% identical to SEQ ID NO. 23. In another embodiment, the binding protein is capable of binding human IL-17 and human IL-20 and comprises FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; and a polypeptide chain #4 that is about 65%, about 70%, about 75%, about 80%, about 85%, about 90%, about 95%, about 99%, or 100% identical to a sequence selected from the group consisting of SEQ ID NO. 29, 30, and 31.

In one embodiment, the binding protein is capable of binding human CD3 and human CD20. In a further embodiment, the binding protein comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 41 and 48; a polypeptide chain #2 sequence that is about 65%, about 70%, about 75%, about 80%, about 85%, about 90%, about 95%, about 99%, or 100% identical to SEQ ID NO. 44; and a polypeptide chain #3 sequence that is about 65%, about 70%, about 75%, about 80%, about 85%, about 90%, about 95%, about 99%, or 100% identical to SEQ ID NO. 46.

In one embodiment, the binding protein is capable of binding human IL-17 and human TNF. In a further embodiment, the binding protein is capable of binding human IL-17 and human TNF and comprises a FIT-Ig polypeptide chain #1 sequence that is about 65%, about 70%, about 75%, about 80%, about 85%, about 90%, about 95%, about 99%, or 100% identical to SEQ ID NO. 87; a polypeptide chain #2 sequence that is about 65%, about 70%, about 75%, about 80%, about 85%, about 90%, about 95%, about 99%, or 100% identical to SEQ ID NO. 89; and a polypeptide chain #3 sequence that is about 65%, about 70%, about 75%, about 80%, about 85%, about 90%, about 95%, about 99%, or 100% identical to SEQ ID NO. 91.

In one embodiment, the binding protein is capable of binding human CTLA-4 and human PD-1. In a further embodiment, the binding protein is capable of binding human CTLA-4 and human PD-1 and comprises a FIT-Ig polypeptide chain #1 sequence that is about 65%, about 70%, about 75%, about 80%, about 85%, about 90%, about 95%, about 99%, or 100% identical to SEQ ID NO. 92 a polypeptide chain #2 sequence that is about 65%, about 70%, about 75%, about 80%, about 85%, about 90%, about 95%, about 99%, or 100% identical to SEQ ID NO. 95; and a polypeptide chain #3 sequence that is about 65%, about 70%, about 75%, about 80%, about 85%, about 90%, about 95%, about 99%, or 100% identical to SEQ ID NO. 97.

In another embodiment, the binding protein of the invention is capable of binding one or two cytokines, cytokine-related proteins, and cytokine receptors selected from the group consisting of BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, FGER1, FGFR2, FGFR3, EGFR, ROR1, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, FIGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

The binding protein of the invention is capable of binding one or more chemokines, chemokine receptors, and chemokine-related proteins selected from the group consisting of CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL.

In another embodiment, the binding protein of the invention is capable of binding cell surface protein such as, for example, integrins. In another embodiment, the binding protein of the invention is capable of binding enzymes selected from the group consisting of kinases and proteases. In yet another embodiment, the binding protein of the invention is capable of binding receptors selected from the group consisting of lymphokine receptors, monokine receptors, and polypeptide hormone receptors.

In one embodiment, the binding protein is multivalent. In another embodiment, the binding protein is multispecific. The multivalent and or multispecific binding proteins described above have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist antibody; and/or (3) induce cell death and/or apoptosis of a cell expressing an antigen which the multivalent antibody is capable of binding to. The "parent antibody" which provides at least one antigen binding specificity of the multivalent and or multispecific binding proteins may be one which is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may be endowed with them when constructed as a multivalent binding protein as herein described.

In another embodiment the binding protein of the invention has an on rate constant (Kon) to one or more targets selected from the group consisting of: at least about $10^2 M^{-1} s^{-1}$; at least about $10^3 M^{-1} s^{-1}$; at least about $10^4 M^{-1} s^{-1}$; at least about $10^5 M^{-1} s^{-1}$; and at least about $10^6 M^{-1} s^{-1}$, as measured by surface plasmon resonance. Preferably, the binding protein of the invention has an on rate constant (Kon) to one or more targets between $10^2 M^{-1} s^{-1}$ to $10^3 M^{-1} s^{-1}$; between $10^3 M^{-1} s^{-1}$ to $10^4 M^{-1} s^{-1}$; between $10^4 M^{-1} s^{-1}$ to $10^5 M^{-1} s^{-1}$; or between $10^5 M^{-1} s^{-1}$ to $10^6 M^{-1} s^{-1}$; as measured by surface plasmon resonance.

In another embodiment the binding protein has an off rate constant (Koff) for one or more targets selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance. Preferably, the binding protein of the invention has an off rate constant (Koff) to one or more targets of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance.

In another embodiment the binding protein has a dissociation constant ($K_D$) to one or more targets selected from the group consisting of: at most about $10^{-7}$ M; at most about $10^{-8}$ M; at most about $10^{-9}$ M; at most about $10^{-10}$; at most about $10^{-11}$ M; at most about $10^{-12}$ M; and at most $10^{-13}$ M. Preferably, the binding protein of the invention has a dissociation constant ($K_D$) to IL-12 or IL-23 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ M to $10^{-13}$ M.

In another embodiment, the binding protein described above is a conjugate further comprising an agent selected from the group consisting of an immunoadhesion molecule, an imaging agent, a therapeutic agent, and a cytotoxic agent. In one embodiment, the imaging agent is selected from the group consisting of a radiolabel, an enzyme, a fluorescent label, a luminescent label, a bioluminescent label, a magnetic label, and biotin. In a further embodiment, the imaging agent is a radiolabel selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$. In one embodiment, the therapeutic or cytotoxic agent is selected from the group consisting of an immunosuppressive agent, an immuno-stimulatory agent, an antimetabolite, an alkylating agent, an antibiotic, a growth factor, a cytokine, an anti-angiogenic agent, an anti-mitotic agent, an anthracycline, a toxin, and an apoptotic agent. In one embodiment, the binding protein is conjugated directly to the agent. In another embodiment, the binding protein is conjugated to the agent via a linker. Suitable linkers include, but are not limited to, amino acid and polypeptide linkers disclosed herein. Linkers may be cleavable or non-cleavable.

In another embodiment the binding protein described above is a crystallized binding protein and exists as a crystal. Preferably the crystal is a carrier-free pharmaceutical controlled release crystal. More preferably the crystallized binding protein has a greater half life in vivo than the soluble counterpart of said binding protein. Most preferably the crystallized binding protein retains biological activity.

In another embodiment the binding protein described above is glycosylated. Preferably, the glycosylation is a human glycosylation pattern.

One aspect of the invention pertains to an isolated nucleic acid encoding any one of the binding protein disclosed above. A further embodiment provides a vector comprising the isolated nucleic acid disclosed above wherein said vector is selected from the group consisting of pcDNA; pTT (Durocher et al., *Nucleic Acids Research* 2002, Vol 30, No. 2); pTT3 (pTT with additional multiple cloning site; pEF-BOS (Mizushima, S. and Nagata, S., (1990) *Nucleic acids Research* Vol 18, No. 17); pBV; pJV; pcDNA3.1 TOPO, pEF6 TOPO and pBJ. The multi-specific binding proteins and methods of making the same are provided. The binding protein can be generated using various techniques. Expression vectors, host cells and methods of generating the binding proteins are provided in this disclosure.

The antigen-binding variable domains of the binding proteins of this disclosure can be obtained from parent binding proteins, including polyclonal Abs, monoclonal Abs, and or receptors capable of binding antigens of interest. These parent binding proteins may be naturally occurring or may be generated by recombinant technology. The person of ordinary skill in the art is well familiar with many methods for producing antibodies and/or isolated receptors, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques. The binding variable domains of the binding proteins can also be obtained from isolated receptor molecules obtained by extraction procedures known in the art (e.g., using solvents, detergents, and/or affinity purifications), or determined by biophysical methods known in the art (e.g., X-ray crystallography, NMR, interferometry, and/or computer modeling).

An embodiment is provided comprising selecting parent binding proteins with at least one or more properties desired in the binding protein molecule. In an embodiment, the desired property is one or more of those used to characterize antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

The multi-specific antibodies may also be designed such that one or more of the antigen binding domain are rendered non-functional. The variable domains may be obtained using recombinant DNA techniques from parent binding proteins generated by any one of the methods described herein. In an embodiment, a variable domain is a murine heavy or light chain variable domain. In another embodiment, a variable domain is a CDR grafted or a humanized variable heavy or light chain domain. In an embodiment, a variable domain is a human heavy or light chain variable domain.

In an embodiment, one or more constant domains are linked to the variable domains using recombinant DNA techniques. In an embodiment, a sequence comprising one or more heavy chain variable domains is linked to a heavy chain constant domain and a sequence comprising one or more light chain variable domains is linked to a light chain constant domain. In an embodiment, the constant domains are human heavy chain constant domains and human light chain constant domains, respectively. In an embodiment, the heavy chain is further linked to an Fc region. The Fc region may be a native sequence Fc region or a variant Fc region. In another embodiment, the Fc region is a human Fc region. In another embodiment, the Fc region includes Fc region from IgG1, IgG2, IgG3, IgG4, IgA, IgM, IgE, or IgD.

Additionally, the binding proteins provided herein can be employed for tissue-specific delivery (target a tissue marker and a disease mediator for enhanced local PK thus higher efficacy and/or lower toxicity), including intracellular delivery (targeting an internalizing receptor and an intracellular molecule), delivering to inside brain (targeting transferrin receptor and a CNS disease mediator for crossing the blood-brain barrier). The binding proteins can also serve as a carrier protein to deliver an antigen to a specific location via binding to a non-neutralizing epitope of that antigen and also to increase the half-life of the antigen. Furthermore, the binding proteins can be designed to either be physically linked to medical devices implanted into patients or target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397). Directing appropriate types of cell to the site of medical implant may promote healing and restoring normal tissue function. Alternatively, inhibition of mediators (including but not limited to cytokines), released upon device implantation by a receptor antibody fusion protein coupled to or target to a device is also provided.

In one aspect, a host cell is transformed with the vector disclosed above. In one embodiment, the host cell is a prokaryotic cell. In a further embodiment, the host cell is *Escherichia coli*. In another embodiment, the host cell is an eukaryotic cell. In a further embodiment, the eukaryotic cell is selected from the group consisting of protist cell, animal cell, plant cell and fungal cell. In one embodiment, the host cell is a mammalian cell including, but not limited to, 293, COS, NS0, and CHO and; or a fungal cell such as *Saccharomyces cerevisiae*; or an insect cell such as Sf9.

Another aspect of the invention provides a method of producing a binding protein disclosed above comprising culturing any one of the host cells also disclosed above in a culture medium under conditions sufficient to produce the binding protein. Preferably 50%-75% of the binding protein produced by this method is a dual specific tetravalent binding protein. More preferably 75%-90% of the binding protein produced by this method is a dual specific tetravalent binding protein. Most preferably 90%-95% of the binding protein produced is a dual specific tetravalent binding protein.

Another embodiment provides a binding protein produced according to the method disclosed above.

One embodiment provides a composition for the release of a binding protein wherein the composition comprises a formulation which in turn comprises a crystallized binding protein, as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutyrate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, as disclosed above and a pharmaceutically acceptable carrier. Pharmaceutically acceptable carriers include, but are not limited to, phosphate buffer or saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (e.g., glycerol, propylene glycol, and liquid polyethylene glycol, and the like), and suitable mixtures thereof. In some cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In a further embodiment the pharmaceutical composition comprises at least one additional therapeutic agent for treating a disorder. In one embodiment, the additional agent is selected from the group consisting of: therapeutic agents, imaging agents, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-PD-1, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for treating a human subject suffering from a disorder in which the target, or targets, capable of being bound by the binding protein disclosed above is detrimental, comprising administering to the human subject a binding protein disclosed above such that the activity of the target or targets in the human subject is inhibited and treatment or preventions of the disorder is achieved. In one embodiment, the disease or disorder is an inflammatory condition, autoimmune disease, or cancer. In one embodiment, the disease or disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, *chlamydia, Yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatitis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi. system disorder, mixed connective tissue disease, monoclonal gammopathy, multiple myeloma, multiple systems degenerations (Mencel Dejerine-Thomas Shi-Drager and Machado-Joseph), myasthenia gravis, *Mycobacterium avium intracellulare, Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue.

In another aspect the invention provides a method of treating a patient suffering from a disorder comprising the step of administering any one of the binding proteins disclosed above before, concurrent, or after the administration of a second agent, as discussed above. In a preferred embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

In one embodiment, the pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one anti-idiotype antibody to at least one binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

In another embodiment the binding proteins of the invention are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (I-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP- 2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD47; CD48, CD52; CD69; CD70, CD72; CD74; CD79A; CD79B; CD8; CD80; CD81; CD83; CD86; CD137, CD138, B7-1, B7-2, ICOSL, B7-H3, B7-H4, CD137L, OX40L, CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA-4; CTNNB1 (b-catenin); CTSB (cathepsin B); CX3CL1 (SCYD1); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; ID2; IFN-a; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; PCSK9; P2RX7; PAP; PART1; PATE; PAWR; PCA3; PCNA; PD-1; PD-L1; alpha4beta7, OX40, GITR, TIM-3, Lag-3, B7-H3, B7-H4, GDF8, CGRP, Lingo-1, Factor IXa, Factor X, ICOS, GARP, BTLA, CD160, ROR1, 2B4, KIR, CD27, OX40, CD40L, A2aR, PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STATE; STEAP; STEAP2; TB4R2; TBX21; TCP10; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

Given their ability to bind to two or more antigens, the binding proteins of the present invention can be used to detect the antigens (e.g., in a biological sample, such as serum or plasma), using a conventional immunoassay, such as an enzyme linked immunosorbent assays (ELISA), an radioimmunoassay (RIA) or tissue immunohistochemistry. The FIT-Ig is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, *-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 3H, 14C, 35S, 90Y, 99Tc, 111In, 125I, 131I, 177Lu, 166Ho, or 153Sm.

The binding proteins of the invention, in one embodiment, are capable of neutralizing the activity of the antigens both in vitro and in vivo. Accordingly, such FIT-Igs can be used to inhibit antigen activity, e.g., in a cell culture containing the antigens, in human subjects or in other mammalian subjects having the antigens with which a binding protein of the invention cross-reacts. In another embodiment, the invention provides a method for reducing antigen activity in a subject suffering from a disease or disorder in which the antigen activity is detrimental. A binding protein of the invention can be administered to a human subject for therapeutic purposes.

As used herein, the term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc. of the subject). Non-limiting examples of disorders that can be treated with the binding proteins of the invention include those disorders discussed below and in the section pertaining to pharmaceutical compositions of the antibodies of the invention.

The FIT-Igs of the invention may bind one antigen or multiple antigens. Such antigens include, but are not limited to, the targets listed in the following databases, which databases are incorporated herein by reference. These target databases include, but are not limited to, the following listings:

Therapeutic targets (http://xin.cz3.nus.edu.sg/group/cjttd/ttd.asp);
Cytokines and cytokine receptors (http://www.cytokinewebfacts.com/, http://www.copewithcytokines.de/cope.cgi, and
http://cmbi.bjmu.edu.cn/cmbidata/cgf/CGF_Database/cytokine.medic.kumamotou.acjp/CFC/indexR.html);
Chemokines (http://cytokine.medic.kumamoto-u.acjp/CFC/CK/Chemokine.html);
Chemokine receptors and GPCRs (http://csp.medic.kumamotou.ac.jp/CSP/Receptor.html, http://www.gpcr.org/7tm/);
Olfactory Receptors (http://senselab.med.yale.edu/senselab/ORDB/default.asp);
Receptors (http://www.iuphar-db.org/iuphar-rd/list/index.htm);
Cancer targets (http://cged.hgcjp/cgi-bin/input.cgi);
Secreted proteins as potential antibody targets (http://spd.cbi.pku.edu.cn/);
Protein kinases (http://spd.cbi.pku.edu.cn/), and
Human CD markers (http://content.labvelocity.com/tools/6/1226/CD_table_final_locked.pdf) and (Zola H, 2005 CD molecules 2005: human cell differentiation molecules Blood, 106:3123-6).

FIT-Igs are useful as therapeutic agents to simultaneously block two different targets to enhance efficacy/safety and/or increase patient coverage. Such targets may include soluble targets (IL-13 and TNF) and cell surface receptor targets (VEGFR and EGFR). It can also be used to induce redirected cytotoxicity between tumor cells and T cells (Her2 and CD3) for cancer therapy, or between autoreactive cell and effector cells for autoimmune/transplantation, or between any target cell and effector cell to eliminate disease-causing cells in any given disease.

In addition, FIT-Ig can be used to trigger receptor clustering and activation when it is designed to target two different epitopes on the same receptor. This may have benefit in making agonistic and antagonistic anti-GPCR therapeutics. In this case, FIT-Ig can be used to target two different epitopes on one cell for clustering/signaling (two cell surface molecules) or signaling (on one molecule). Similarly, a FIT-Ig molecule can be designed to trigger CTLA-4 ligation, and a negative signal by targeting two different epitopes (or 2 copies of the same epitope) of CTLA-4 extracellular domain, leading to down regulation of the immune response. CTLA-4 is a clinically validated target for therapeutic treatment of a number of immunological disorders. CTLA-4/B7 interactions negatively regulate T cell activation by attenuating cell cycle progression, IL-2 production, and proliferation of T cells following activation, and CTLA-4 (CD152) engagement can down-regulate T cell activation and promote the induction of immune tolerance. However, the strategy of attenuating T cell activation by agonistic antibody engagement of CTLA-4 has been unsuccessful since CTLA-4 activation requires ligation. The molecular interaction of CTLA-4/B7 is in "skewed zipper" arrays, as demonstrated by crystal structural analysis (Stamper 2001 Nature 410:608). However none of the currently available CTLA-4 binding reagents have ligation properties, including anti-CTLA-4 monoclonal antibodies. There have been several attempts to address this issue. In one case, a cell member-bound single chain antibody was generated, and significantly inhibited allogeneic rejection in mice (Hwang 2002 JI 169:633). In a separate case, artificial APC surface-linked single-chain antibody to CTLA-4 was generated and demonstrated to attenuate T cell responses (Griffin 2000 JI 164:4433). In both cases, CTLA-4 ligation was achieved by closely localized member-bound antibodies in artificial systems. While these experiments provide proof-of-concept for immune down-regulation by triggering CTLA-4 negative signaling, the reagents used in these reports are not suitable for therapeutic use. To this end, CTLA-4 ligation may be achieved by using a FIT-Ig molecule, which target two different epitopes (or 2 copies of the same epitope) of CTLA-4 extracellular domain. The rationale is that the distance spanning two binding sites of an IgG, approximately 150-170 Å, is too large for active ligation of CTLA-4 (30-50 Å between 2 CTLA-4 homodimer). However the distance between the two binding sites on FIT-Ig (one arm) is much shorter, also in the range of 30-50 Å, allowing proper ligation of CTLA-4.

Similarly, FIT-Ig can target two different members of a cell surface receptor complex (e.g. IL-12R alpha and beta). Furthermore, FIT-Ig can target CR1 and a soluble protein/pathogen to drive rapid clearance of the target soluble protein/pathogen.

Additionally, FIT-Igs of the invention can be employed for tissue-specific delivery (target a tissue marker and a disease mediator for enhanced local PK thus higher efficacy and/or lower toxicity), including intracellular delivery (targeting an internalizing receptor and a intracellular molecule), delivering to inside brain (targeting transferrin receptor and a CNS disease mediator for crossing the blood-brain barrier). FIT-Ig can also serve as a carrier protein to deliver an antigen to a specific location via biding to a non-neutralizing epitope of that antigen and also to increase the half-life of the antigen. Furthermore, FIT-Ig can be designed to either be physically linked to medical devices implanted into patients or target these medical devices (Burke, Sandra E.; Kuntz, Richard E.; Schwartz, Lewis B. Zotarolimus (ABT-578) eluting stents. Advanced Drug Delivery Reviews (2006), 58(3), 437-446; Surface coatings for biological activation and functionalization of medical devices. Hildebrand, H. F.; Blanchemain, N.; Mayer, G.; Chai, F.; Lefebvre, M.; Boschin, F. Surface and Coatings Technology (2006), 200(22-23), 6318-6324; Drug/device combinations for local drug therapies and infection prophylaxis. Wu, Peng; Grainger, David W. Biomaterials (2006), 27(11), 2450-2467; Mediation of the cytokine network in the implantation of orthopedic devices. Marques, A. P.; Hunt, J. A.; Reis, Rui L. Biodegradable Systems in Tissue Engineering and Regenerative Medicine (2005), 377-397; Page: 52

Mediation of the cytokine network in the implantation of orthopedic devices. Marques, A. P.; Hunt, J. A.; Reis, Rui L. Biodegradable Systems in Tissue Engineering and Regenerative Medicine (2005), 377-397.) Briefly, directing appropriate types of cell to the site of medical implant may promote healing and restoring normal tissue function. Alternatively, inhibition of mediators (including but not limited to cytokines), released upon device implantation by a FIT-Ig coupled to or target to a device is also provided. For example, Stents have been used for years in interventional cardiology to clear blocked arteries and to improve the flow of blood to the heart muscle. However, traditional bare metal stents have been known to cause restenosis (re-narrowing of the artery in a treated area) in some patients and can lead to blood clots. Recently, an anti-CD34 antibody coated stent has been described which reduced restenosis and prevents blood clots from occurring by capturing endothelial progenitor cells (EPC) circulating throughout the blood. Endothelial cells are cells that line blood vessels, allowing blood to flow smoothly. The EPCs adhere to the hard surface of the stent forming a smooth layer that not only promotes healing but prevents restenosis and blood clots, complications previously associated with the use of stents (Aoji et al. 2005 J Am Coll Cardiol. 45(10):1574-9). In addition to improving outcomes for patients requiring stents, there are also implications for patients requiring cardiovascular bypass surgery. For example, a prosthetic vascular conduit (artificial artery) coated with anti-EPC antibodies would eliminate the need to use arteries from patients legs or arms for bypass surgery grafts. This would reduce surgery and anesthesia times, which in turn will reduce coronary surgery deaths. FIT-Ig are designed in such a way that it binds to a cell surface marker (such as CD34) as well as a protein (or an epitope of any kind, including but not limited to lipids and polysaccharides) that has been coated on the implanted device to facilitate the cell recruitment. Such approaches can also be applied to other medical implants in general. Alternatively, FIT-Igs can be coated on medical devices and upon implantation and releasing all FITs from the device (or any other need which may require additional fresh FIT-Ig, including aging and denaturation of the already loaded FIT-Ig) the device could be reloaded by systemic administration of fresh FIT-Ig to the patient, where the FIT-Ig is designed to binds to a target of interest (a cytokine, a cell surface marker (such as CD34) etc.) with one set of binding sites and to a target coated on the device (including a protein, an epitope of any kind, including but not limited to lipids, polysaccharides and polymers) with the other. This technology has the advantage of extending the usefulness of coated implants.

FIT-Ig molecules of the invention are also useful as therapeutic molecules to treat various diseases. Such FIT-Ig molecules may bind one or more targets involved in a specific disease. Examples of such targets in various diseases are described below.

Many proteins have been implicated in general autoimmune and inflammatory responses, including C5, CCL1 (I-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA-4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFBI, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144). FIT-Igs capable of binding one or more of the targets listed above are also contemplated.

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. It is now widely accepted that airway inflammation is the key factor underlying the pathogenesis of asthma, involving a complex interplay of inflammatory cells such as T cells, B cells, eosinophils, mast cells and macrophages, and of their secreted mediators including cytokines and chemokines Corticosteroids are the most important anti-inflammatory treatment for asthma today, however their mechanism of action is non-specific and safety concerns exist, especially in the juvenile patient population. The development of more specific and targeted therapies is therefore warranted. There is increasing evidence that IL-13 in mice mimics many of the features of asthma, including AHR, mucus hypersecretion and airway fibrosis, independently of eosinophilic inflammation (Finotto et al., International Immunology (2005), 17(8), 993-1007; Padilla et al., Journal of Immunology (2005), 174(12), 8097-8105).

IL-13 has been implicated as having a pivotal role in causing pathological responses associated with asthma. The development of anti-IL-13 monoclonal antibody therapy to reduce the effects of IL-13 in the lung is an exciting new approach that offers considerable promise as a novel treatment for asthma. However other mediators of differential immunological pathways are also involved in asthma pathogenesis, and blocking these mediators, in addition to IL-13, may offer additional therapeutic benefit. Such target pairs include, but are not limited to, IL-13 and a pro-inflammatory cytokine, such as tumor necrosis factor-α (TNF-α). TNF-α may amplify the inflammatory response in asthma and may be linked to disease severity (McDonnell, et al., Progress in Respiratory Research (2001), 31(New Drugs for Asthma, Allergy and COPD), 247-250.). This suggests that blocking both IL-13 and TNF-α may have beneficial effects, particularly in severe airway disease. In a preferred embodiment the FIT-Ig of the invention binds the targets IL-13 and TNFα and is used for treating asthma.

Animal models such as OVA-induced asthma mouse model, where both inflammation and AHR can be assessed, are known in the art and may be used to determine the ability of various FIT-Ig molecules to treat asthma. Animal models for studying asthma are disclosed in Coffman, et al., Journal of Experimental Medicine (2005), 201(12), 1875-1879; Lloyd, et al., Advances in Immunology (2001), 77, 263-295; Boyce et al., Journal of Experimental Medicine (2005), 201(12), 1869-1873; and Snibson, et al., Journal of the British Society for Allergy and Clinical Immunology (2005), 35(2), 146-52. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257).

Based on the rationale disclosed above and using the same evaluation model for efficacy and safety other pairs of targets that FIT-Ig molecules can bind and be useful to treat asthma may be determined. Preferably such targets include, but are not limited to, IL-13 and IL-1beta, since IL-1beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; and IL-13 and ADAM8. The present invention also contemplates FIT-Igs capable of binding one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STATE, TBX21, TGFB1, TNFSF6, YY1, CYSLTR1, FCER1A, FCER2, LTB4R, TB4R2, LTBR, and Chitinase.

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines including TNF, chemokines, and growth factors are expressed in diseased joints. Systemic administration of anti-TNF antibody or sTNFR fusion protein to mouse models of RA was shown to be anti-inflammatory and joint protective. Clinical investigations in which the activity of TNF in RA patients was blocked with intravenously administered infliximab (Harriman G, Harper L K, Schaible T F. 1999 Summary of clinical trials in rheumatoid arthritis using infliximab, an anti-TNFalpha treatment. Ann Rheum Dis 58 Suppl 1:161-4.), a chimeric anti-TNF monoclonal antibody (mAB), has provided evidence that TNF regulates IL-6, IL-8, MCP-1, and VEGF production, recruitment of immune and inflammatory cells into joints, angiogenesis, and reduction of blood levels of matrix metalloproteinases-1 and -3. A better understanding of the inflammatory pathway in rheumatoid arthritis has led to identification of other therapeutic targets involved in rheumatoid arthritis. Promising treatments such as interleukin-6 antagonists (MRA), CTLA4Ig (abatacept, Genovese Mc et al 2005 Abatacept for rheumatoid arthritis refractory to tumor necrosis factor alpha inhibition. N Engl J Med. 353:1114-23.), and anti-B cell therapy (rituximab, Okamoto H, Kamatani N. 2004 Rituximab for rheumatoid arthritis. N Engl J Med. 351:1909) have already been tested in randomized controlled trials over the past year. Other cytokines have been identified and have been shown to be of benefit in animal models, including interleukin-15, interleukin-17, and interleukin-18, and clinical trials of these agents are currently under way. Dual-specific antibody therapy, combining anti-TNF and another mediator, has great potential in enhancing clinical efficacy and/or patient coverage. For example, blocking both TNF and VEGF can potentially eradicate inflammation and angiogenesis, both of which are involved in pathophysiology of RA. Blocking other pairs of targets involved in RA including, but not limited to, TNF and IL-18; TNF and IL-12; TNF and IL-23; TNF and IL-1beta; TNF and MIF; TNF and IL-17; and TNF and IL-15 with specific FIT-Ig Igs is also contemplated. In addition to routine safety assessments of these target pairs, specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257). Whether a FIT-Ig Ig molecule will be useful for the treatment of rheumatoid arthritis can be assessed using preclinical animal RA models such as the collagen-induced arthritis mouse model. Other useful models are also well known in the art (see Brand D D., Comp Med. (2005) 55(2):114-22).

The immunopathogenic hallmark of systemic lupus erythematosus (SLE) is the polyclonal B cell activation, which leads to hyperglobulinemia, autoantibody production and immune complex formation. The fundamental abnormality appears to be the failure of T cells to suppress the forbidden B cell clones due to generalized T cell dysregulation. In addition, B and T-cell interaction is facilitated by several cytokines such as IL-10 as well as co-stimulatory molecules such as CD40 and CD40L, B7 and CD28 and CTLA-4, which initiate the second signal. These interactions together with impaired phagocytic clearance of immune complexes and apoptotic material, perpetuate the immune response with resultant tissue injury. The following targets may be involved in SLE and can potentially be used for FIT-Ig approach for therapeutic intervention: B cell targeted therapies: CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGS1, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, IL1R2, ITGA2, ITGA3, MS4A1, ST6GAL1, CD1C, CHST10, HLA-A, HLA-DRA, and NT5E.; co-stimulatory signals: CTLA-4 or B7.1/B7.2; inhibition of B cell survival: BlyS, BAFF; Complement inactivation: C5; Cytokine modulation: the key principle is that the net biologic response in any tissue is the result of a balance between local levels of proinflammatory or anti-inflammatory cytokines (see Sfikakis P P et al 2005 Curr Opin Rheumatol 17:550-7). SLE is considered to be a Th-2 driven disease with documented elevations in serum IL-4, IL-6, IL-10. FIT-Ig Igs capable of binding one or more targets selected from the group consisting of IL-4, IL-6, IL-10, IFN-a, and TNF-a are also contemplated. Combination of targets discussed above will enhance therapeutic efficacy for SLE which can be tested in a number of lupus preclinical models (see Peng S L (2004) Methods Mol Med.; 102:227-72).

Multiple sclerosis (MS) is a complex human autoimmune-type disease with a predominantly unknown etiology. Immunologic destruction of myelin basic protein (MBP) throughout the nervous system is the major pathology of multiple sclerosis. MS is a disease of complex pathologies, which involves infiltration by CD4+ and CD8+ T cells and of response within the central nervous system. Expression in the CNS of cytokines, reactive nitrogen species and costimulator molecules have all been described in MS. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification.

IL-12 is a proinflammatory cytokine that is produced by APC and promotes differentiation of Th1 effector cells. IL-12 is produced in the developing lesions of patients with MS as well as in EAE-affected animals. Previously it was shown that interference in IL-12 pathways effectively prevents EAE in rodents, and that in vivo neutralization of IL-12p40 using a anti-IL-12 mAb has beneficial effects in the myelin-induced EAE model in common marmosets.

TWEAK is a member of the TNF family, constitutively expressed in the central nervous system (CNS), with pro-inflammatory, proliferative or apoptotic effects depending upon cell types. Its receptor, Fn14, is expressed in CNS by endothelial cells, reactive astrocytes and neurons. TWEAK and Fn14 mRNA expression increased in spinal cord during experimental autoimmune encephalomyelitis (EAE). Anti-TWEAK antibody treatment in myelin oligodendrocyte glycoprotein (MOG) induced EAE in C57BL/6 mice resulted in a reduction of disease severity and leukocyte infiltration when mice were treated after the priming phase.

One aspect of the invention pertains to FIT-Ig Ig molecules capable of binding one or more, preferably two, targets selected from the group consisting of IL-12, TWEAK, IL-23, CXCL13, CD40, CD40L, IL-18, VEGF, VLA-4, TNF, CD45RB, CD200, IFNgamma, GM-CSF, FGF, C5, CD52, and CCR2. A preferred embodiment includes a dual-specific anti-IL-12/TWEAK FIT-Ig Ig as a therapeutic agent beneficial for the treatment of MS. Several animal models for assessing the usefulness of the FIT-Ig molecules to treat MS are known in the art (see Steinman L, et al., (2005) Trends Immunol. 26(11):565-71; Lublin F D., et al., (1985) Springer Semin Immunopathol. 8(3):197-208; Genain C P, et al., (1997) J Mol Med. 75(3):187-97; Tuohy V K, et al., (1999) J Exp Med. 189(7):1033-42; Owens T, et al., (1995) Neurol Clin. 13(1):51-73; and 't Hart B A, et al., (2005) J Immunol 175(7):4761-8. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Jones R. 2000 Rovelizumab (ICOS Corp). IDrugs. 3 (4):442-6).

The pathophysiology of sepsis is initiated by the outer membrane components of both gram-negative organisms (lipopolysaccharide [LPS], lipid A, endotoxin) and gram-positive organisms (lipoteichoic acid, peptidoglycan). These outer membrane components are able to bind to the CD14 receptor on the surface of monocytes. By virtue of the recently described toll-like receptors, a signal is then transmitted to the cell, leading to the eventual production of the proinflammatory cytokines tumor necrosis factor-alpha (TNF-alpha) and interleukin-1 (IL-I). Overwhelming inflammatory and immune responses are essential features of septic shock and play a central part in the pathogenesis of tissue damage, multiple organ failure, and death induced by sepsis. Cytokines, especially tumor necrosis factor (TNF) and interleukin (IL)-1, have been shown to be critical mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity.

The treatment of sepsis and septic shock remains a clinical conundrum, and recent prospective trials with biological response modifiers (i.e. anti-TNF, anti-MIF) aimed at the inflammatory response have shown only modest clinical benefit. Recently, interest has shifted toward therapies aimed at reversing the accompanying periods of immune suppression. Studies in experimental animals and critically ill patients have demonstrated that increased apoptosis of lymphoid organs and some parenchymal tissues contribute to this immune suppression, anergy, and organ system dysfunction. During sepsis syndromes, lymphocyte apoptosis can be triggered by the absence of IL-2 or by the release of glucocorticoids, granzymes, or the so-called 'death' cytokines tumor necrosis factor alpha or Fas ligand. Apoptosis proceeds via auto-activation of cytosolic and/or mitochondrial caspases, which can be influenced by the pro- and anti-apoptotic members of the Bcl-2 family. In experimental animals, not only can treatment with inhibitors of apoptosis prevent lymphoid cell apoptosis; it may also improve outcome. Although clinical trials with anti-apoptotic agents remain distant due in large part to technical difficulties associated with their administration and tissue targeting, inhibition of lymphocyte apoptosis represents an attractive therapeutic target for the septic patient. Likewise, a dual-specific agent targeting both inflammatory mediator and a apoptotic mediator, may have added benefit. One aspect of the invention pertains to FIT-Ig Igs capable of binding one or more targets involved in sepsis, preferably two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL10, IL1B, NFKB1, PROC, TNFRSF1A, CSF3, IL10, IL1B, IL6, ADORA2A, CCR3, IL10, IL1B, IL1RN, MIF, NFKB1, PTAFR, TLR2, TLR4, GPR44, HMOX1, midkine, IRAK1, NFKB2, SERPINA1, SERPINE1, and TREM1. The efficacy of such FIT-Ig Igs for sepsis can be assessed in preclinical animal models known in the art (see Buras J A, et al., (2005) Nat Rev Drug Discov. 4(10):854-65 and Calandra T, et al., (2000) Nat Med. 6(2):164-70).

Chronic neurodegenerative diseases are usually age-dependent diseases characterized by progressive loss of neuronal functions (neuronal cell death, demyelination), loss of mobility and loss of memory. Emerging knowledge of the mechanisms underlying chronic neurodegenerative diseases (e g Alzheimer's disease) show a complex etiology and a variety of factors have been recognized to contribute to their development and progression e.g. age, glycemic status, amyloid production and multimerization, accumulation of advanced glycation-end products (AGE) which bind to their receptor RAGE (receptor for AGE), increased brain oxidative stress, decreased cerebral blood flow, neuroinflammation including release of inflammatory cytokines and chemokines, neuronal dysfunction and microglial activation. Thus these chronic neurodegenerative diseases represent a complex interaction between multiple cell types and mediators. Treatment strategies for such diseases are limited and mostly constitute either blocking inflammatory processes with non-specific anti-inflammatory agents (e.g., corticosteroids, COX inhibitors) or agents to prevent neuron loss and/or synaptic functions. These treatments fail to stop disease progression. Recent studies suggest that more targeted therapies such as antibodies to soluble A-β peptide (including the A-b oligomeric forms) can not only help stop disease progression but may help maintain memory as well. These preliminary observations suggest that specific therapies targeting more than one disease mediator (e.g. A-β and a pro-inflammatory cytokine such as TNF) may provide even better therapeutic efficacy for chronic neurodegenerative diseases than observed with targeting a single disease mechanism (e.g. soluble A-β alone) (see C. E. Shepherd, et al, Neurobiol Aging. 2005 Oct. 24; Nelson R B., Curr Pharm Des. 2005; 11:3335; William L. Klein.; Neurochem Int. 2002; 41:345; Michelle C Janelsins, et al., J Neuroinflammation. 2005; 2:23; Soloman B., Curr Alzheimer Res. 2004; 1:149; Igor Klyubin, et al., Nat Med. 2005; 11:556-61; Arancio O, et al., EMBO Journal (2004) 1-10; Bornemann K D, et al., Am J Pathol. 2001; 158:63; Deane R, et al., Nat Med. 2003; 9:907-13; and Eliezer Masliah, et al., Neuron. 2005; 46:857).

The FIT-Ig molecules of the invention can bind one or more targets involved in Chronic neurodegenerative diseases such as Alzheimer's. Such targets include, but are not limited to, any mediator, soluble or cell surface, implicated in AD pathogenesis e.g. AGE (S100 A, amphoterin), pro-inflammatory cytokines (e.g. IL-1), chemokines (e.g. MCP 1), molecules that inhibit nerve regeneration (e.g. Nogo, RGM A), molecules that enhance neurite growth (neurotrophins) The efficacy of FIT-Ig molecules can be validated in pre-clinical animal models such as the transgenic mice that over-express amyloid precursor protein or RAGE and develop Alzheimer's disease-like symptoms. In addition, FIT-Ig molecules can be constructed and tested for efficacy in the animal models and the best therapeutic FIT-Ig can be selected for testing in human patients. FIT-Ig molecules can also be employed for treatment of other neurodegenerative diseases such as Parkinson's disease. Alpha-Synuclein is involved in Parkinson's pathology. A FIT-Ig capable of targeting alpha-synuclein and inflammatory mediators such as TNF, IL-1, MCP-1 can prove effective therapy for Parkinson's disease and are contemplated in the invention.

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g. cytokines and chemokines) that worsen the initial injury and result in significant enlargement of the lesion area, sometimes more than 10-fold. These primary and secondary mechanisms in SCI are very similar to those in brain injury caused by other means e.g. stroke. No satisfying treatment exists and high dose bolus injection of methylprednisolone (MP) is the only used therapy within a narrow time window of 8 h post injury. This treatment, however, is only intended to prevent secondary injury without causing any significant functional recovery. It is heavily criticized for the lack of unequivocal efficacy and severe adverse effects, like immunosuppression with subsequent infections and severe histopathological muscle alterations. No other drugs, biologics or small molecules, stimulating the endogenous regenerative potential are approved, but promising treatment principles and drug candidates have shown efficacy in animal models of SCI in recent years. To a large extent the lack of functional recovery in human SCI is caused by factors inhibiting neurite growth, at lesion sites, in scar tissue, in myelin as well as on injury-associated cells. Such factors are the myelin-associated proteins NogoA, OMgp and MAG, RGM A, the scar-associated CSPG (Chondroitin Sulfate Proteoglycans) and inhibitory factors on reactive astrocytes (some semaphorins and ephrins). However, at the lesion site not only growth inhibitory molecules are found but also neurite growth stimulating factors like neurotrophins, laminin, L1 and others. This ensemble of neurite growth inhibitory and growth promoting molecules may explain that blocking single factors, like NogoA or RGM A, resulted in significant functional recovery in rodent SCI models, because a reduction of the inhibitory influences could shift the balance from growth inhibition to growth promotion. However, recoveries observed with blocking a single neurite outgrowth inhibitory molecule were not complete. To achieve faster and more pronounced recoveries either blocking two neurite outgrowth inhibitory molecules e.g. Nogo and RGM A, or blocking an neurite outgrowth inhibitory molecule and enhancing functions of a neurite outgrowth enhancing molecule e.g. Nogo and neurotrophins, or blocking a neurite outgrowth inhibitory molecule e.g. Nogo and a pro-inflammatory molecule e.g. TNF, may be desirable (see McGee A W, et al., Trends Neurosci. 2003; 26:193; Marco Domeniconi, et al., J Neurol Sci. 2005; 233:43; Milan Makwanal, et al., FEBS J. 2005; 272:2628; Barry J. Dickson, Science. 2002; 298:1959; Felicia Yu Hsuan Teng, et al., J Neurosci Res. 2005; 79:273; Tara Karnezis, et al., Nature Neuroscience 2004; 7, 736; Gang Xu, et al., J. Neurochem. 2004; 91; 1018).

Other FIT-Igs contemplated are those capable of binding target pairs such as NgR and RGM A; NogoA and RGM A; MAG and RGM A; OMGp and RGM A; RGM A and RGM B; CSPGs and RGM A; aggrecan, midkine, neurocan, versican, phosphacan, Te38 and TNF-a; Aß globulomer-specific antibodies combined with antibodies promoting dendrite & axon sprouting. Dendrite pathology is a very early sign of AD and it is known that NOGO A restricts dendrite growth. One can combine such type of ab with any of the SCI-candidate (myelin-proteins) Ab. Other FIT-Ig targets may include any combination of NgR-p75, NgR-Troy, NgR-Nogo66 (Nogo), NgR-Lingo, Lingo-Troy, Lingo-p75, MAG or Omgp. Additionally, targets may also include any mediator, soluble or cell surface, implicated in inhibition of neurite e.g Nogo, Ompg, MAG, RGM A, semaphorins, ephrins, soluble A-b, pro-inflammatory cytokines (e.g. IL-1), chemokines (e.g. MIP 1a), molecules that inhibit nerve regeneration. The efficacy of anti-nogo/anti-RGM A or similar FIT-Ig molecules can be validated in pre-clinical animal models of spinal cord injury. In addition, these FIT-Ig molecules can be constructed and tested for efficacy in the animal models and the best therapeutic FIT-Ig can be selected for testing in human patients. In addition, FIT-Ig molecules can be constructed that target two distinct ligand binding sites on a single receptor e.g. Nogo receptor which binds three ligand Nogo, Ompg, and MAG and RAGE that binds A-b and S100 A. Furthermore, neurite outgrowth inhibitors e.g. nogo and nogo receptor, also play a role in preventing nerve regeneration in immunological diseases like multiple sclerosis Inhibition of nogo-nogo receptor interaction has been shown to enhance recovery in animal models of multiple sclerosis. Therefore, FIT-Ig molecules that can block the function of one immune mediator eg a cytokine like IL-12 and a neurite outgrowth inhibitor molecule eg nogo or RGM may offer faster and greater efficacy than blocking either an immune or an neurite outgrowth inhibitor molecule alone.

Monoclonal antibody therapy has emerged as an important therapeutic modality for cancer (von Mehren M, et al 2003 Monoclonal antibody therapy for cancer. Annu Rev Med.; 54:343-69). Antibodies may exert antitumor effects by inducing apoptosis, redirected cytotoxicity, interfering with ligand-receptor interactions, or preventing the expression of proteins that are critical to the neoplastic phenotype. In addition, antibodies can target components of the tumor microenvironment, perturbing vital structures such as the formation of tumor-associated vasculature. Antibodies can also target receptors whose ligands are growth factors, such as the epidermal growth factor receptor. The antibody thus inhibits natural ligands that stimulate cell growth from binding to targeted tumor cells. Alternatively, antibodies may induce an anti-idiotype network, complement-mediated cytotoxicity, or antibody-dependent cellular cytotoxicity (ADCC). The use of dual-specific antibody that targets two separate tumor mediators will likely give additional benefit compared to a mono-specific therapy. FIT-Ig Igs capable of binding the following pairs of targets to treat oncological disease are also contemplated: IGF1 and IGF2; IGF1/2 and Erb2B; VEGFR and EGFR; CD20 and CD3, CD138 and CD20, CD38 and CD20, CD38 & CD138, CD40 and CD20, CD138 and CD40, CD38 and CD40. Other target combinations include one or more members of the EGF/erb-2/erb-3 family. Other targets (one or more) involved in oncological diseases that FIT-Ig Igs may bind include, but are not limited to those selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NR0B1, NR0B2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB2IP, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAI1, COL4A3, IL8, LAMA5, NRP1, NRP2, STAB1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (NGF), NGFR, NME1 (NM23A), PGR, PLAU (uPA), PTEN, CTLA-4, OX40, GITR, TIM-3, Lag-3, B7-H3, B7-H4, GDF8, CGRP, Lingo-1, ICOS, GARP, BTLA, CD160, ROR1, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94).

In an embodiment, diseases that can be treated or diagnosed with the compositions and methods provided herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

In an embodiment, the antibodies provided herein and antigen-binding portions thereof, are used to treat cancer or in the prevention of metastases from the tumors described herein either when used alone or in combination with radiotherapy and/or other chemotherapeutic agents.

According to another embodiment of the invention, the human immune effector cell is a member of the human lymphoid cell lineage. In this embodiment, the effector cell may advantageously be a human T cell, a human B cell or a human natural killer (NK) cell. Advantageously, such cells will have either a cytotoxic or an apoptotic effect on the target cell. Especially advantageously, the human lymphoid cell is a cytotoxic T cell which, when activated, exerts a cytotoxic effect on the target cell. According to this embodiment, then, the recruited activity of the human effector cell is this cell's cytotoxic activity.

According to a preferred embodiment, activation of the cytotoxic T cell may occur via binding of the CD3 antigen as effector antigen on the surface of the cytotoxic T cell by a bispecific antibody of this embodiment of the invention. The human CD3 antigen is present on both helper T cells and cytotoxic T cells. Human CD3 denotes an antigen which is expressed on T cells as part of the multimolecular T cell complex and which comprises three different chains: CD3-epsilon, CD3-delta and CD3-gamma.

The activation of the cytotoxic potential of T cells is a complex phenomenon which requires the interplay of multiple proteins. The T cell receptor ("TCR") protein is a membrane bound disulfide-linked heterodimer consisting of two different glycoprotein subunits. The TCR recognizes and binds foreign peptidic antigen which itself has been bound by a member of the highly diverse class of major histocompatibility complex ("MHC") proteins and has been presented, bound to the MHC, on the surface of antigen presenting cells ("APCs").

Although the variable TCR binds foreign antigen as outlined above, signaling to the T cell that this binding has taken place depends on the presence of other, invariant, signaling proteins associated with the TCR. These signaling proteins in associated form are collectively referred to as the CD3 complex, here collectively referred to as the CD3 antigen.

The activation of T cell cytotoxicity, then, normally depends first on the binding of the TCR with an MHC protein, itself bound to foreign antigen, located on a separate cell. Only when this initial TCR-MHC binding has taken place can the CD3-dependent signaling cascade responsible for T cell clonal expansion and, ultimately, T cell cytotoxicity ensue.

However, binding of the human CD3 antigen by the first or second portion of a bispecific antibody of the invention activates T cells to exert a cytotoxic effect on other cells in the absence of independent TCR-MHC binding. This means that T cells may be cytotoxically activated in a clonally independent fashion, i.e., in a manner which is independent of the specific TCR clone carried by the T cell. This allows an activation of the entire T cell compartment rather than only specific T cells of a certain clonal identity.

In light of the foregoing discussion, then, an especially preferred embodiment of the invention provides a bispecific antibody in which the effector antigen is the human CD3 antigen. The bispecific antibody according to this embodiment of the invention may have a total of either two or three antibody variable domains.

According to further embodiments of the invention, other lymphoid cell-associated effector antigens bound by a bispecific antibody of the invention may be the human CD16 antigen, the human NKG2D antigen, the human NKp46 antigen, the human CD2 antigen, the human CD28 antigen or the human CD25 antigen.

According to another embodiment of the invention, the human effector cell is a member of the human myeloid lineage. Advantageously, the effector cell may be a human monocyte, a human neutrophilic granulocyte or a human dendritic cell. Advantageously, such cells will have either a cytotoxic or an apoptotic effect on the target cell. Advantageous antigens within this embodiment which may be bound by a bispecific antibody of the invention may be the human CD64 antigen or the human CD89 antigen.

According to another embodiment of the invention, the target antigen is an antigen which is uniquely expressed on a target cell or effector cell in a disease condition, but which remains either non-expressed, expressed at a low level or non-accessible in a healthy condition. Examples of such target antigens which might be specifically bound by a bispecific antibody of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5AC, MUC5B, MUC7, βhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, LG, SAS and CD63.

According to a specific embodiment, the target antigen specifically bound by a bispecific antibody may be a cancer-related antigen, that is an antigen related to a malignant condition. Such an antigen is either expressed or accessible on a malignant cell, whereas the antigen is either not present, not significantly present, or is not accessible on a non-malignant cell. As such, a bispecific antibody according to this embodiment of the invention is a bispecific antibody which recruits the activity of a human immune effector cell against the malignant target cell bearing the target antigen, or rendering the target antigen accessible.

Gene Therapy: In a specific embodiment, nucleic acid sequences encoding a binding protein provided herein or another prophylactic or therapeutic agent provided herein are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acids produce their encoded antibody or prophylactic or therapeutic agent provided herein that mediates a prophylactic or therapeutic effect.

Any of the methods for gene therapy available in the art can be used in the methods provided herein. For general reviews of the methods of gene therapy, see Goldspiel et al. (1993) Clin. Pharmacy 12:488-505; Wu and Wu (1991) Biotherapy 3:87-95; Tolstoshev (1993) Ann Rev. Pharmacol. Toxicol. 32:573-596; Mulligan (1993) Science 260:926-932; Morgan and Anderson (1993) Ann Rev. Biochem. 62:191-217; and May (1993) TIBTECH 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed description of various methods of gene therapy are disclosed in US Patent Publication No. US20050042664.

Diagnostics: The disclosure herein also provides diagnostic applications including, but not limited to, diagnostic assay methods, diagnostic kits containing one or more binding proteins, and adaptation of the methods and kits for use in automated and/or semi-automated systems. The methods, kits, and adaptations provided may be employed in the detection, monitoring, and/or treatment of a disease or disorder in an individual. This is further elucidated below.

A. Method of Assay: The present disclosure also provides a method for determining the presence, amount or concentration of an analyte, or fragment thereof, in a test sample using at least one binding protein as described herein. Any suitable assay as is known in the art can be used in the method. Examples include, but are not limited to, immunoassays and/or methods employing mass spectrometry. Immunoassays provided by the present disclosure may include sandwich immunoassays, radioimmunoassay (RIA), enzyme immunoassay (EIA), enzyme-linked immunosorbent assay (ELISA), competitive-inhibition immunoassays, fluorescence polarization immunoassay (FPIA), enzyme multiplied immunoassay technique (EMIT), bioluminescence resonance energy transfer (BRET), and homogenous chemiluminescent assays, among others. A chemiluminescent microparticle immunoassay, in particular one employing the ARCHITECT® automated analyzer (Abbott Laboratories, Abbott Park, Ill.), is an example of an immunoassay. Methods employing mass spectrometry are provided by the present disclosure and include, but are not limited to MALDI (matrix-assisted laser desorption/ionization) or by SELDI (surface-enhanced laser desorption/ionization).

Methods for collecting, handling, processing, and analyzing biological test samples using immunoassays and mass spectrometry would be well-known to one skilled in the art, are provided for in the practice of the present disclosure (US 2009-0311253 A1).

B. Kit: A kit for assaying a test sample for the presence, amount or concentration of an analyte, or fragment thereof, in a test sample is also provided. The kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or an anti-analyte binding protein (or a fragment, a variant, or a fragment of a variant thereof), which is optionally immobilized on a solid phase. Optionally, the kit may comprise a calibrator or control, which may comprise isolated or purified analyte. The kit can comprise at least one component for assaying the test sample for an analyte by immunoassay and/or mass spectrometry. The kit components, including the analyte, binding protein, and/or anti-analyte binding protein, or fragments thereof, may be optionally labeled using any art-known detectable label. The materials and methods for the creation provided for in the practice of the present disclosure would be known to one skilled in the art (US 2009-0311253 A1).

C. Adaptation of Kit and Method: The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, for example, in U.S. Pat. Nos. 5,089,424 and 5,006,309, and as commercially marketed, for example, by Abbott Laboratories (Abbott Park, Ill.) as ARCHITECT®. Other platforms available from Abbott Laboratories include, but are not limited to, AxSYM®, IMx® (see, for example, U.S. Pat. No. 5,294,404, PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253. It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1. Construction, Expression, Purification, and Analysis of Anti-IL17/IL-20 Fabs-in-Tandem Immunoglobulin (FIT-Ig)

To demonstrate the FIT-Ig technology, we have generated a group of anti-IL-17/IL-20 FIT-Ig molecules: FIT1-Ig, FIT2-Ig, and FIT3-Ig, all of which contains 3 different polypeptides, as shown in FIG. 1, where antigen A is IL-17 and antigen B is IL-20. The DNA construct used to generate FIT-Ig capable of binding IL-17 and IL-20 is illustrated in FIG. 1B. Briefly, parental mAbs included two high affinity antibodies, anti-IL-17 (clone LY) (U.S. Pat. No. 7,838,638) and anti-hIL-20 (clone 15D2) (U.S. Patent Application Publication No. US2014/0194599). To generate FIT-Ig construct #1, the VL-CL of LY was directly (FIT1-Ig), or through a linker of 3 amino acids (FIT2-Ig) or 7 amino acids (FIT3-Ig) fused to the N-terminus of the 15D2 heavy chain (as shown in Table 1). The construct #2 is VH-CH1 of LY, and the $3^{rd}$ construct is VL-CL of 15D2. The 3 constructs for each FIT-Ig were co-transfected in 293 cells, resulting in the expression and secretion of FIT-Ig protein.

Figure 2:
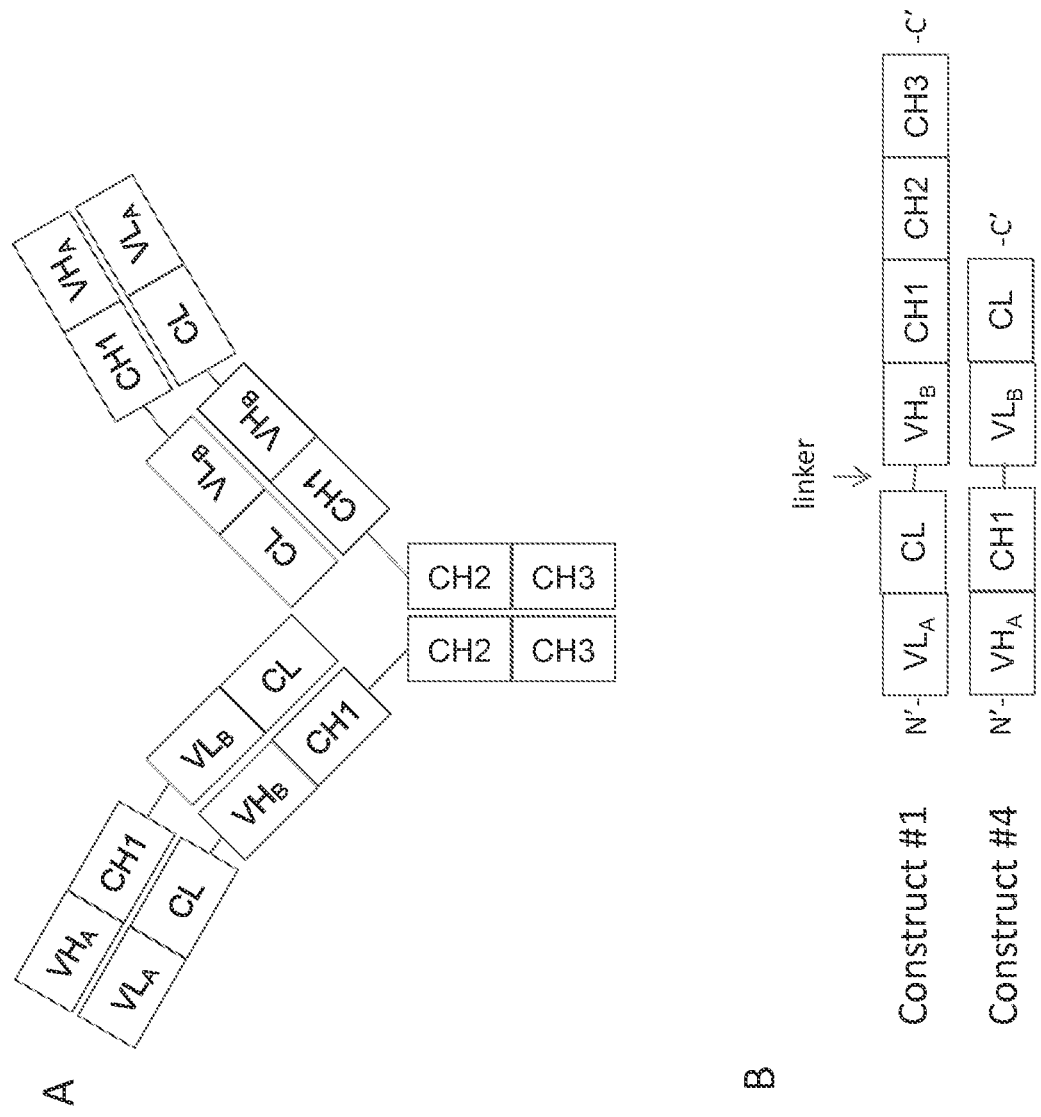
FIG. 2A shows the basic structure of FIT-Igs that are made up of two constructs.
FIG. 2B shows the two constructs used to prepare such FIT-Igs.

We also generated a group of anti-IL-17/IL-20 FIT-Ig molecules: FIT4-Ig, FIT5-Ig, and FIT6-Ig, each of which contains 2 different polypeptides, as shown in FIG. 2. The DNA constructs used to generate FIT-Ig capable of binding IL-17 and IL-20 are illustrated in FIG. 2B, where antigen A is IL-17 and antigen B is IL-20. Briefly, parental mAbs included two high affinity antibodies, anti-IL-17 (clone LY) and anti-hIL-20 (clone 15D2). To generate FIT-Ig construct #1, the VL-CL of LY was directly (FIT4-Ig), or through a linker of 3 amino acids (FIT5-Ig) or 7 amino acids (FIT6-Ig) fused to the N-terminus of the 15D2 heavy chain (as shown in Table 1). To generate FIT-Ig construct #4, the VH-CH1 of LY was directly (FIT4-Ig), or through a linker of 3 amino acids (FIT5-Ig) or 7 amino acids (FIT6-Ig) fused to the N-terminus of the 15D2 light chain. The 2 DNA constructs (construct #1 and #4) for each FIT-Ig were co-transfected in 293 cells, resulting in the expression and secretion of FIT-Ig protein. The detailed procedures of the PCR cloning are described below.

Example 1.1. Molecular Cloning of Anti-IL-17/IL-20 FIT-Ig Molecules

For construct #1 cloning, LY light chain was amplified by PCR using forward primers annealing on light chain signal sequence and reverse primers annealing on C-terminus of the light chain. 15D2 heavy chain was amplified by PCR using forward primers annealing on N-terminus of 15D2 VH and reverse primers annealing on C-terminus of CH. These 2 PCR fragments were gel purified and combined by overlapping PCR using signal peptide and CH primer pair. The combined PCR product was cloned into a 293 expression vector, which already contained the human Fc sequence.

TABLE 1

Anti-IL-17/IL-20 FIT-Ig molecules and DNA constructs.

| FIT-Ig molecule | Construct #1 | Linker | Construct #2 | Construct #3 | Construct #4 |
|---|---|---|---|---|---|
| FIT1-Ig | $VL_{17}$-CL-$VH_{20}$-CH1-Fc | No linker | $VH_{17}$-CH1 | $VL_{20}$-CL | |
| FIT2-Ig | $VL_{17}$-CL-linker-$VH_{20}$-CH1-Fc | GSG | $VH_{17}$-CH1 | $VL_{20}$-CL | |
| FIT3-Ig | $VL_{17}$-CL-linker-$VH_{20}$-CH1-Fc | GGGGSGS | $VH_{17}$-CH1 | $VL_{20}$-CL | |
| FIT4-Ig | $VL_{17}$-CL-$VH_{20}$-CH1-Fc | No linker | | | $VH_{17}$-CH1-$VL_{20}$-CL |
| FIT5-Ig | $VL_{17}$-CL-linker-$VH_{20}$-CH1-Fc | GSG | | | $VH_{17}$-CH1-linker-$VL_{20}$-CL |
| FIT6-Ig | $VL_{17}$-CL-linker-$VH_{20}$-CH1-Fc | GGGGSGS | | | $VH_{17}$-CH1-linker-$VL_{20}$-CL |

For construct #2 cloning, LY VH-CH1 was amplified by PCR using forward primers annealing on heavy chain signal peptide and reverse primer annealing on C-terminal of CH1. The PCR product was gel purified before cloning into 293 expression vector.

For construct #3, 15D2 light chain was amplified by PCR using forward primer annealing on N-terminal of light chain signal peptide and reverse primer annealing on the end of CL. The PCR product was gel purified before cloning into 293 expression vector.

For construct #4 cloning, LY VH-CH1 was amplified by PCR using forward primer annealing on N-terminus of heavy chain signal peptide and reverse primer annealing on the end of CH1. 15D2 VL was amplified using primers annealing on the end of 15D2 VL. Both PCR products were gel purified and combined by overlap PCR. The combined PCR product was gel purified and cloned in 293 expression vector. Table 2 shows sequences of PCR primers used for above molecular cloning.

TABLE 2

PCR primers used for molecular construction of anti-IL-17/anti-CD20 FIT-Igs

| | |
|---|---|
| P1: 5' CAGGTGCAGCTGGTGCAGAGCGGCGCCGAAG 3' | SEQ ID NO. 1 |
| P2:<br>5'GCTGGACCTGAGAGCCTGAACCGCCACCACCACACTCTCCCCTGT<br>TGAAGC 3' | SEQ ID NO. 2 |

TABLE 2-continued

PCR primers used for molecular construction of anti-IL-17/anti-CD20 FIT-Igs

| Primer | Sequence | SEQ ID |
|---|---|---|
| P3: | 5' GGTGGTGGCGGTTCAGGCTCTCAGGTCCAGCTTGTGCAATCTGGCGCCGAGG 3' | SEQ ID NO. 3 |
| P4: | 5' GTCTGCGGCCGCTCATTTACCCGGAGACAGGGAGAG 3' | SEQ ID NO. 4 |
| P5: | 5' TAAGCGTACGGTGGCTGCACCATCTGTCTTC 3' | SEQ ID NO. 5 |
| P6: | 5' CGGCGCCAGATTGCACAAGCTGGACCTGGCCTGAACCACACTCTCCCCTGTTGAAGCTC 3' | SEQ ID NO. 6 |
| P7: | 5' GCTGGACCTGAGAGCCTGAACCGCCACCACCACACTCTCCCCTGTTGAAGC 3' | SEQ ID NO. 7 |
| P8: | 5' GGTGGTGGCGGTTCAGGCTCTCAGGTCCAGCTTGTGCAATCTGGCGCCGAGG 3' | SEQ ID NO. 8 |
| P9: | 5' TACCTCGGCGCCAGATTGCACAAGCTGGACCTGACACTCTCCCCTGTTGAAGCTCTTTG 3' | SEQ ID NO. 9 |
| P10: | 5' CATGACACCTTAACAGAGGCCCCAGGTCGTTTTACCTCGGCGCCAGATTGCACAAG 3' | SEQ ID NO. 10 |
| P11: | 5' CAATAAGCTTTACATGACACCTTAACAGAGGCCCCAG 3' | SEQ ID NO. 11 |
| P12: | 5' TCGAGCGGCCGCTCAACAAGATTTGGGCTCAACTTTCTTG 3' | SEQ ID NO. 12 |
| P13: | 5' GCTGCTGCTGTGGTTCCCCGGCTCGCGATGCGCTATACAGTTGACACAGTC 3' | SEQ ID NO. 13 |
| P14: | 5' GAAGATGAAGACAGATGGTGCAGCCACCGTACGCTTGATCTCTACCTTTGTTC 3' | SEQ ID NO. 14 |

The final sequences of hIL-17/hIL-20 FIT1-Ig, FIT2-Ig, FIT3-Ig, FIT4-Ig, FIT5-Ig, and FIT6-Ig are listed in Table 3.

TABLE 3

Amino acid sequences of anti-IL-17/IL-20 FIT-Ig molecules

| Protein | Protein region | Sequence Identifier | Sequence 12345678901234567890 |
|---|---|---|---|
| Anti-IL-17/IL-20 FIT1-Ig POLYPEPTIDE #1 | | SEQ ID NO.: 15 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECQVQ LVQSGAEVKRPGASVKVSCKASGYTFTNDIIHWVRQA PGQRLEWMGWINAGYGNTQYSQNFQDRVSITRDTSAS TAYMELISLRSEDTAVYYCAREPLWFGESSPHDYYGM DVWGQGTTVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK* |

TABLE 3-continued

Amino acid sequences of anti-IL-17/IL-20 FIT-Ig molecules

| Protein | Protein region | Sequence Identifier | Sequence<br>12345678901234567890 |
|---|---|---|---|
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| | Linker | None | |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT1-Ig POLYPEPTIDE #2 | | SEQ ID NO.: 21 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| Anti-IL-17/IL-20 FIT1-Ig POLYPEPTIDE #3 | | SEQ ID NO.: 23 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC* |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |
| Anti-IL-17/IL-20 FIT2-Ig POLYPEPTIDE #1 | | SEQ ID NO.: 25 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECGSG QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSSASTKGPSVFPLAPSSKSTSGG TAALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKD TLMISRTPEVTCVVVDVSHEDPEVKFNWYVDGVEVHN AKTKPREEQYNSTYRVVSVLTVLHQDWLNGKEYKCKV SNKALPAPIEKTISKAKGQPREPQVYTLPPSREEMTK NQVSLTCLVKGFYPSDIAVEWESNGQPENNYKTTPPV LDSDGSFFLYSKLTVDKSRWQQGNVFSCSVMHEALHN HYTQKSLSLSPGK* |
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |

TABLE 3-continued

Amino acid sequences of anti-IL-17/IL-20 FIT-Ig molecules

| Protein | Protein region | Sequence Identifier | Sequence<br>12345678901234567890 |
|---|---|---|---|
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT2-Ig POLYPEPTIDE #2 | | SEQ ID NO.: 21 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| Anti-IL-17/IL-20 FIT2-Ig POLYPEPTIDE #3 | | SEQ ID NO.: 23 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC* |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |
| Anti-IL-17/IL-20 FIT3-Ig POLYPEPTIDE #1 | | SEQ ID NO.: 27 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECGGG GSGSQVQLVQSGAEVKRPGASVKVSCKASGYTFTNDI IHWVRQAPGQRLEWMGWINAGYGNTQYSQNFQDRVSI TRDTSASTAYMELISLRSEDTAVYYCAREPLWFGESS PHDYYGMDVWGQGTTVTVSSASTKGPSVFPLAPSSKS TSGGTAALGCLVKDYFPEPVTVSWNSGALTSGVHTFP AVLQSSGLYSLSSVVTVPSSSLGTQTYICNVNHKPSN TKVDKKVEPKSCDKTHTCPPCPAPELLGGPSVFLFPP KPKDTLMISRTPEVTCVVVDVSHEDPEVKFNWYVDGV EVHNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNYKT TPPVLDSDGSFFLYSKLTVDKSRWQQGNVFSCSVMHE ALHNHYTQKSLSLSPGK* |
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |

TABLE 3-continued

Amino acid sequences of anti-IL-17/IL-20 FIT-Ig molecules

| Protein | Protein region | Sequence Identifier | Sequence |
|---|---|---|---|
| | Linker | SEQ ID NO.: 28 | GGGGSGS |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT3-Ig POLYPEPTIDE #2 | | SEQ ID NO.: 21 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| Anti-IL-17/IL-20 FIT3-Ig POLYPEPTIDE #3 | | SEQ ID NO.: 23 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC* |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |
| Anti-IL-17/IL-20 FIT4-Ig POLYPEPTIDE #1 | | SEQ ID NO.: 15 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECQVQ LVQSGAEVKRPGASVKVSCKASGYTFTNDIIHWVRQA PGQRLEWMGWINAGYGNTQYSQNFQDRVSITRDTSAS TAYMELISLRSEDTAVYYCAREPLWFGESSPHDYYGM DVWGQGTTVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK* |
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| | Linker | | None |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |

TABLE 3-continued

Amino acid sequences of anti-IL-17/IL-20 FIT-Ig molecules

| Protein | Protein region | Sequence Identifier | Sequence |
|---|---|---|---|
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT4-Ig POLYPEPTIDE #4 | | SEQ ID NO.: 29 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC* |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Linker | | none |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |
| Anti-IL-17/IL-20 FIT5-Ig POLYPEPTIDE #1 | | SEQ ID NO.: 25 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECGSG QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSSASTKGPSVFPLAPSSKSTSGG TAALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKD TLMISRTPEVTCVVVDVSHEDPEVKFNWYVDGVEVHN AKTKPREEQYNSTYRVVSVLTVLHQDWLNGKEYKCKV SNKALPAPIEKTISKAKGQPREPQVYTLPPSREEMTK NQVSLTCLVKGFYPSDIAVEWESNGQPENNYKTTPPV LDSDGSFFLYSKLTVDKSRWQQGNVFSCSVMHEALHN HYTQKSLSLSPGK* |
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT5-Ig POLYPEPTIDE #4 | | SEQ ID NO.: 30 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC GSGAIQLTQSPSSLSASVGDRVTITCRASQGISSALA WYQQKPGKAPKLLIYDASSLESGVPSRFSGSGSGTDF TLTISSLQPEDFATYYCQQFNSYPLTFGGGTKVEIKR TVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC* |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Linker | SEQ ID NO.: 26 | GSG |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |
| Anti-IL-17/IL-20 FIT6-Ig POLYPEPTIDE #1 | | SEQ ID NO.: 27 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGECGGG GSGSQVQLVQSGAEVKRPGASVKVSCKASGYTFTNDI IHWVRQAPGQRLEWMGWINAGYGNTQYSQNFQDRVSI TRDTSASTAYMELISLRSEDTAVYYCAREPLWFGESS PHDYYGMDVWGQGTTVTVSSASTKGPSVFPLAPSSKS TSGGTAALGCLVKDYFPEPVTVSWNSGALTSGVHTFP AVLQSSGLYSLSSVVTVPSSSLGTQTYICNVNHKPSN TKVDKKVEPKSCDKTHTCPPCPAPELLGGPSVFLFPP KPKDTLMISRTPEVTCVVVDVSHEDPEVKFNWYVDGV EVHNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNYKT TPPVLDSDGSFFLYSKLTVDKSRWQQGNVFSCSVMHE ALHNHYTQKSLSLSPGK* |
| | LY VL | SEQ ID NO.: 16 | DIVMTQTPLSLSVTPGQPASISCRSSRSLVHSRGNTY LHWYLQKPGQSPQLLIYKVSNRFIGVPDRFSGSGSGT DFTLKISRVEAEDVGVYYCSQSTHLPFTFGQGTKLEI K |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| | Linker | | GGGGSGS |
| | 15D2 VH | SEQ ID NO.: 18 | QVQLVQSGAEVKRPGASVKVSCKASGYTFTNDIIHWV RQAPGQRLEWMGWINAGYGNTQYSQNFQDRVSITRDT SASTAYMELISLRSEDTAVYYCAREPLWFGESSPHDY YGMDVWGQGTTVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |

TABLE 3-continued

Amino acid sequences of anti-IL-17/IL-20 FIT-Ig molecules

| Protein | Protein region | Sequence Identifier | Sequence<br>12345678901234567890 |
|---|---|---|---|
| | Fc | SEQ ID NO.: 20 | DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK* |
| Anti-IL-17/IL-20 FIT6-Ig POLYPEPTIDE #4 | | SEQ ID NO.: 31 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC GGGGSGSAIQLTQSPSSLSASVGDRVTITCRASQGIS SALAWYQQKPGKAPKLLIYDASSLESGVPSRFSGSGS GTDFTLTISSLQPEDFATYYCQQFNSYPLTFGGGTKV EIKRTVAAPSVFIFPPSDEQLKSGTASVVCLLNNFYP REAKVQWKVDNALQSGNSQESVTEQDSKDSTYSLSST LTLSKADYEKHKVYACEVTHQGLSSPVTKSFNRGEC* |
| | LY VH | SEQ ID NO.: 22 | QVQLVQSGAEVKKPGSSVKVSCKASGYSFTDYHIHWV RQAPGQGLEWMGVINPMYGTTDYNQRFKGRVTITADE STSTAYMELSSLRSEDTAVYYCARYDYFTGTGVYWGQ GTLVTVSS |
| | CH1 | SEQ ID NO.: 19 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| | Linker | SEQ ID NO.: 28 | GGGGSGS |
| | 15D2 VL | SEQ ID NO.: 24 | AIQLTQSPSSLSASVGDRVTITCRASQGISSALAWYQ QKPGKAPKLLIYDASSLESGVPSRFSGSGSGTDFTLT ISSLQPEDFATYYCQQFNSYPLTFGGGTKVEIK |
| | CL | SEQ ID NO.: 17 | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC* |

Example 1.2. Expression, Purification, and Analysis of Anti-IL-17/IL-20 FIT-Ig Proteins All DNA constructs of each FIT-Ig were subcloned into pBOS based vectors, and sequenced to ensure accuracy. Construct #1, #2, and #3 of each FIT-Ig (1, 2, and 3), or construct #1 and #4 of each FIT-Ig (4, 5, and 6) were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells (1.0-1.2×10$^6$/ml, cell viability >95%) at 60 μg DNA/120 ml culture. After 6-24 hours culture in shaker, peptone was added to the transfected cells at a final concentration of 5%, with shaking at 125 rpm/min., at 37° C., 8% $CO_2$. On the 6th-7th day, supernatant was harvested by centrifugation and filtration, and FIT-Ig protein was purified using protein A chromatography (Pierce, Rockford, Ill.) according to the manufacturer's instructions. The proteins were analyzed by SDS-PAGE and their concentrations determined by A280 and BCA (Pierce, Rockford, Ill.).

For the expression of FIT1-Ig, FIT2-Ig, and FIT3-Ig, different DNA molar ratios of the 3 constructs were used, including construct #1:#2:#3=1:1:1, construct #1:#2:#3=1:1.5:1.5, and construct #1:#2:#3=1:3:3 (Table 4). FIT-Ig proteins were purified by protein A chromatography. The purification yield (7-16 mg/L) was consistent with hIgG quantification of the expression medium for each protein. The composition and purity of the purified FIT-Igs were analyzed by SDS-PAGE in both reduced and non-reduced conditions. In non-reduced conditions, FIT-Ig migrated as a single band of approximately 250 KDa. In reducing conditions, each of the FIT-Ig proteins yielded two bands, one higher MW band is construct #1 of approximately 75 KDa, and one lower MW band corresponds to both construct #2 and #3 overlapped at approximately 25 KDa. The SDS-PAGE showed that each FIT-Ig is expressed as a single species, and the 3 polypeptide chains are efficiently paired to form an IgG-like molecule. The sizes of the chains as well as the full-length protein of FIT-Ig molecules are consistent with their calculated molecular mass based on amino acid sequences.

TABLE 4

Expression and SEC analysis of hIL-17/IL-20 FIT-Ig proteins

| FIT-Ig protein | DNA ratio: Construct 1:2:3 | Expression level (mg/L) | % Peak monomeric fraction by SEC |
|---|---|---|---|
| FIT1-Ig | 1:1:1 | 15.16 | 92.07 |
| | 1:1.5:1.5 | 14.73 | 95.49 |
| | 1:3:3 | 9.87 | 97.92 |
| FIT2-Ig | 1:1:1 | 15.59 | 90.92 |
| | 1:1.5:1.5 | 12.61 | 94.73 |
| | 1:3:3 | 7.03 | 97.29 |
| FIT3-Ig | 1:1:1 | 15.59 | 91.47 |
| | 1:1.5:1.5 | 15.16 | 94.08 |
| | 1:3:3 | 7.75 | 97.57 |

To further study the physical properties of FIT-Ig in solution, size exclusion chromatography (SEC) was used to analyze each protein. For SEC analysis of the FIT-Ig, purified FIT-Ig, in PBS, was applied on a TSKgel SuperSW3000, 300×4.6 mm column (TOSOH). An HPLC instrument, Model U3000 (DIONEX) was used for SEC. All proteins were determined using UV detection at 280 nm and 214 nm. The elution was isocratic at a flow rate of 0.25 mL/min. All 3 FIT-Ig proteins exhibited a single major peak, demonstrating physical homogeneity as monomeric proteins (Table 4). The ratio of construct #1:#2:#3=1:3:3 showed a better monomeric profile by SEC for all 3 FIT-Ig proteins (Table 4).

Table 4 also shows that the expression levels of all the FIT-Ig proteins are comparable to that of the regular mAbs, indicating that the FIT-Ig can be expressed efficiently in mammalian cells. For the expression of FIT4-Ig, FIT5-Ig, and FIT6-Ig, the DNA ration of construct #1:#4=1:1, and the expression level were in the range of 1-10 mg/L, and the % Peak monomeric fraction as determined by SEC was in the range of 58-76%. Based on this particular mAb combination (LY and 15D2), the 3-polypeptide FIT-Ig constructs (FIT1-Ig, FIT2-Ig, and FIT3-Ig) showed better expression profile than that of the 2-polypeptide FIT-Ig constructs (FIT4-Ig, FIT5-Ig, and FIT6-Ig), therefore FIT1-Ig, FIT2-Ig, and FIT3-Ig were further analyzed for functional properties

Example 1.3. Determination of Antigen Binding Affinity of Anti-IL-17/IL-20 FIT-Igs The kinetics of FIT-Ig binding to rhIL-17 and rhIL-20 was determined by surface plasmon resonance (Table 5) with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, goat anti-human IgG Fcγ fragment specific polyclonal antibody (Pierce Biotechnology Inc, Rockford, Ill.) was directly immobilized across a CM5 research grade biosensor chip using a standard amine coupling kit according to manufacturer's instructions. Purified FIT-Ig samples were diluted in HEPES-buffered saline for capture across goat anti-human IgG Fc specific reaction surfaces and injected over reaction matrices at a flow rate of 5 µl/min. The association and dissociation rate constants, kon (M-1s-1) and koff (s-1) were determined under a continuous flow rate of 30 µL/min. Rate constants were derived by making kinetic binding measurements at ten different antigen concentrations ranging from 1.25 to 1000 nM. The equilibrium dissociation constant (M) of the reaction between FIT-Ig and the target proteins was then calculated from the kinetic rate constants by the following formula: KD=koff/kon. Aliquots of antigen samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 µL/min. The anti-Fc antibody immobilized surfaces were completely regenerated and retained their full capture capacity over twelve cycles.

TABLE 5

Functional characterizations of anti-IL-17/IL-20 FIT-Ig molecules

| mAb or FIT-Ig | Antigen | Binding Kinetics by Biacore | | | Neutralization |
| --- | --- | --- | --- | --- | --- |
| | | $k_{on}$ ($M^{-1}s^{-1}$) | $k_{off}$ ($s^{-1}$) | $K_d$ (M) | Potency $IC_{50}$ (pM) |
| LY | hIL-17 | 8.24E+5 | 1.80E−5 | 2.18E−11 | 101 |
| FIT1-Ig | hIL-17 | 1.07E+7 | 3.88E−5 | 3.64E−12 | 102 |
| FIT2-Ig | hIL-17 | 9.24E+6 | 1.53E−5 | 1.65E−12 | 137 |
| FIT3-Ig | hIL-17 | 8.71E+6 | 9.58E−6 | 1.10E−12 | 146 |
| 15D2 | hIL-20 | 1.70E+6 | 8.30E−5 | 5.00E−11 | 50 |
| FIT1-Ig | hIL-20 | 1.40E+6 | 3.82E−5 | 2.73E−11 | 54 |
| FIT2-Ig | hIL-20 | 1.80E+6 | 3.50E−5 | 1.95E−11 | 50 |
| FIT3-Ig | hIL-20 | 1.40E+6 | 3.82E−5 | 2.73E−11 | 72 |

The Biacore analysis indicated the overall binding parameters of the three FIT-Igs to hIL-17 and hIL-20 were similar, with the affinities of the FIT-Igs being very close to that of the parental mAb LY and 15D2, and there was no lose of binding affinities for either antigen binding domains (Table 5).

Figure 3:
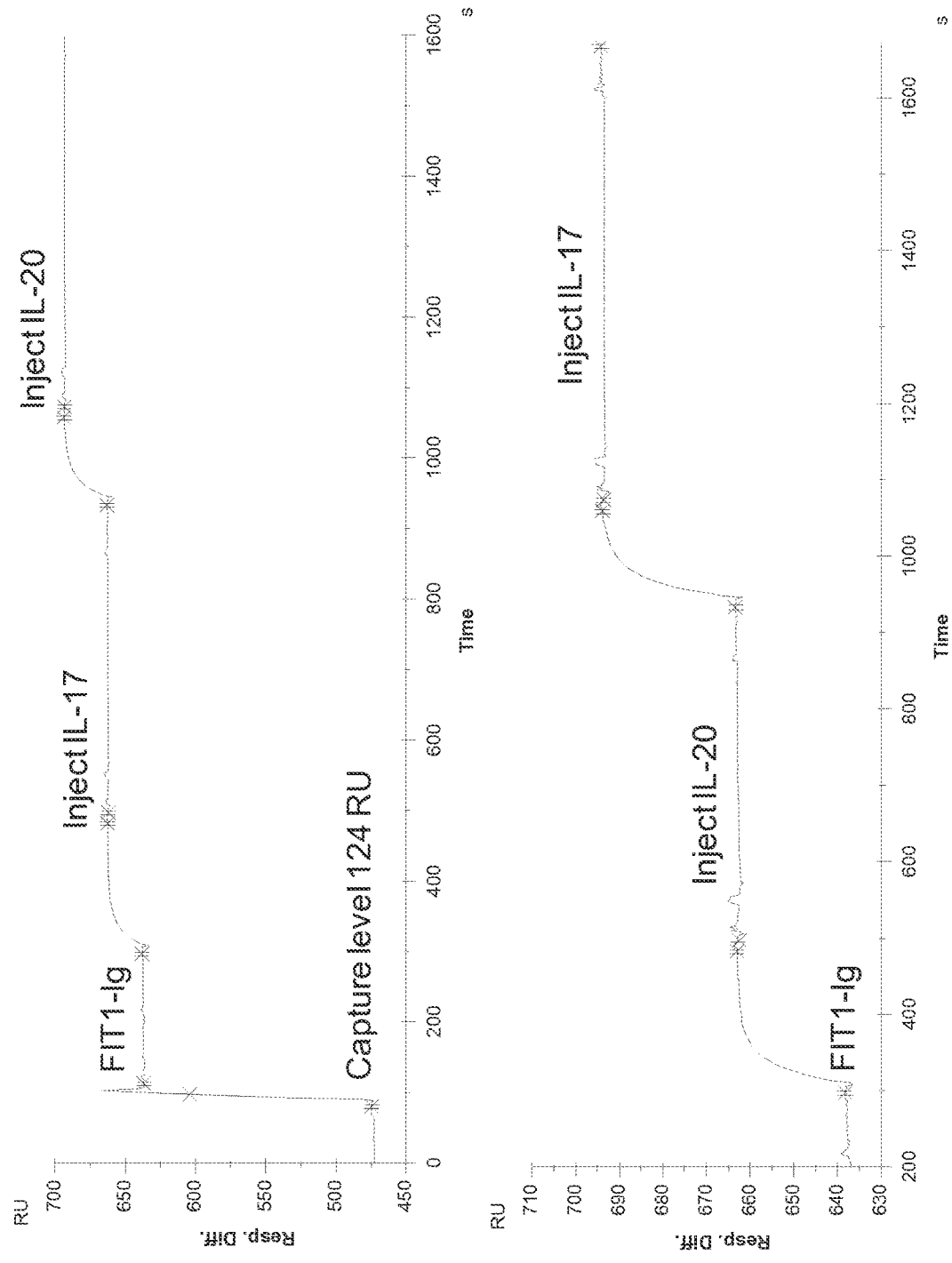
FIG. 3 provides the dual-specific antigen binding of FIT1-Ig as measured by Biacore. The top panel of FIG. 3 shows the results of the Biacore binding assay in which FIT1-Ig was first saturated by IL-17, followed by IL-20. The bottom panel of FIG. 3 shows the results of the Biacore assay in which FIT1-Ig was first saturated by IL-20, followed by IL-17.

In addition, tetravalent dual-specific antigen binding of FIT-Ig was also analyzed by Biacore. FIT1-Ig was first captured via a goat anti-human Fc antibody on the Biacore sensor chip, and the first antigen was injected and a binding signal observed. As the FIT1-Ig was saturated by the first antigen, the second antigen was then injected and the second signal observed. This was done either by first injecting IL-17 then IL-20 or by first injecting IL-20 followed by IL-17 for FIT2-Ig (FIG. 3). In either sequence, a dual-binding activity was detected, and both antigen binding was saturated at 25-30 RU. Similar results were obtained for FIT2-Ig and FIT3-Ig. Thus each FIT-Ig was able to bind both antigens simultaneously as a dual-specific tetravalent molecule.

The expression profile and dual-binding properties of FIT-Ig clearly demonstrated that, within the FIT-Ig molecule, both VL-CL paired correctly with their corresponding VH-CH1 to form 2 functional binding domains, and expressed as a single monomeric, tetravalent, and bispecific full length FIT-Ig protein. This is in contrast to the multivalent antibody type of molecules (Miller and Presta, U.S. Pat. No. 8,722,859), which displayed tetravalent but monospecific binding activities to one target antigen.

Example 1.4. Determination of Biological Activity of Anti-IL-17/IL-20 FIT-Ig The biological activity of FIT-Ig to neutralize IL-17 function was measured using GROα bioassay. Briefly, Hs27 cells were seeded at 10000 cells/50 µL/well into 96 well plates. FIT-Ig or anti-IL-17 control antibody (25 µL) were added in duplicate wells, with starting concentration at 2.5 nM followed by 1:2 serial dilutions until 5 pM. IL-17A (25 µL) was then added to each well. The final concentration of IL-17A was 0.3 nM. Cells were incubated at 37° C. for 17 h before cell culture supernatant were collected. Concentrations of GRO-α in cell culture supernatants were measured by human CACL1/GRO alpha Quantikine kit according to the manufacturer's protocol (R&D systems).

The biological activity of FIT-Ig to neutralize IL-20 function was measured using IL-20R+ BAF3 cell proliferation assay. Briefly, 25 µL of recombinant human IL-20 at 0.8 nM was added to each well of 96-well plates (the final concentration of IL-20 is 0.2 nM). Anti-IL20 antibody or FIT-Ig or other control antibody were diluted to 400 nM (working concentration was 100 nM) followed by 5-fold serial dilutions and were added to 96-well assay plates (25 µL per well). BaF3 cells stably transfected with IL-20 receptor were then added to each well at concentration of 10000 cell/well in volume of 50 μL RPMI 1640 plus 10% FBS, Hygromycin B at the concentration of 800 μg/ml, G418 at the concentration of 800 μg/ml. After 48-hr incubation, 100 μL CellTiter-Glo Luminescent buffer were added to each well. Contents were mixed for 2 minutes on an orbital shaker to induce cell lysis and plates were incubated at room temperature for 10 minutes to stabilize luminescent signal. Luminescence was recorded by SpectraMax M5.

As shown in Table 5, all FIT-Igs were able to neutralize both hIL-20 and hIL-17, with affinities similar to that of the paternal antibodies. Based on functional analysis using both Biacore and cell-based neutralization assays, it appears that all 3 FIT-Igs fully retain the activities of the parental mAbs. There was no significant functional differences among the three FIT-Igs, indicating that the linker was optional, and that FIT-Ig construct provided sufficient flexibility and special dimension to allow dual binding in the absence of a peptide spacer between the 2 Fab binding regions. This is in contrast to DVD-Ig type of molecules, where a linker between the 2 variable domains on each of the 2 polypeptide chain is required for retaining activities of the lower ($2^{nd}$) variable domain.

Example 1.5. Stability Study of Anti-IL-17/IL-20 FIT-Ig

FIT1-Ig protein samples in citrate buffer (pH=6.0) were individually incubated at constant 4° C., 25° C. and 40° C. for 1 day, 3 days or 7 days; Similarly, FIT1-Ig protein samples were freeze-thawed once, twice or three times. The fractions of intact full monomeric protein of all samples was detected by SEC-HPLC, with 10 μg of each protein sample injected into Ultimate 3000 HPLC equipping Superdex200 5/150 GL at flow rate 0.3 mL/min for 15 min, and data was recorded and analyzed using Chromeleon software supplied by the manufacturer. Table 6 shows that FIT1-Ig and FIT3-Ig remained full intact monomeric molecule under these thermo-challenged conditions.

TABLE 6

Stability analysis of FIT-Ig by measuring % full monomeric fractions by SEC

| Temp. (° C.) | Time (day) | FIT1-Ig | FIT3-Ig |
| --- | --- | --- | --- |
| 4 | 0 (Starting) | 98.74 | 98.60 |
|  | 1 | 98.09 | 97.78 |
|  | 3 | 97.81 | 97.45 |
|  | 7 | 97.63 | 97.65 |
| 25 | 1 | 99.00 | 98.26 |
|  | 3 | 99.00 | 98.01 |
|  | 7 | 98.86 | 98.53 |
| 40 | 1 | 98.95 | 98.50 |
|  | 3 | 98.94 | 98.35 |
|  | 7 | 98.82 | 98.37 |
|  | 1X freeze-thaw | 98.89 | 98.21 |
|  | 2X freeze-thaw | 95.37 | 98.21 |
|  | 3X freeze-thaw | 95.24 | 98.35 |

Example 1.6. Solubility Study of Anti-IL-17/IL-20 FIT-Ig

Figure 4:
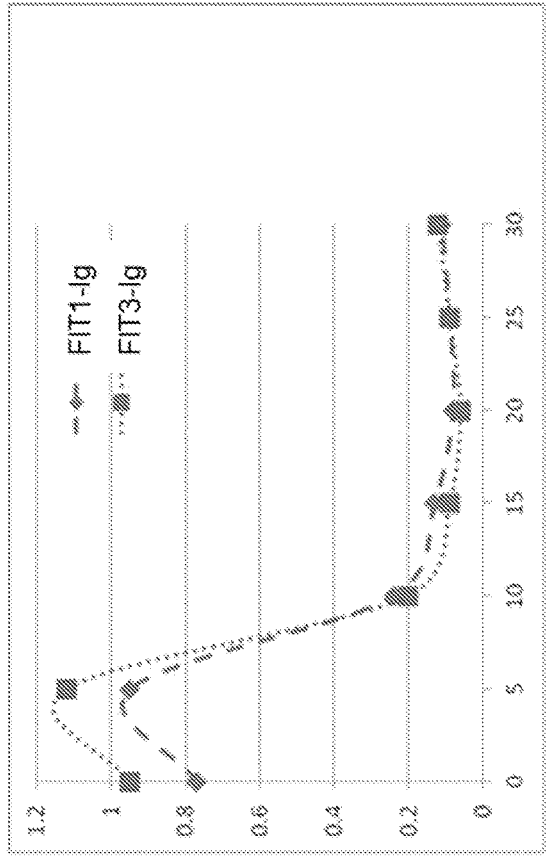
FIG. 4. Shows the solubility at a range of pH of anti-IL-17/IL-20 FIT Ig or monoclonal antibody rituximab, as measured by PEG-induced precipitation.
Figure 4:
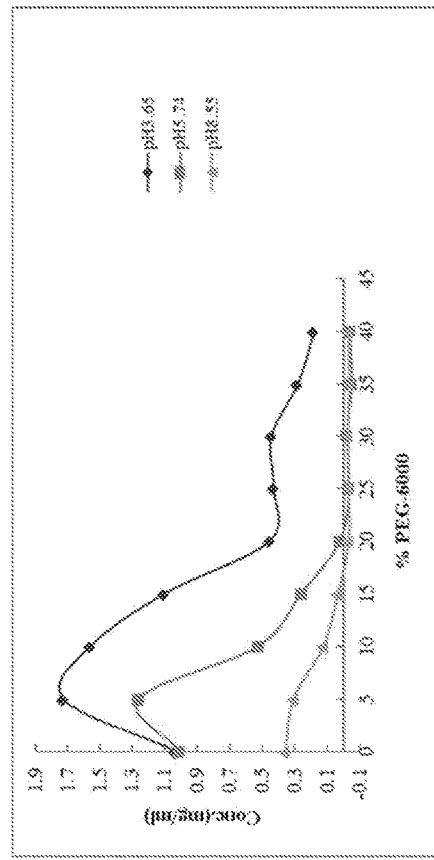

The solubility of FIT1-Ig was analyzed by measuring sign of precipitation in the presence of increasing concentration of PEG6000 (PEG6000 was purchased from Shanghai lingfeng chemical reagent co. Ltd). Briefly, solubility of protein in the presence of PEG6000 was obtained as a function of PEG6000 concentration (0, 5%, 10%, 15%, 20%, 25% and 30%). The solubility studies were conducted at a temperature of 25° C. at a solution pH of 6.0. Briefly, protein was precipitated by mixing appropriate quantities of buffered stock solutions of the protein, PEG and the buffer to get the desired concentration of the components. The final volume was made up to 200 μl and the concentration of protein was set at 1.0 mg/mL. The final solutions were mixed well and equilibrated for 16 h. After equilibration, the solutions were centrifuged at 13000 rpm for 10 min to separate the protein precipitate. Protein solubility was measured at 280 nm using Spectra Max Plus384 (Molecular Device) and obtained from the absorbance of the supernatant, and calculating the concentration based on standard curve of protein concentration (FIG. 4A). We also analyzed a commercial antibody Rituxan using the same experimental method under 3 different pH conditions (FIG. 4B). It appears that the protein solubility is dependent on the pH conditions, and that the predicted solubility of FIT-Ig would be in the range of monoclonal antibodies.

Example 1.7. Pharmacokinetic Study of Anti-IL-17/IL-20 FIT-Ig

Pharmacokinetic properties of FIT1-Ig were assessed in male Sprague-Dawley (SD) rats. FIT-Ig proteins were administered to male SD rats at a single intravenous dose of 5 mg/kg via a jugular cannula or subcutaneously under the dorsal skin. Serum samples were collected at different time points over a period of 28 days with sampling at 0, 5, 15, and 30 min; 1, 2, 4, 8, and 24 hr; and 2, 4, 7, 10, 14, 21, and 28 day serial bleeding via tail vein, and analyzed by human IL-17 capture and/or human IL-20 capture ELISAs. Briefly, ELISA plates were coated with goat anti-biotin antibody (5 μg/ml, 4° C., overnight), blocked with Superblock (Pierce), and incubated with biotinylated human IL-17 (IL-17 capture ELISA) or IL-20 (IL-20 capture ELISA) at 50 ng/ml in 10% Superblock TTBS at room temperature for 2 h. Serum samples were serially diluted (0.5% serum, 10% Superblock in TTBS) and incubated on the plate for 30 min at room temperature. Detection was carried out with HRP-labeled goat anti human antibody and concentrations were determined with the help of standard curves using the four parameter logistic fit. Several animals, especially in the subcutaneous group, showed a sudden drop in FIT-Ig concentrations following day 10, probably due to developing an anti-human response. These animals were eliminated from the final calculations. Values for the pharmacokinetic parameters were determined by non-compartmental model using WinNonlin software (Pharsight Corporation, Mountain View, Calif.).

The rat PK study, FIT1-Ig serum concentrations were very similar when determined by the two different ELISA methods, indicating that the molecule was intact, and capable of binding both antigens in vivo. Upon IV dosing, FIT1-Ig exhibited a bi-phasic pharmacokinetic profile, consisting of a distribution phase followed by an elimination phase, similar to the PK profile of conventional IgG molecules. The pharmacokinetic parameters calculated based on the two different analytical methods were very similar and are shown in Table 7. Clearance of FIT-Ig was low (~12 mL/day/kg), with low volumes of distribution (Vss~130 mL/kg) resulting in a long half-life (T1/2>10 days). Following subcutaneous administration, FIT-Ig absorbed slowly, with maximum serum concentrations of approximately 26.9 μg/ml reached at 4 days post-dose. The terminal half-life was about 11 days and the subcutaneous bioavailability was close to 100%. As demonstrated by these results, the properties of FIT1-Ig are very similar to a conventional IgG molecule in vivo, indicating a potential for therapeutic applications using comparable dosing regimens.

The pharmacokinetics study of FIT-Ig has demonstrated a surprising breakthrough in the field of multi-specific Ig-like biologics development. The rat pharmacokinetic system is commonly used in the pharmaceutical industry for preclinical evaluation of therapeutic mAbs, and it well predicts the pharmacokinetic profile of mAbs in humans. The long half-life and low clearance of FIT-Ig will enable its therapeutic utility for chronic indications with less frequent dosing, similar to a therapeutic mAb. In addition, FIT-Ig, being 100-kDa larger than an IgG, seemed to penetrate efficiently into the tissues based on its IgG-like volume of distribution parameter from the PK study.

TABLE 7

Pharmacokinetics analysis of FIT1-Ig in SD Rats

| Unit | IV PK parameters | | | | |
|---|---|---|---|---|---|
| | CL mL/day/kg | Vss mL/kg | Beta $t_{1/2}$ Day | AUC Day*µg/mL | MRT Day |
| IL-17 ELISA | 12.2 | 131 | 10.8 | 411 | 10.7 |
| IL-20 ELISA | 11.9 | 128 | 10.8 | 421 | 10.7 |

| Unit | SC PK parameters | | | | | |
|---|---|---|---|---|---|---|
| | $T_{max}$ Day | $C_{max}$ ug/mL | $t_{1/2}$ Day | $AUC_{INF}$ day*ug/mL | CL/F mL/day/kg | F % |
| IL-17 ELISA | 4.00 | 26.9 | 11.0 | 406 | 12.4 | 103.5 |
| IL-20 ELISA | 4.00 | 23.1 | 10.4 | 350 | 14.3 | 86.4 |

Example 1.8. Stable CHO Cell Line Development Studies of FIT-Ig

It has been observed that FIT-Ig was efficiently expressed in transiently-transfected 293E cells. In order to further determine the manufacturing feasibility of FIT-Ig, stable transfections were carried out in both CHO-DG44 and CHO-S cell lines, and subsequent clone selections as well as productivity analysis were performed. Briefly, CHO cells were transfected by electroporation with $8 \times 10^6$ cells in 400 µl transfection solution plus 20 ug DNA (for CHO DG44 cells) or 25 µg DNA (for CHO-S cells) subcloned in Freedom pCHO vector (Life Technologies). The stable cell line selection was done using routine procedures. Briefly, for CHO-DG44 selection, upon transfection, stable pool was selected (HT/2P/400G, where P is µg/mL Puromycin, G is µg/mL G418), and protein production was analyzed by IgG ELISA. Top pools were selected and proceed to amplification for several rounds with increasing concentration of MTX (50, 100, 200 and 500 nM), followed by analysis of protein production by IgG ELISA. The top pools were then selected for subcloning. For CHO-S cell selection, the first phase selection was performed in medium containing 10P/400G/100M (M is nM MTX), followed by analysis of protein production. Then the top pools were selected and proceed to $2^{nd}$ phase selection in either 30P/400G/500M or 50P/400G/1000M, followed by protein production measurement by ELISA. The top pools were then selected for subcloning. For protein productivity analysis, fully recovered cell pools (viability >90%) were seeded at $5 \times 10^5$ viable cells/mL (CHO DG44) or $3 \times 10^5$ viable cells/mL (CHO-S) using 30 mL fresh medium (CD FortiCHO™ medium supplemented with 6 mM L-glutamine) in 125-mL shake flasks. The cells were incubated on a shaking platform at 37° C., 80% relative humidity, 8% CO2, and 130 rpm. Sample cultures daily or at regular intervals (e.g., on day 0, 3, 5, 7, 10, 12, and 14) to determine the cell density, viability, and productivity until culture viability drops below 50% or day 14 of culture is reached. After sampling, feed the cultures with glucose as needed.

Figure 5:
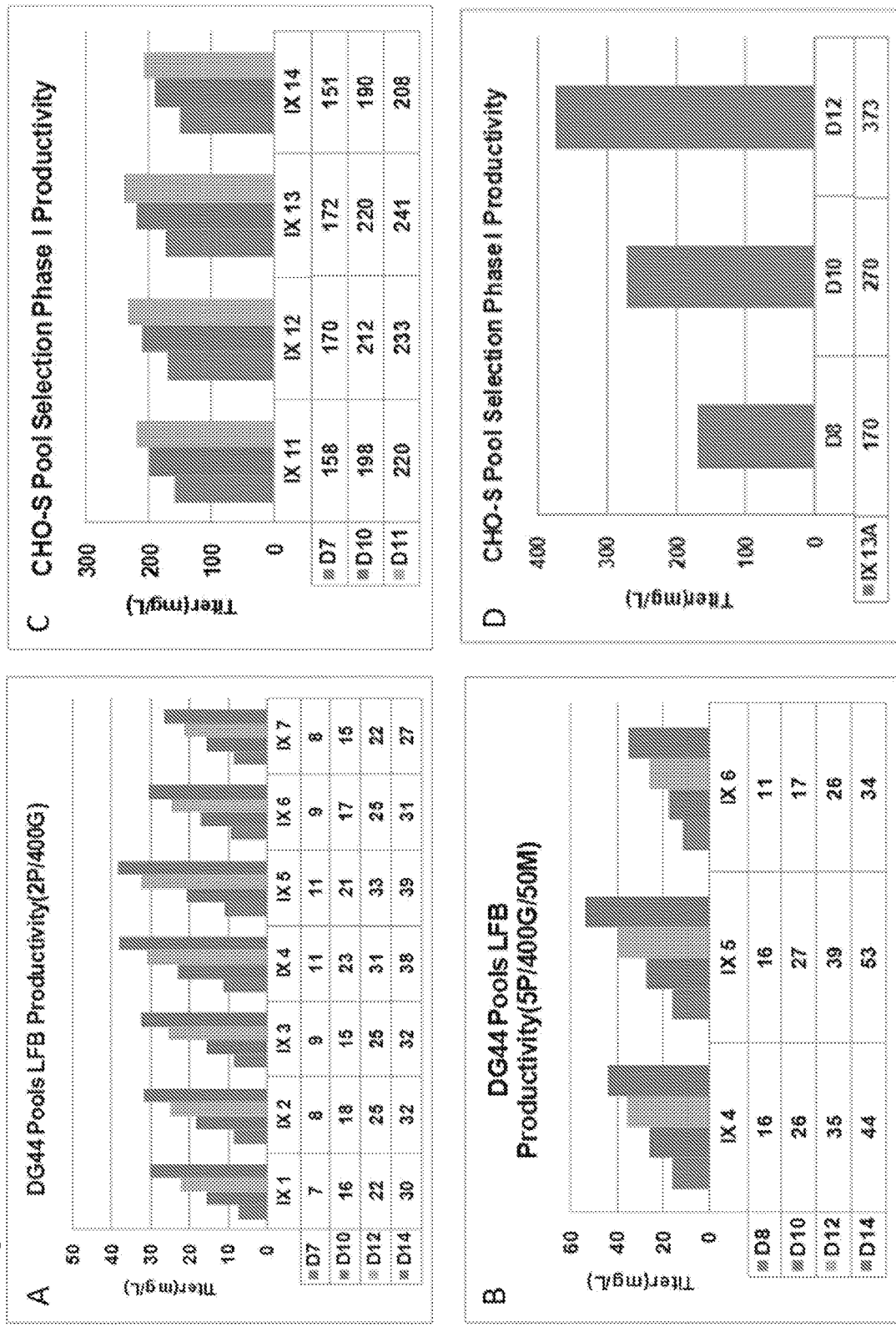
FIG. 5 shows the stability of stable CHO cell line development in both DG44 (5A and 5B) and CHO-S (5C and 5D) systems.

The overall process of FIT1-Ig CHO stable cell line development showed features similar to that of a monoclonal antibody development in CHO cells. For example, during DG44 pool analysis under 2P/400G, the VCD continued to increase until day 10-12 up to about 1.3E7, whereas cell viability remained above 80% up to day 13-14, and the productivity reached almost 40 mg/mL on day 14 (FIG. 5A). Upon amplification at 5P/400G/50M, productivity reached above 50 mg/mL on day 14 (FIG. 5B). For CHO-S cell selection, the titer reached above 200 mg/mL during the phase 1 selection (FIG. 5C), and above 370 mg/mL at the phase 2 selection (FIG. 5D). These levels of productivity are similar to what have been previously observed for regular human mAb development is our laboratory, suggesting that FIT-Ig display mAb-like manufacturing feasibility for commercial applications.

Example 2. Construction, Expression, and Purification of Anti-CD3/CD20 Fabs-in-Tandem Immunoglobulin (FIT-Ig)

To demonstrate if a FIT-Ig can bind to cell surface antigens, we have generated an anti-CD3/CD20 FIT-Ig molecule FIT7-Ig and FIT8-Ig, which is the 3-polypeptide construct, as shown in FIG. 1. The construct used to generate FIT-Ig capable of binding cell surface CD3 and CD20 is illustrated in FIG. 1B. Briefly, parental mAbs include two high affinity antibodies, anti-CD3 (OKT3) and anti-CD20 (Ofatumumab). To generate FIT7-Ig construct #1, the VL-CL of OKT3 was fused directly (FIT7-Ig) or through a linker of 7 amino acids linker (FIT8-Ig) to the N-terminus of the Ofatumumab heavy chain (as shown in Table 8). The construct #2 is VH-CH1 of OKT3 and the $3^{rd}$ construct is VL-CL of Ofatumumab. The 3 constructs for FIT-Ig were co-transfected in 293 cells, resulting in the expression and secretion of FIT-Ig proteins. The detailed procedures of the PCR cloning are described below:

Example 2.1. Molecular Cloning of Anti-CD3/CD20 FIT-Ig

The molecular cloning method is similar as that for anti-hIL-17/hIL-20 FIT-Ig.

TABLE 8

Anti-CD3/CD20 FIT-Ig molecules and constructs.

| FIT-Ig molecule | Construct #1 | Linker | Construct #2 | Construct #3 |
|---|---|---|---|---|
| FIT7-Ig | $VL_{CD3}$-CL-$VH_{CD20}$-CH1-Fc | No linker | $VH_{CD3}$-CH1 | $VL_{CD20}$-CL |
| FIT8-Ig | $VL_{CD3}$-CL-linker-$VH_{CD20}$-CH1-Fc | GGGGSGS | $VH_{CD3}$-CH1 | $VL_{CD20}$-CL |

Table 9 shows sequences of PCR primers used for molecular construction above.

TABLE 9

PCR primers used for molecular construction of anti-IL-17/IL-20 FIT-Igs

| | SEQ ID NO. |
|---|---|
| P4: GTCTGCGGCCGCTCATTTACCCGGAGACAGGGAGAG | 32 |
| P12: TCGAGCGGCCGCTCAACAAGATTTGGGCTCAACTTTCTTG | 33 |
| P20: CAGGTCCAGCTGCAGCAGTCTG | 34 |
| P22: GCCTGCGAAGTCACCCATCAGGGCCTGAGCTCGCCCGTCACAAAGAGCTTCAACAGGGG | 35 |
| P23: TACGAGAAACACAAAGTCTACGCCTGCGAAGTCACCCATCAGGGCCTGAG | 36 |
| P24: TGACGCTGAGCAAAGCAGACTACGAGAAACACAAAGTCTACGCCTGCGAA | 37 |

TABLE 9-continued

PCR primers used for molecular construction of anti-IL-17/IL-20 FIT-Igs

| | SEQ ID NO. |
|---|---|
| P25: CTCGCCCGTCACAAAGAGCTTCAACAGGGGAGAGTGTGAAGTGCAGCTGGTGGAGTCTG | 38 |
| P28: GCTGCTGCTGTGGTTCCCCGGCTCGCGATGCGAAATTGTGTTGACACAGTC | 39 |
| P29: AAGATGAAGCAGATGGTGCAGCCACCGTACGTTTAATCTCCAGTCGTGTCC | 40 |

The final sequences of anti-CD3/CD20 FIT-Ig are described in Table 10.

TABLE 10

Amino acid sequences of anti-CD3/CD20 FIT-Ig

| Protein | Protein region | Sequence Identifier | Sequence 12345678901234567890 |
|---|---|---|---|
| OKT3/Ofatumumab FIT7-Ig POLYPEPTIDE #1 | | SEQ ID NO.: 41 | QIVLTQSPAIMSASPGEKVTMTCSASSSVSYMNWYQQKSGTSPKRWIYDTSKLASGVPAHFRGSGSGTSYSLTISGMEAEDAATYYCQQWSSNPFTFGSGTKLEINRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK* |
| | OKT3 VL | SEQ ID NO.: 42 | QIVLTQSPAIMSASPGEKVTMTCSASSSVSYMNWYQQKSGTSPKRWIYDTSKLASGVPAHFRGSGSGTSYSLTISGMEAEDAATYYCQQWSSNPFTFGSGTKLEIN |
| | CL | SEQ ID NO.: 17 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Linker | | none |
| | Ofatumumab VH | SEQ ID NO.: 43 | EVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSS |
| | CH1 | SEQ ID NO.: 19 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Fc | SEQ ID NO.: 20 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK* |

TABLE 10-continued

Amino acid sequences of anti-CD3/CD20 FIT-Ig

| Protein | Protein region | Sequence Identifier | Sequence 12345678901234567890 |
|---|---|---|---|
| OKT3/Ofatumumab FIT7-Ig POLYPEPTIDE #2 | | SEQ ID NO.: 44 | QVQLQQSGAELARPGASVKMSCKASGYTFTRYTMH WVKQRPGQGLEWIGYINPSRGYTNYNQKFKDKATL TTDKSSSTAYMQLSSLTSEDSAVYYCARYYDDHYC LDYWGQGTTLTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC |
| | OKT3 VH | SEQ ID NO.: 45 | QVQLQQSGAELARPGASVKMSCKASGYTFTRYTMH WVKQRPGQGLEWIGYINPSRGYTNYNQKFKDKATL TTDKSSSTAYMQLSSLTSEDSAVYYCARYYDDHYC LDYWGQGTTLTVSS |
| | CH1 | SEQ ID NO.: 19 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSC |
| OKT3/Ofatumumab FIT7-Ig POLYPEPTIDE #3 | | SEQ ID NO.: 46 | EIVLTQSPATLSLSPGERATLSCRASQSVSSYLAW YQQKPGQAPRLLIYDASNRATGIPARFSGSGSGTD FTLTISSLEPEDFAVYYCQQRSNWPITFGQGTRLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC* |
| | Ofatumumab VL | SEQ ID NO.: 47 | EIVLTQSPATLSLSPGERATLSCRASQSVSSYLAW YQQKPGQAPRLLIYDASNRATGIPARFSGSGSGTD FTLTISSLEPEDFAVYYCQQRSNWPITFGQGTRLE IK |
| | CL | SEQ ID NO.: 17 | RTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC* |
| OKT3/Ofatumumab FIT8-Ig POLYPEPTIDE #1 | | SEQ ID NO.: 48 | QIVLTQSPAIMSASPGEKVTMTCSASSSVSYMNWY QQKSGTSPKRWIYDTSKLASGVPAHFRGSGSGTSY SLTISGMEAEDAATYYCQQWSSNPFTFGSGTKLEI NRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GECGGGGSGSEVQLVESGGGLVQPGRSLRLSCAAS GFTFNDYAMHWVRQAPGKGLEWVSTISWNSGSIGY ADSVKGRFTISRDNAKKSLYLQMNSLRAEDTALYY CAKDIQYGNYYYGMDVWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCDK THTCPPCPAPELLGGPSVFLFPPKPKDTLMISRTP EVTCVVVDVSHEDPEVKFNWYVDGVEVHNAKTKPR EEQYNSTYRVVSVLTVLHQDWLNGKEYKCKVSNKA LPAPIEKTISKAKGQPREPQVYTLPPSREEMTKNQ VSLTCLVKGFYPSDIAVEWESNGQPENNYKTTPPV LDSDGSFFLYSKLTVDKSRWQQGNVFSCSVMHEAL HNHYTQKSLSLSPGK* |
| | OKT3 VL | SEQ ID NO.: 42 | QIVLTQSPAIMSASPGEKVTMTCSASSSVSYMNWY QQKSGTSPKRWIYDTSKLASGVPAHFRGSGSGTSY SLTISGMEAEDAATYYCQQWSSNPFTFGSGTKLEI N |
| | CL | SEQ ID NO.: 17 | RTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |
| | Linker | SEQ ID NO.: 28 | GGGGSGS |
| | Ofatumumab VH | | EVQLVESGGGLVQPGRSLRLSCAASGFTFNDYAMH WVRQAPGKGLEWVSTISWNSGSIGYADSVKGRFTI SRDNAKKSLYLQMNSLRAEDTALYYCAKDIQYGNY YYGMDVWGQGTTVTVSS |
| | CH1 | SEQ ID NO.: 19 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSC |
| | Fc | SEQ ID NO.: 20 | DKTHTCPPCPAPELLGGPSVFLFPPKPKDTLMISR TPEVTCVVVDVSHEDPEVKFNWYVDGVEVHNAKT PREEQYNSTYRVVSVLTVLHQDWLNGKEYKCKVSN KALPAPIEKTISKAKGQPREPQVYTLPPSREEMTK NQVSLTCLVKGFYPSDIAVEWESNGQPENNYKTTP PVLDSDGSFFLYSKLTVDKSRWQQGNVFSCSVMHE ALHNHYTQKSLSLSPGK* |

TABLE 10-continued

Amino acid sequences of anti-CD3/CD20 FIT-Ig

| Protein | Protein region | Sequence Identifier | Sequence 12345678901234567890 |
|---|---|---|---|
| OKT3/Ofatumumab FIT8-Ig POLYPEPTIDE #2 | | SEQ ID NO.: 44 | QVQLQQSGAELARPGASVKMSCKASGYTFTRYTMH WVKQRPGQGLEWIGYINPSRGYTNYNQKFKDKATL TTDKSSSTAYMQLSSLTSEDSAVYYCARYYDDHYC LDYWGQGTTLTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC |
| | OKT3 VH | SEQ ID NO.: 45 | QVQLQQSGAELARPGASVKMSCKASGYTFTRYTMH WVKQRPGQGLEWIGYINPSRGYTNYNQKFKDKATL TTDKSSSTAYMQLSSLTSEDSAVYYCARYYDDHYC LDYWGQGTTLTVSS |
| | CH1 | SEQ ID NO.: 19 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSC |
| OKT3/Ofatumumab FIT8-Ig POLYPEPTIDE #3 | | SEQ ID NO.: 46 | EIVLTQSPATLSLSPGERATLSCRASQSVSSYLAW YQQKPGQAPRLLIYDASNRATGIPARFSGSGSGTD FTLTISSLEPEDFAVYYCQQRSNWPITFGQGTRLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC* |
| | Ofatumumab VL | SEQ ID NO.: 47 | EIVLTQSPATLSLSPGERATLSCRASQSVSSYLAW YQQKPGQAPRLLIYDASNRATGIPARFSGSGSGTD FTLTISSLEPEDFAVYYCQQRSNWPITFGQGTRLE IK |
| | CL | SEQ ID NO.: 17 | RTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC* |

Example 2.2. Expression and Purification of Anti-CD3/CD20 FIT-Ig

All DNA constructs of each FIT-Ig were subcloned into pBOS based vectors, and sequenced to ensure accuracy. Construct #1, #2, and #3 of each FIT-Ig were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells ($1.0$-$1.2 \times 10^6$/ml, cell viability >95%) at 60 μg DNA/120 ml culture. After 6-24 hours culture in shaker, add peptone to the transfected cells at a final concentration of 5%, with shaking at 125 rpm/min., at 37° C., 8% $CO_2$. On the 6th-7th day, supernatant was harvested by centrifugation and filtration, and FIT-Ig protein purified using protein A chromatography (Pierce, Rockford, Ill.) according to manufacturer's instructions. The proteins were analyzed by SDS-PAGE and their concentration determined by A280 and BCA (Pierce, Rockford, Ill.) (Table 11).

TABLE 11

Expression and SEC analysis of anti-CD3/CD20 FIT-Ig proteins

| FIT-Ig protein | DNA ratio: Construct 1:2:3 | Expression level (mg/L) | % Peak monomeric fraction by SEC |
|---|---|---|---|
| FIT7-Ig | 1:3:3 | 21.3 | 99.53 |
| FIT8-Ig | 1:3:3 | 25.6 | 99.16 |

Example 2.3. Binding Activities of Anti-CD3/CD20 FIT-Ig Molecules

Binding of anti-CD3/CD20 FIT-Igs to both targets were analyzed by FACS, using Jurkat cells that express CD3 on the cell surface, as well as Raji cells that express CD20 on the cell surface. Briefly, $5 \times 10^5$ cells were washed in ice-cold PBS and blocked with 2% FBS on ice for 1 hr. Cells were incubated with antibody, FIT-Ig (100 nM), or isotype control on ice for 1 hr and washed 3 times with PBS. Secondary antibody (goat anti-human IgG labeled with Alexa Fluor 488, Invitrogen) were added and incubated with cells on ice for 1 hr in dark followed by three times wash with PBS. Samples were analyzed in FACs caliber. The cell surface binding shows that both FIT7-Ig and FIT8-Ig were able to binding to both cell surface antigens CD3 and CD20 in a concentration dependent manner. Compared to the binding activities of the parental mAbs, FIT-Ig showed a reduced binding intensity to CD3 on Jurkat cells, but an enhanced binding intensity to CD20 on Raji cells. In all binding studies, FIT7-Ig and FIT8-Ig showed similar binding activities to both antigens, indicating the linker did not make a significant impact on its binding ability for FIT8-Ig (Table 12).

TABLE 12

Cell surface antigen binding studies of anti-CD3/CD20 FIT-Ig proteins

| FIT-Ig protein | Antigen (cell line) | Binding Intensity by FACS (MFI) |
|---|---|---|
| OKT3 | CD3 (Jurkat) | 399 |
| FIT7-Ig | | 159 |
| FIT8-Ig | | 211 |
| Ofatumumab | CD20 (Raji) | 181 |
| FIT7-Ig | | 291 |
| FIT8-Ig | | 274 |

Example 3. Construction, Expression, and Purification of Anti-TNF/IL-17 Fabs-in-Tandem Immunoglobulin (FIT-Ig)

Another FIT-Ig that can bind to human IL-17 and human TNFα (FIT9-Ig) was also generated using anti-IL-17 mAb clone LY, and anti-TNF mAb Golimumab, in the 3-polypeptide construct, as shown in FIG. 1. To generate FIT9-Ig construct #1, the VL-CL of Golimumab was fused directly to the N-terminus of LY heavy chain (as shown in Table 13). The construct #2 is VH-CH1 of Golimumab and the 3$^{rd}$ construct is VL-CL of LY. The 3 constructs for FIT9-Ig were co-transfected in 293 cells, resulting in the expression and secretion of FIT9-Ig proteins. The final sequences of anti-TNF/IL-17 FIT-Ig are described in Table 14.

Example 3.1. Molecular Cloning of Anti-TNF/IL-17 FIT-Ig

The molecular cloning method is similar as that for anti-hIL-17/hIL-20 FIT-Ig.

TABLE 13

Anti-TNF/IL-17 FIT-Ig molecule and constructs.

| FIT-Ig molecule | Construct #1 | Linker | Construct #2 | Construct #3 |
|---|---|---|---|---|
| FIT9-Ig | VL$_{TNF}$-CL-VH$_{IL-17}$-CH1-Fc | No linker | VH$_{TNF}$-CH1 | VL$_{IL-17}$-CL |

TABLE 14

Amino acid sequences of anti-TNF/IL-17 FIT-Ig molecules

| Protein | Protein region | Sequence Identifier | Sequence 12345678901234567890 |
|---|---|---|---|
| Anti-IL-TNF/IL-17 FIT9-Ig POLYPEPTIDE #1 | | SEQ ID NO.: 87 | EIVLTQSPATLSLSPGER ATLSCRASQSVYSYLA WYQQKPGQAPRLLIYD ASNRATGIPARFSGSGS GTDFTLTISSLEPEDFAV YYCQQRSNWPPFTFGP GTKVDIKRTVAAPSVFI FPPSDEQLKSGTASVVC LLNNFYPREAKVQWKV DNALQSGNSQESVTEQ DSKDSTYSLSSTLTLSK ADYEKHKVYACEVTH QGLSSPVTKSFNRGECQ VQLVQSGAEVKKPGSS VKVSCKASGYSFTDYHI HWVRQAPGQGLEWMG VINPMYGTTDYNQRFK GRVTITADESTSTAYME LSSLRSEDTAVYYCAR YDYFTGTGVYWGQGT LVTVSSASTKGPSVFPL APSSKSTSGGTAALGCL VKDYFPEPVTVSWNSG ALTSGVHTFPAVLQSSG LYSLSSVVTVPSSSLGT QTYICNVNHKPSNTKV DKKVEPKSCDKTHTCP PCPAPELLGGPSVFLFPP KPKDTLMISRTPEVTCV VVDVSHEDPEVKFNWY VDGVEVHNAKTKPREE QYNSTYRVVSVLTVLH QDWLNGKEYKCKVSN KALPAPIEKTISKAKGQ PREPQVYTLPPSREEMT KNQVSLTCLVKGFYPS DIAVEWESNGQPENNY KTTPPVLDSDGSFFLYS KLTVDKSRWQQGNVFS CSVMHEALHNHYTQKS LSLSPGK* |
| | GOLIMUMAB VL | SEQ ID NO.: 88 | EIVLTQSPATLSLSPGER ATLSCRASQSVYSYLA WYQQKPGQAPRLLIYD ASNRATGIPARFSGSGS GTDFTLTISSLEPEDFAV YYCQQRSNWPPFTFGP GTKVDIK |
| | CL | SEQ ID NO.: 17 | RTVAAPSVFIFPPSDEQL KSGTASVVCLLNNFYP REAKVQWKVDNALQS GNSQESVTEQDSKDST YSLSSTLTLSKADYEKH KVYACEVTHQGLSSPV TKSFNRGEC |

TABLE 14-continued

Amino acid sequences of anti-TNF/IL-17 FIT-Ig molecules

| Protein | Protein region | Sequence Identifier | Sequence 12345678901234567890 |
|---|---|---|---|
| | Linker | | None |
| | LY VH | SEQ ID NO.: 22 | QVQLVQSGAEVKKPGS SVKVSCKASGYSFTDY HIHWVRQAPGQGLEW MGVINPMYGTTDYNQR FKGRVTITADESTSTAY MELSSLRSEDTAVYYC ARYDYFTGTGVYWGQ GTLVTVSS |
| | CH1 | SEQ ID NO.: 19 | ASTKGPSVFPLAPSSKS TSGGTAALGCLVKDYF PEPVTVSWNSGALTSG VHTFPAVLQSSGLYSLS SVVTVPSSSLGTQTYIC NVNHKPSNTKVDKKVE PKSC |
| | Fc | SEQ ID NO.: 20 | DKTHTCPPCPAPELLGG PSVFLFPPKPKDTLMISR TPEVTCVVVDVSHEDP EVKFNWYVDGVEVHN AKTKPREEQYNSTYRV VSVLTVLHQDWLNGKE YKCKVSNKALPAPIEKT ISKAKGQPREPQVYTLP PSREEMTKNQVSLTCL VKGFYPSDIAVEWESN GQPENNYKTTPPVLDS DGSFFLYSKLTVDKSR WQQGNVFSCSVMHEA LHNHYTQKSLSLSPGK* |
| Anti-TNF/IL-17 FIT9-Ig POLYPEPTIDE #2 | | SEQ ID NO.: 89 | QVQLVESGGGVVQPGR SLRLSCAASGFIFSSYA MHWVRQAPGNGLEWV AFMSYDGSNKKYADSV KGRFTISRDNSKNTLYL QMNSLRAEDTAVYYC ARDRGIAAGGNYYYYG MDVWGQGTTVTVSSA STKGPSVFPLAPSSKSTS GGTAALGCLVKDYFPE PVTVSWNSGALTSGVH TFPAVLQSSGLYSLSSV VTVPSSSLGTQTYICNV NHKPSNTKVDKKVEPK SC |
| | GOLIMUMAB VH | SEQ ID NO.: 90 | QVQLVESGGGVVQPGR SLRLSCAASGFIFSSYA MHWVRQAPGNGLEWV AFMSYDGSNKKYADSV KGRFTISRDNSKNTLYL QMNSLRAEDTAVYYC ARDRGIAAGGNYYYYG MDVWGQGTTVTVSS |
| | CH1 | SEQ ID NO.: 19 | ASTKGPSVFPLAPSSKS TSGGTAALGCLVKDYF PEPVTVSWNSGALTSG VHTFPAVLQSSGLYSLS SVVTVPSSSLGTQTYIC NVNHKPSNTKVDKKVE PKSC |
| Anti-IL-TNF/IL-17 FIT9-Ig POLYPEPTIDE #3 | | SEQ ID NO.: 91 | DIVMTQTPLSLSVTPGQ PASISCRSSRSLVHSRG NTYLHWYLQKPGQSPQ LLIYKVSNRFIGVPDRFS GSGSGTDFTLKISRVEA EDVGVYYCSQSTHLPF TFGQGTKLEIKRTVAAP SVFIFPPSDEQLKSGTAS VVCLLNNFYPREAKVQ WKVDNALQSGNSQESV TEQDSKDSTYSLSSTLT |

TABLE 14-continued

Amino acid sequences of anti-TNF/IL-17 FIT-Ig molecules

| Protein | Protein region | Sequence Identifier | Sequence 12345678901234567890 |
|---------|----------------|---------------------|-------------------------------|
|         |                |                     | LSKADYEKHKVYACEV THQGLSSPVTKSFNRGE C* |
|         | LY VL          | SEQ ID NO.: 16      | DIVMTQTPLSLSVTPGQ PASISCRSSRSLVHSRG NTYLHWYLQKPGQSPQ LLIYKVSNRFIGVPDRFS GSGSGTDFTLKISRVEA EDVGVYYCSQSTHLPF TFGQGTKLEIK |
|         | CL             | SEQ ID NO.: 17      | RTVAAPSVFIFPPSDEQL KSGTASVVCLLNNFYP REAKVQWKVDNALQS GNSQESVTEQDSKDST YSLSSTLTLSKADYEKH KVYACEVTHQGLSSPV TKSFNRGEC * |

Example 3.2. Expression, Purification, and Analysis of Anti-TNF/IL-17 FIT-Ig Proteins All DNA constructs of each FIT-Ig were subcloned into pBOS based vectors, and sequenced to ensure accuracy. Construct #1, #2, and #3 of FIT9-Ig were transiently co-expressed using Polyethyleneimine (PEI) in 293E cells as described previously and FIT9-Ig proteins were purified by protein A chromatography. The expression level was 10-23 mg/L. The purified protein was subjected to functional analysis using cell-based assays for IL-17 (production of GROα by Hs27 cells) and TNF (production of IL-8 by L929 cells). The neutralization potency of FIT9-Ig against human TNF was 11.6 pM (compared to 15.9 pM by Golimumab in the same experiment), as against human IL-17 was 122 pM (compared to 51.5 pM by LY in the same experiment). Overall FIT9-Ig maintained the biological activities of the parental mAbs.

Example 4. Construction, Expression, and Purification of Anti-CTLA-4/PD-1 Fabs-in-Tandem Immunoglobulin (FIT-Ig)

Another FIT-Ig that can bind to human CTLA-4 and human PD-1 (FIT10-Ig) was generated using anti-CTLA-4 mAb Ipilimumab, and anti-PD-1 mAb Nivolumab, in the 3-polypeptide construct, as shown in FIG. 1. To generate FIT10-Ig construct #1, the VL-CL of Ipilimumab was fused directly to the N-terminus of Nivolumab heavy chain (as shown in Table 15). The construct #2 is VH-CH1 of Ipilimumab and the $3^{rd}$ construct is VL-CL of Nivolumab. The 3 constructs for FIT10-Ig were co-transfected in 293 cells, resulting in the expression and secretion of FIT10-Ig proteins.

Example 4.1. Molecular Cloning of Anti-CTLA-4/PD-1 FIT-Ig

The molecular cloning method is similar as that for anti-hIL-17/hIL-20 FIT-Ig. The final sequences of anti-CTLA-4/PD-1 FIT-Ig are described in Table 16.

TABLE 15

Anti-CTLA-4/PD-1 FIT-Ig molecule and constructs.

| FIT-Ig molecule | Construct #1 | Linker | Construct #2 | Construct #3 |
|-----------------|--------------|--------|--------------|--------------|
| FIT10-Ig | $VL_{CTLA-4}$-CL-$VH_{PD-1}$-CH1-Fc | No linker | $VH_{CTLA-4}$-CH1 | $VL_{PD-1}$-CL |

TABLE 16

Amino acid sequences of anti-CTLA-4/PD-1 FIT-Ig molecules

| Protein | Protein region | Sequence Identifier | Sequence 12345678901234567890 |
|---------|----------------|---------------------|-------------------------------|
| Anti-CTLA-4/PD-1 FIT10-Ig POLYPEPTIDE #1 |  | SEQ ID NO.: 92 | EIVLTQSPGTLSLSPGER ATLSCRASQSVGSSYLA WYQQKPGQAPRLLIYG AFSRATGIPDRFSGSGS GTDFTLTISRLEPEDFA VYYCQQYGSSPWTFGQ GTKVEIKRTVAAPSVFI FPPSDEQLKSGTASVVC LLNNFYPREAKVQWKV DNALQSGNSQESVTEQ DSKDSTYSLSSTLTLSK ADYEKHKVYACEVTH QGLSSPVTKSFNRGECQ VQLVESGGGVVQPGRS LRLDCKASGITFSNSGM |

TABLE 16-continued

Amino acid sequences of anti-CTLA-4/PD-1 FIT-Ig molecules

| Protein | Protein region | Sequence Identifier | Sequence 12345678901234567890 |
|---|---|---|---|
| | | | HWVRQAPGKGLEWVA |
| | | | VIWYDGSKRYYADSVK |
| | | | GRFTISRDNSKNTLFLQ |
| | | | MNSLRAEDTAVYYCAT |
| | | | NDDYWGQGTLVTVSS |
| | | | ASTKGPSVFPLAPSSKS |
| | | | TSGGTAALGCLVKDYF |
| | | | PEPVTVSWNSGALTSG |
| | | | VHTFPAVLQSSGLYSLS |
| | | | SVVTVPSSSLGTQTYIC |
| | | | NVNHKPSNTKVDKKVE |
| | | | PKSCDKTHTCPPCPAPE |
| | | | LLGGPSVFLFPPKPKDT |
| | | | LMISRTPEVTCVVVDVS |
| | | | HEDPEVKFNWYVDGV |
| | | | EVHNAKTKPREEQYNS |
| | | | TYRVVSVLTVLHQDWL |
| | | | NGKEYKCKVSNKALPA |
| | | | PIEKTISKAKGQPREPQ |
| | | | VYTLPPSREEMTKNQV |
| | | | SLTCLVKGFYPSDIAVE |
| | | | WESNGQPENNYKTTPP |
| | | | VLDSDGSFFLYSKLTVD |
| | | | KSRWQQGNVFSCSVM |
| | | | HEALHNHYTQKSLSLSP |
| | | | GK* |
| | IPILIMUMAB VL | SEQ ID NO.: 93 | EIVLTQSPGTLSLSPGER |
| | | | ATLSCRASQSVGSSYLA |
| | | | WYQQKPGQAPRLLIYG |
| | | | AFSRATGIPDRFSGSGS |
| | | | GTDFTLTISRLEPEDFA |
| | | | VYYCQQYGSSPWTFGQ |
| | | | GTKVEIK |
| | CL | SEQ ID NO.: 17 | RTVAAPSVFIFPPSDEQL |
| | | | KSGTASVVCLLNNFYP |
| | | | REAKVQWKVDNALQS |
| | | | GNSQESVTEQDSKDST |
| | | | YSLSSTLTLSKADYEKH |
| | | | KVYACEVTHQGLSSPV |
| | | | TKSFNRGEC |
| | Linker | | None |
| | NIVOLUMAB VH | SEQ ID NO.: 94 | QVQLVESGGGVVQPGR |
| | | | SLRLDCKASGITFSNSG |
| | | | MHWVRQAPGKGLEWV |
| | | | AVIWYDGSKRYYADSV |
| | | | KGRFTISRDNSKNTLFL |
| | | | QMNSLRAEDTAVYYC |
| | | | ATNDDYWGQGTLVTV |
| | | | SS |
| | CH1 | SEQ ID NO.: 19 | ASTKGPSVFPLAPSSKS |
| | | | TSGGTAALGCLVKDYF |
| | | | PEPVTVSWNSGALTSG |
| | | | VHTFPAVLQSSGLYSLS |
| | | | SVVTVPSSSLGTQTYIC |
| | | | NVNHKPSNTKVDKKVE |
| | | | PKSC |
| | Fc | SEQ ID NO.: 20 | DKTHTCPPCPAPELLGG |
| | | | PSVFLFPPKPKDTLMISR |
| | | | TPEVTCVVVDVSHEDP |
| | | | EVKFNWYVDGVEVHN |
| | | | AKTKPREEQYNSTYRV |
| | | | VSVLTVLHQDWLNGKE |
| | | | YKCKVSNKALPAPIEKT |
| | | | ISKAKGQPREPQVYTLP |
| | | | PSREEMTKNQVSLTCL |
| | | | VKGFYPSDIAVEWESN |
| | | | GQPENNYKTTPPVLDS |
| | | | DGSFFLYSKLTVDKSR |
| | | | WQQGNVFSCSVMHEA |
| | | | LHNHYTQKSLSLSPGK* |

TABLE 16-continued

Amino acid sequences of anti-CTLA-4/PD-1 FIT-Ig molecules

| Protein | Protein region | Sequence Identifier | Sequence |
|---|---|---|---|
| Anti-CTLA-4/PD-1 FIT10-Ig POLYPEPTIDE #2 | | SEQ ID NO.: 95 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | IPILIMUMAB VH | SEQ ID NO.: 96 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| | CH1 | SEQ ID NO.: 19 | ASTKGPSVFPLAPSSKSTSGGTAALGCLVKDYFPEPVTVSWNSGALTSGVHTFPAVLQSSGLYSLSVVTVPSSSLGTQTYICNVNHKPSNTKVDKKVEPKSC |
| Anti-CTLA-4/PD-1 FIT10-Ig POLYPEPTIDE #3 | | SEQ ID NO.: 97 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| | Nivolumab VL | SEQ ID NO.: 98 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | CL | SEQ ID NO.: 17 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |

Figure 6:
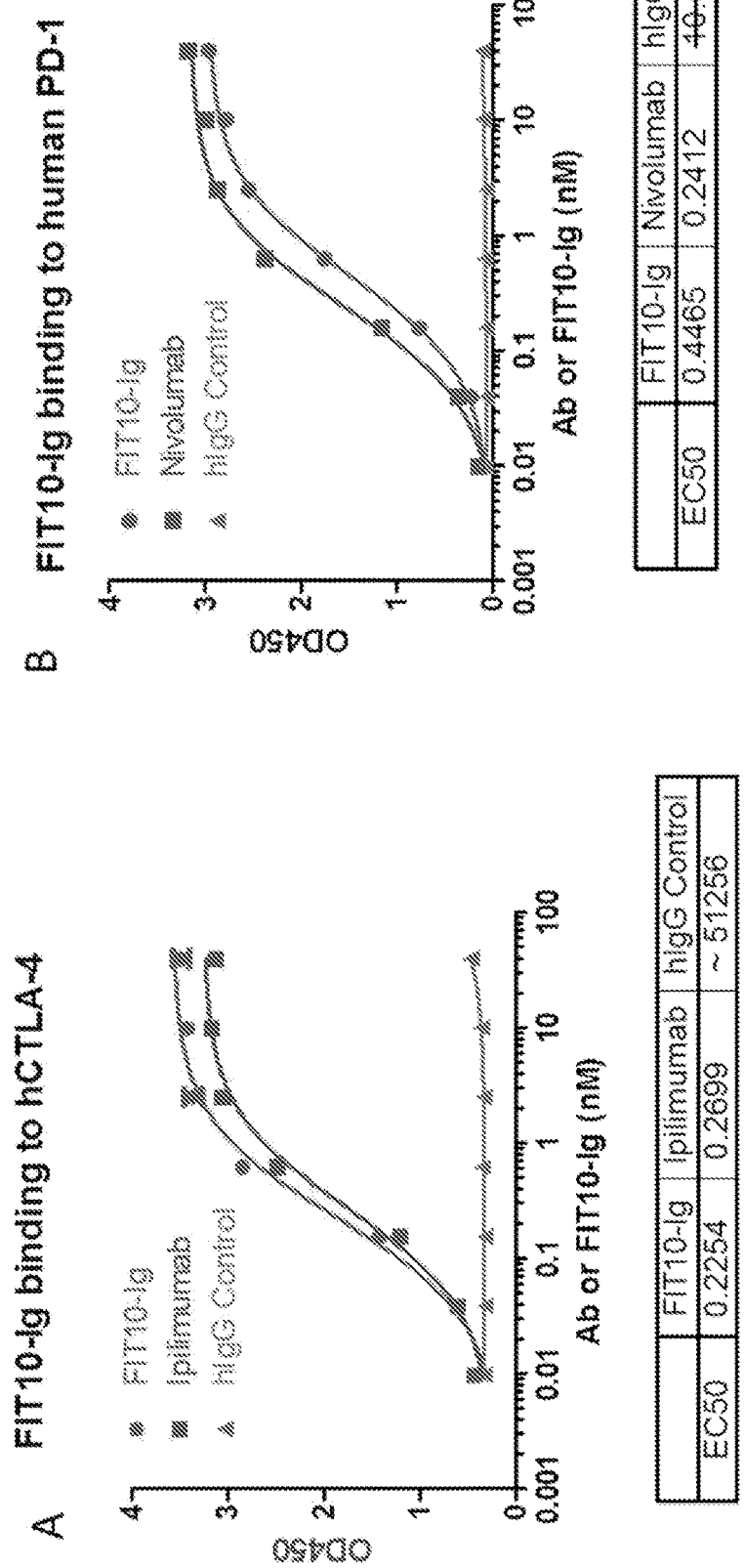
FIG. 6 shows the binding to CTLA-4 (6A) or PD-1 (FIG. 6B) by FIT10-Ig or the parental antibodies Ipilimumab and Nivolumab, as assessed by ELISA.

Example 4.2. Expression, Purification, and Functional Analysis of Anti-CTLA-4/PD-1 FIT-Ig Proteins All DNA constructs of each FIT-Ig were subcloned into pBOS based vectors, and sequenced to ensure accuracy. Construct #1, #2, and #3 of FIT10-Ig were transiently co-expressed using Polyethyleneimine (PEI) in 293E cells as described previously and FIT9-Ig proteins were purified by protein A chromatography to 98% monomeric full protein. The expression levels were up to 43 mg/L. The purified protein was subjected to binding analysis using ELISA against recombinant CTLA-4Ig and PD-1. Briefly, for binding to CTLA-4, human CTLA-4Ig (R&D Systems) was immobilized on 96-well plates, followed by routine wash and blocking procedures. Then FIT-10-Ig or Ipilimumab at various concentrations were added to the plate, followed by incubation and multiple wash steps, and detected with anti-human Fab-HRP. For binding to PD-1, human PD-1 (with a his tag) (R&D Systems) was immobilized on 96-well plates, followed by routine wash and blocking procedures. Then FIT-10-Ig or Nivolumab at various concentrations were added to the plate, followed by incubation and multiple wash steps, and detected with anti-human Fc-HRP (FIG. 6). It appears that FIT10-Ig was able to bind both CTLA-4 (A)

and PD-1 (B) with similar activities as the parental mAbs Ipilimumab and Nivolumab, respectively.

Figure 7:
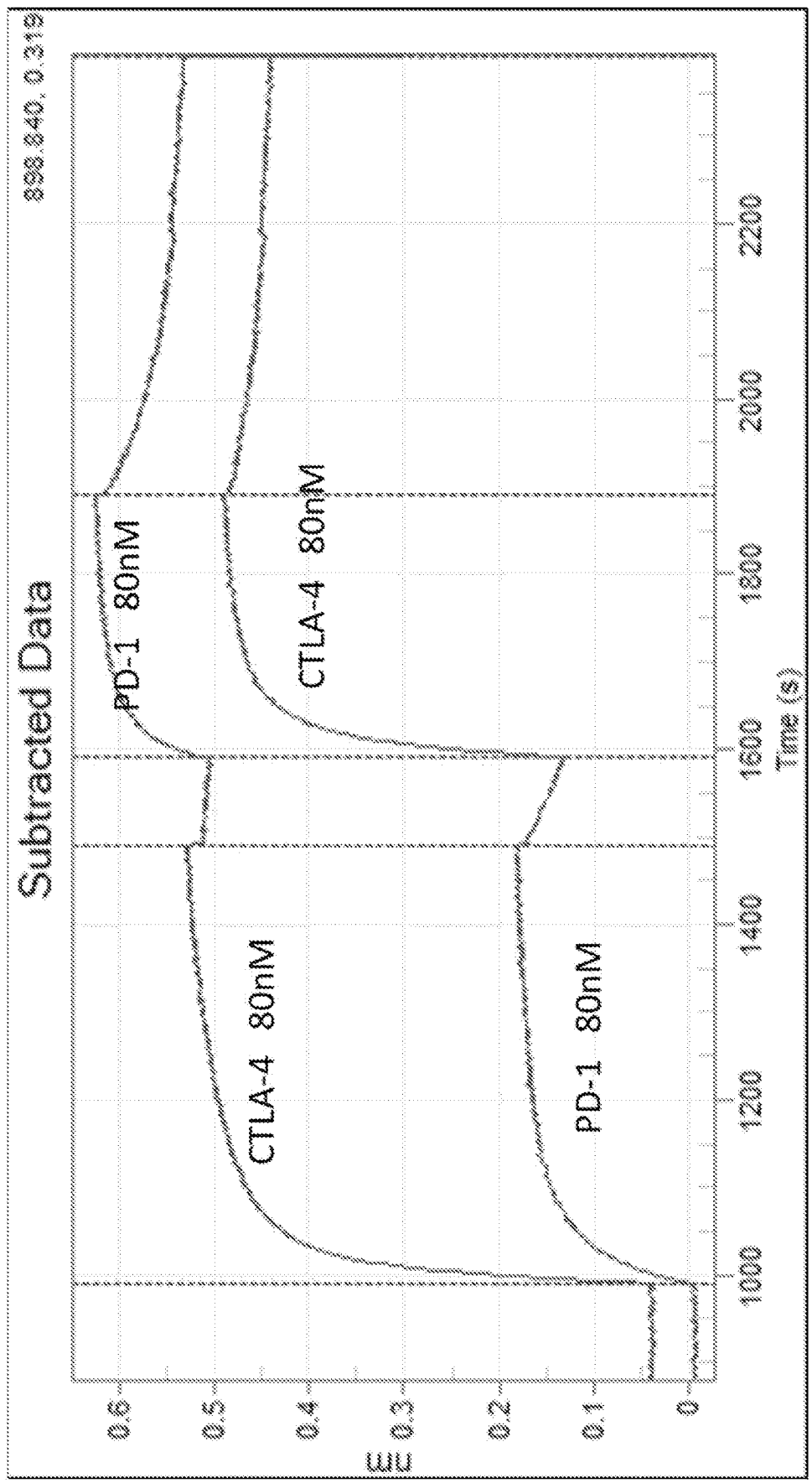
FIG. 7 shows a multiple binding study of FIT10-Ig against both CTLA-4 and PD-1. Binding to CTLA-4 followed by PD-1; and binding by PD-1 followed by CTLA-4 are both shown as indicated in FIG. 7.

In addition, multiple-antigen binding study was done using OctetRed to determine if FIT10-Ig was able to bind recombinant CTLA-4 and PD-1 simultaneously. Briefly, FIT10-Ig was immobilize on AR2G sensor at concentration of 10 μg/ml, followed by binding of CTLA-4Ig and then PD-1 (or PD-1 first, then CTLA-4Ig) in assay buffer (PBS pH 7.4, 0.1% BSA, 0.02% Tween), with concentration at 80 nM. At the end of the experiment, the surface was regenerated with 10 mM glycine at pH1.5 five times (FIG. 7). This experiment shows that FIT10-Ig was able to bind PD-1 when it had already bound to CTLA-4, and vice versa, indicating that FIT10-Ig was able to bind both CTLA-4Ig and PD-1 simultaneously.

All publications, patent applications, and issued patents cited in this specification are herein incorporated by reference as if each individual publication, patent application, or issued patent were specifically and individually indicated to be incorporated by reference in its entirety.

What is claimed is:

1. A binding protein comprising three polypeptide chains, wherein:
- the first polypeptide chain comprises, from amino to carboxyl terminus, either (i) $VL_A$-CL-$VH_B$-CH1-Fc, wherein CL is fused directly to $VH_B$, or (ii) $VH_B$-CH1-$VL_A$-CL-Fc, wherein CH1 is fused directly to $VL_A$, and wherein there are no linkers inserted between the variable domains and constant domains;
- wherein the second polypeptide chain comprises, from amino to carboxyl terminus, $VH_A$-CH1, wherein there is no linker inserted between $VH_A$ and CH1; and
- wherein the third polypeptide chain comprises, from amino to carboxyl terminus, $VL_B$-CL, wherein there is no linker inserted between $VL_B$ and CL;
- wherein the binding protein is capable of binding two or more epitopes or antigens, wherein VL is a light chain variable domain, CL is a light chain constant domain, VH is a heavy chain variable domain, CH1 is a first constant domain of a heavy chain, A is a first epitope or antigen, and B is a second epitope or antigen, and wherein A and B are different epitopes of the same antigen or are different antigens; and
- wherein, on expression in a mammalian host cell, two of said first polypeptide chains, two of said second polypeptide chains, and two of said third polypeptide chains associate to provide a monomeric, tetravalent, and bispecific binding protein comprising six polypeptide chains, having four functional Fab binding regions, and wherein said binding protein binds both epitope or antigen A and epitope or antigen B.

2. The binding protein of claim 1, wherein the binding protein is capable of binding one or more epitopes on CTLA-4, one or more epitopes on PD-1, or at least one epitope on CTLA-4 and at least one epitope on PD-1.

3. The binding protein of claim 1, wherein, in said first polypeptide chain, the segment $VL_A$-CL is the light chain variable and light chain constant domains of a parental antibody recognizing epitope or antigen A and the segment $VH_B$-CH1 is the heavy chain variable and heavy chain constant domains of a parental antibody recognizing epitope or antigen B, wherein said second polypeptide chain $VH_A$-CH1 is the heavy chain variable and heavy chain constant domains of a parental antibody recognizing epitope or antigen A; and wherein said third polypeptide chain $VL_B$-CL is the light chain of a parental antibody recognizing epitope or antigen B.

* * * * *

SEQUENCE LISTING

```
<160> NUMBER OF SEQ ID NOS: 98

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 1
caggtgcagc tggtgcagag cggcgccgaa g                               31

<210> SEQ ID NO 2
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 2
gctggacctg agagcctgaa ccgccaccac cacactctcc cctgttgaag c          51

<210> SEQ ID NO 3
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 3
ggtggtggcg gttcaggctc tcaggtccag cttgtgcaat ctggcgccga gg         52

<210> SEQ ID NO 4
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 4
gtctgcggcc gctcatttac ccggagacag ggagag                          36

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 5
taagcgtacg gtggctgcac catctgtctt c                               31

<210> SEQ ID NO 6
<211> LENGTH: 59
<212> TYPE: DNA
```

<213> ORGANISM: Artificial Sequence
<220> FEATURE:
<223> OTHER INFORMATION: Oligonucleotide primer

<400> SEQUENCE: 6
cggcgccaga ttgcacaagc tggacctggc ctgaaccaca ctctccctg ttgaagctc    59

<210> SEQ ID NO 7
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 7
gctggacctg agagcctgaa ccgccaccac cacactctcc cctgttgaag c    51

<210> SEQ ID NO 8
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 8
ggtggtggcg gttcaggctc tcaggtccag cttgtgcaat ctggcgccga gg    52

<210> SEQ ID NO 9
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 9
tacctcggcg ccagattgca caagctggac ctgacactct ccctgttga agctctttg    59

<210> SEQ ID NO 10
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 10
catgacacct taacagaggc cccaggtcgt tttacctcgg cgccagattg cacaag    56

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 11
caataagctt tacatgacac cttaacagag gccccag    37

<210> SEQ ID NO 12
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 12
tcgagcggcc gctcaacaag atttgggctc aactttcttg    40

<210> SEQ ID NO 13
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 13
gctgctgctg tggttccccg gctcgcgatg cgctatacag ttgacacagt c        51

<210> SEQ ID NO 14
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 14
gaagatgaag acagatggtg cagccaccgt acgcttgatc tctacctttg ttc       53

<210> SEQ ID NO 15
<211> LENGTH: 676
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 15

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gln Val Gln Leu Val
    210                 215                 220

Gln Ser Gly Ala Glu Val Lys Arg Pro Gly Ala Ser Val Lys Val Ser
225                 230                 235                 240

Cys Lys Ala Ser Gly Tyr Thr Phe Thr Asn Asp Ile Ile His Trp Val
```

-continued

```
                245                 250                 255
Arg Gln Ala Pro Gly Gln Arg Leu Glu Trp Met Gly Trp Ile Asn Ala
            260                 265                 270
Gly Tyr Gly Asn Thr Gln Tyr Ser Gln Asn Phe Gln Asp Arg Val Ser
            275                 280                 285
Ile Thr Arg Asp Thr Ser Ala Ser Thr Ala Tyr Met Glu Leu Ile Ser
            290                 295                 300
Leu Arg Ser Glu Asp Thr Ala Val Tyr Tyr Cys Ala Arg Glu Pro Leu
305                 310                 315                 320
Trp Phe Gly Glu Ser Ser Pro His Asp Tyr Tyr Gly Met Asp Val Trp
                325                 330                 335
Gly Gln Gly Thr Thr Val Thr Val Ser Ser Ala Ser Thr Lys Gly Pro
            340                 345                 350
Ser Val Phe Pro Leu Ala Pro Ser Ser Lys Ser Thr Ser Gly Gly Thr
            355                 360                 365
Ala Ala Leu Gly Cys Leu Val Lys Asp Tyr Phe Pro Glu Pro Val Thr
            370                 375                 380
Val Ser Trp Asn Ser Gly Ala Leu Thr Ser Gly Val His Thr Phe Pro
385                 390                 395                 400
Ala Val Leu Gln Ser Ser Gly Leu Tyr Ser Leu Ser Ser Val Val Thr
                405                 410                 415
Val Pro Ser Ser Ser Leu Gly Thr Gln Thr Tyr Ile Cys Asn Val Asn
            420                 425                 430
His Lys Pro Ser Asn Thr Lys Val Asp Lys Lys Val Glu Pro Lys Ser
            435                 440                 445
Cys Asp Lys Thr His Thr Cys Pro Pro Cys Pro Ala Pro Glu Leu Leu
            450                 455                 460
Gly Gly Pro Ser Val Phe Leu Phe Pro Pro Lys Pro Lys Asp Thr Leu
465                 470                 475                 480
Met Ile Ser Arg Thr Pro Glu Val Thr Cys Val Val Val Asp Val Ser
                485                 490                 495
His Glu Asp Pro Glu Val Lys Phe Asn Trp Tyr Val Asp Gly Val Glu
            500                 505                 510
Val His Asn Ala Lys Thr Lys Pro Arg Glu Glu Gln Tyr Asn Ser Thr
            515                 520                 525
Tyr Arg Val Val Ser Val Leu Thr Val Leu His Gln Asp Trp Leu Asn
            530                 535                 540
Gly Lys Glu Tyr Lys Cys Lys Val Ser Asn Lys Ala Leu Pro Ala Pro
545                 550                 555                 560
Ile Glu Lys Thr Ile Ser Lys Ala Lys Gly Gln Pro Arg Glu Pro Gln
                565                 570                 575
Val Tyr Thr Leu Pro Pro Ser Arg Glu Glu Met Thr Lys Asn Gln Val
            580                 585                 590
Ser Leu Thr Cys Leu Val Lys Gly Phe Tyr Pro Ser Asp Ile Ala Val
            595                 600                 605
Glu Trp Glu Ser Asn Gly Gln Pro Glu Asn Asn Tyr Lys Thr Thr Pro
            610                 615                 620
Pro Val Leu Asp Ser Asp Gly Ser Phe Phe Leu Tyr Ser Lys Leu Thr
625                 630                 635                 640
Val Asp Lys Ser Arg Trp Gln Gln Gly Asn Val Phe Ser Cys Ser Val
                645                 650                 655
Met His Glu Ala Leu His Asn His Tyr Thr Gln Lys Ser Leu Ser Leu
            660                 665                 670
```

Ser Pro Gly Lys
        675

<210> SEQ ID NO 16
<211> LENGTH: 112
<212> TYPE: PRT
<213> ORGANISM: Homo sapiens

<400> SEQUENCE: 16

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 127
<212> TYPE: PRT
<213> ORGANISM: Mus sp.

<400> SEQUENCE: 18

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Asp
            20                  25                  30

Ile Ile His Trp Val Arg Gln Ala Pro Gly Gln Arg Leu Glu Trp Met
        35                  40                  45

```
Gly Trp Ile Asn Ala Gly Tyr Gly Asn Thr Gln Tyr Ser Gln Asn Phe
        50                  55                  60

Gln Asp Arg Val Ser Ile Thr Arg Asp Thr Ser Ala Ser Thr Ala Tyr
 65                  70                  75                  80

Met Glu Leu Ile Ser Leu Arg Ser Glu Asp Thr Ala Val Tyr Tyr Cys
                 85                  90                  95

Ala Arg Glu Pro Leu Trp Phe Gly Glu Ser Ser Pro His Asp Tyr Tyr
                100                 105                 110

Gly Met Asp Val Trp Gly Gln Gly Thr Thr Val Thr Val Ser Ser
            115                 120                 125
```

<210> SEQ ID NO 19
<211> LENGTH: 103
<212> TYPE: PRT
<213> ORGANISM: Homo sapiens

<400> SEQUENCE: 19

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100
```

<210> SEQ ID NO 20
<211> LENGTH: 227
<212> TYPE: PRT
<213> ORGANISM: Homo sapiens

<400> SEQUENCE: 20

```
Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 222
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 22
<211> LENGTH: 119
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
```

```
                1               5                   10                  15
            Ser Val Lys Val Ser Cys Lys Ala Ser Gly Tyr Ser Phe Thr Asp Tyr
                            20                  25                  30

His Ile His Trp Val Arg Gln Ala Pro Gly Gln Gly Leu Glu Trp Met
                            35                  40                  45

Gly Val Ile Asn Pro Met Tyr Gly Thr Thr Asp Tyr Asn Gln Arg Phe
                            50                  55                  60

Lys Gly Arg Val Thr Ile Thr Ala Asp Glu Ser Thr Ser Thr Ala Tyr
             65                 70                  75                  80

Met Glu Leu Ser Ser Leu Arg Ser Glu Asp Thr Ala Val Tyr Tyr Cys
                            85                  90                  95

Ala Arg Tyr Asp Tyr Phe Thr Gly Thr Gly Val Tyr Trp Gly Gln Gly
                            100                 105                 110

Thr Leu Val Thr Val Ser Ser
                            115
```

<210> SEQ ID NO 23
<211> LENGTH: 214
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 23

```
            Ala Ile Gln Leu Thr Gln Ser Pro Ser Ser Leu Ser Ala Ser Val Gly
              1               5                   10                  15

Asp Arg Val Thr Ile Thr Cys Arg Ala Ser Gln Gly Ile Ser Ser Ala
                            20                  25                  30

Leu Ala Trp Tyr Gln Gln Lys Pro Gly Lys Ala Pro Lys Leu Leu Ile
                            35                  40                  45

Tyr Asp Ala Ser Ser Leu Glu Ser Gly Val Pro Ser Arg Phe Ser Gly
                            50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Gln Gln Phe Asn Ser Tyr Pro Leu
                            85                  90                  95

Thr Phe Gly Gly Gly Thr Lys Val Glu Ile Lys Arg Thr Val Ala Ala
                            100                 105                 110

Pro Ser Val Phe Ile Phe Pro Pro Ser Asp Glu Gln Leu Lys Ser Gly
                            115                 120                 125

Thr Ala Ser Val Val Cys Leu Leu Asn Asn Phe Tyr Pro Arg Glu Ala
                            130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                            165                 170                 175

Ser Thr Leu Thr Leu Ser Lys Ala Asp Tyr Glu Lys His Lys Val Tyr
                            180                 185                 190

Ala Cys Glu Val Thr His Gln Gly Leu Ser Ser Pro Val Thr Lys Ser
                            195                 200                 205

Phe Asn Arg Gly Glu Cys
                            210
```

<210> SEQ ID NO 24
<211> LENGTH: 107
<212> TYPE: PRT

<213> ORGANISM: Mus sp.

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 25
<211> LENGTH: 679
<212> TYPE: PRT
<213> ORGANISM: Artificial Sequence
<220> FEATURE:
<223> OTHER INFORMATION: Anti-IL-17/IL-20 FIT2-Ig polypeptide

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Ser Gly Gln Val
    210                 215                 220

Gln Leu Val Gln Ser Gly Ala Glu Val Lys Arg Pro Gly Ala Ser Val
225                 230                 235                 240

-continued

```
Lys Val Ser Cys Lys Ala Ser Gly Tyr Thr Phe Thr Asn Asp Ile Ile
                245                 250                 255
His Trp Val Arg Gln Ala Pro Gly Gln Arg Leu Glu Trp Met Gly Trp
            260                 265                 270
Ile Asn Ala Gly Tyr Gly Asn Thr Gln Tyr Ser Gln Asn Phe Gln Asp
        275                 280                 285
Arg Val Ser Ile Thr Arg Asp Thr Ser Ala Ser Thr Ala Tyr Met Glu
    290                 295                 300
Leu Ile Ser Leu Arg Ser Glu Asp Thr Ala Val Tyr Cys Ala Arg
305                 310                 315                 320
Glu Pro Leu Trp Phe Gly Glu Ser Pro His Asp Tyr Tyr Gly Met
                325                 330                 335
Asp Val Trp Gly Gln Gly Thr Thr Val Thr Val Ser Ser Ala Ser Thr
            340                 345                 350
Lys Gly Pro Ser Val Phe Pro Leu Ala Pro Ser Ser Lys Ser Thr Ser
        355                 360                 365
Gly Gly Thr Ala Ala Leu Gly Cys Leu Val Lys Asp Tyr Phe Pro Glu
    370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                405                 410                 415
Val Val Thr Val Pro Ser Ser Ser Leu Gly Thr Gln Thr Tyr Ile Cys
            420                 425                 430
Asn Val Asn His Lys Pro Ser Asn Thr Lys Val Asp Lys Lys Val Glu
        435                 440                 445
Pro Lys Ser Cys Asp Lys Thr His Thr Cys Pro Pro Cys Pro Ala Pro
    450                 455                 460
Glu Leu Leu Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
            500                 505                 510
Gly Val Glu Val His Asn Ala Lys Thr Lys Pro Arg Glu Glu Gln Tyr
        515                 520                 525
Asn Ser Thr Tyr Arg Val Val Ser Val Leu Thr Val Leu His Gln Asp
    530                 535                 540
Trp Leu Asn Gly Lys Glu Tyr Lys Cys Lys Val Ser Asn Lys Ala Leu
545                 550                 555                 560
Pro Ala Pro Ile Glu Lys Thr Ile Ser Lys Ala Lys Gly Gln Pro Arg
                565                 570                 575
Glu Pro Gln Val Tyr Thr Leu Pro Pro Ser Arg Glu Glu Met Thr Lys
            580                 585                 590
Asn Gln Val Ser Leu Thr Cys Leu Val Lys Gly Phe Tyr Pro Ser Asp
        595                 600                 605
Ile Ala Val Glu Trp Glu Ser Asn Gly Gln Pro Glu Asn Asn Tyr Lys
    610                 615                 620
Thr Thr Pro Pro Val Leu Asp Ser Asp Gly Ser Phe Phe Leu Tyr Ser
625                 630                 635                 640
Lys Leu Thr Val Asp Lys Ser Arg Trp Gln Gln Gly Asn Val Phe Ser
                645                 650                 655
```

```
Cys Ser Val Met His Glu Ala Leu His Asn His Tyr Thr Gln Lys Ser
            660                 665                 670

Leu Ser Leu Ser Pro Gly Lys
        675

<210> SEQ ID NO 26
<211> LENGTH: 3
<212> TYPE: PRT
<213> ORGANISM: Artificial Sequence
<220> FEATURE:
<223> OTHER INFORMATION: peptide linker sequence

<400> SEQUENCE: 26

Gly Ser Gly
1

<210> SEQ ID NO 27
<211> LENGTH: 683
<212> TYPE: PRT
<213> ORGANISM: Artificial Sequence
<220> FEATURE:
<223> OTHER INFORMATION: Anti-IL-17/IL-20 FIT3-Ig polypeptide

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Ser Gln Val Gln Leu Val Gln Ser Gly Ala Glu Val Lys Arg Pro
225                 230                 235                 240

Gly Ala Ser Val Lys Val Ser Cys Lys Ala Ser Gly Tyr Thr Phe Thr
                245                 250                 255

Asn Asp Ile Ile His Trp Val Arg Gln Ala Pro Gly Gln Arg Leu Glu
            260                 265                 270
```

Trp Met Gly Trp Ile Asn Ala Gly Tyr Gly Asn Thr Gln Tyr Ser Gln
            275                 280                 285

Asn Phe Gln Asp Arg Val Ser Ile Thr Arg Asp Thr Ser Ala Ser Thr
        290                 295                 300

Ala Tyr Met Glu Leu Ile Ser Leu Arg Ser Glu Asp Thr Ala Val Tyr
305                 310                 315                 320

Tyr Cys Ala Arg Glu Pro Leu Trp Phe Gly Glu Ser Ser Pro His Asp
                325                 330                 335

Tyr Tyr Gly Met Asp Val Trp Gly Gln Gly Thr Thr Val Thr Val Ser
                340                 345                 350

Ser Ala Ser Thr Lys Gly Pro Ser Val Phe Pro Leu Ala Pro Ser Ser
            355                 360                 365

Lys Ser Thr Ser Gly Gly Thr Ala Ala Leu Gly Cys Leu Val Lys Asp
        370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Ser Ser Leu Gly Thr Gln
            420                 425                 430

Thr Tyr Ile Cys Asn Val Asn His Lys Pro Ser Asn Thr Lys Val Asp
        435                 440                 445

Lys Lys Val Glu Pro Lys Ser Cys Asp Lys Thr His Thr Cys Pro Pro
450                 455                 460

Cys Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
        675                 680

<210> SEQ ID NO 28
<211> LENGTH: 7
<212> TYPE: PRT
<213> ORGANISM: Artificial Sequence
<220> FEATURE:
<223> OTHER INFORMATION: peptide linker sequence

<400> SEQUENCE: 28

```
Gly Gly Gly Gly Ser Gly Ser
1               5
```

<210> SEQ ID NO 29
<211> LENGTH: 436
<212> TYPE: PRT
<213> ORGANISM: Artificial Sequence
<220> FEATURE:
<223> OTHER INFORMATION: Anti-IL-17/IL-20 FIT4-Ig polypeptide

<400> SEQUENCE: 29

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Ala Ile
    210                 215                 220

Gln Leu Thr Gln Ser Pro Ser Ser Leu Ser Ala Ser Val Gly Asp Arg
225                 230                 235                 240

Val Thr Ile Thr Cys Arg Ala Ser Gln Gly Ile Ser Ser Ala Leu Ala
                245                 250                 255

Trp Tyr Gln Gln Lys Pro Gly Lys Ala Pro Lys Leu Leu Ile Tyr Asp
            260                 265                 270

Ala Ser Ser Leu Glu Ser Gly Val Pro Ser Arg Phe Ser Gly Ser Gly
        275                 280                 285

Ser Gly Thr Asp Phe Thr Leu Thr Ile Ser Ser Leu Gln Pro Glu Asp
    290                 295                 300
```

```
Phe Ala Thr Tyr Tyr Cys Gln Gln Phe Asn Ser Tyr Pro Leu Thr Phe
305                 310                 315                 320

Gly Gly Gly Thr Lys Val Glu Ile Lys Arg Thr Val Ala Ala Pro Ser
            325                 330                 335

Val Phe Ile Phe Pro Pro Ser Asp Glu Gln Leu Lys Ser Gly Thr Ala
            340                 345                 350

Ser Val Val Cys Leu Leu Asn Asn Phe Tyr Pro Arg Glu Ala Lys Val
            355                 360                 365

Gln Trp Lys Val Asp Asn Ala Leu Gln Ser Gly Asn Ser Gln Glu Ser
            370                 375                 380

Val Thr Glu Gln Asp Ser Lys Asp Ser Thr Tyr Ser Leu Ser Ser Thr
385                 390                 395                 400

Leu Thr Leu Ser Lys Ala Asp Tyr Glu Lys His Lys Val Tyr Ala Cys
            405                 410                 415

Glu Val Thr His Gln Gly Leu Ser Ser Pro Val Thr Lys Ser Phe Asn
            420                 425                 430

Arg Gly Glu Cys
            435

<210> SEQ ID NO 30
<211> LENGTH: 439
<212> TYPE: PRT
<213> ORGANISM: Artificial Sequence
<220> FEATURE:
<223> OTHER INFORMATION: Anti-IL-17/IL-20 FIT5-Ig polypeptide

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
210                 215                 220
```

Gly Ala Ile Gln Leu Thr Gln Ser Pro Ser Ser Leu Ser Ala Ser Val
225                 230                 235                 240

Gly Asp Arg Val Thr Ile Thr Cys Arg Ala Ser Gln Gly Ile Ser Ser
            245                 250                 255

Ala Leu Ala Trp Tyr Gln Gln Lys Pro Gly Lys Ala Pro Lys Leu Leu
        260                 265                 270

Ile Tyr Asp Ala Ser Ser Leu Glu Ser Gly Val Pro Ser Arg Phe Ser
    275                 280                 285

Gly Ser Gly Ser Gly Thr Asp Phe Thr Leu Thr Ile Ser Ser Leu Gln
290                 295                 300

Pro Glu Asp Phe Ala Thr Tyr Tyr Cys Gln Gln Phe Asn Ser Tyr Pro
305                 310                 315                 320

Leu Thr Phe Gly Gly Gly Thr Lys Val Glu Ile Lys Arg Thr Val Ala
            325                 330                 335

Ala Pro Ser Val Phe Ile Phe Pro Pro Ser Asp Glu Gln Leu Lys Ser
        340                 345                 350

Gly Thr Ala Ser Val Val Cys Leu Leu Asn Asn Phe Tyr Pro Arg Glu
    355                 360                 365

Ala Lys Val Gln Trp Lys Val Asp Asn Ala Leu Gln Ser Gly Asn Ser
370                 375                 380

Gln Glu Ser Val Thr Glu Gln Asp Ser Lys Asp Ser Thr Tyr Ser Leu
385                 390                 395                 400

Ser Ser Thr Leu Thr Leu Ser Lys Ala Asp Tyr Glu Lys His Lys Val
            405                 410                 415

Tyr Ala Cys Glu Val Thr His Gln Gly Leu Ser Ser Pro Val Thr Lys
        420                 425                 430

Ser Phe Asn Arg Gly Glu Cys
            435

<210> SEQ ID NO 31
<211> LENGTH: 443
<212> TYPE: PRT
<213> ORGANISM: Artificial Sequence
<220> FEATURE:
<223> OTHER INFORMATION: Anti-IL-17/IL-20 FIT6-Ig polypeptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Phe Thr Gly Thr Gly Val Tyr Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
        210                 215                 220

Gly Gly Ser Gly Ser Ala Ile Gln Leu Thr Gln Ser Pro Ser Ser Leu
225                 230                 235                 240

Ser Ala Ser Val Gly Asp Arg Val Thr Ile Thr Cys Arg Ala Ser Gln
                245                 250                 255

Gly Ile Ser Ser Ala Leu Ala Trp Tyr Gln Gln Lys Pro Gly Lys Ala
            260                 265                 270

Pro Lys Leu Leu Ile Tyr Asp Ala Ser Ser Leu Glu Ser Gly Val Pro
        275                 280                 285

Ser Arg Phe Ser Gly Ser Gly Ser Gly Thr Asp Phe Thr Leu Thr Ile
290                 295                 300

Ser Ser Leu Gln Pro Glu Asp Phe Ala Thr Tyr Tyr Cys Gln Gln Phe
305                 310                 315                 320

Asn Ser Tyr Pro Leu Thr Phe Gly Gly Gly Thr Lys Val Glu Ile Lys
            325                 330                 335

Arg Thr Val Ala Ala Pro Ser Val Phe Ile Phe Pro Pro Ser Asp Glu
                340                 345                 350

Gln Leu Lys Ser Gly Thr Ala Ser Val Val Cys Leu Leu Asn Asn Phe
            355                 360                 365

Tyr Pro Arg Glu Ala Lys Val Gln Trp Lys Val Asp Asn Ala Leu Gln
        370                 375                 380

Ser Gly Asn Ser Gln Glu Ser Val Thr Glu Gln Asp Ser Lys Asp Ser
385                 390                 395                 400

Thr Tyr Ser Leu Ser Ser Thr Leu Thr Leu Ser Lys Ala Asp Tyr Glu
                405                 410                 415

Lys His Lys Val Tyr Ala Cys Glu Val Thr His Gln Gly Leu Ser Ser
            420                 425                 430

Pro Val Thr Lys Ser Phe Asn Arg Gly Glu Cys
        435                 440

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 32
gtctgcggcc gctcatttac ccggagacag ggagag                        36

<210> SEQ ID NO 33
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 33

-continued tcgagcggcc gctcaacaag atttgggctc aactttcttg　　　　　　　　　40

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 34
caggtccagc tgcagcagtc tg　　　　　　　　　　　　　　　　　　22

<210> SEQ ID NO 35
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 35
gcctgcgaag tcacccatca gggcctgagc tcgcccgtca caaagagctt caacagggg　　59

<210> SEQ ID NO 36
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 36
tacgagaaac acaaagtcta cgcctgcgaa gtcacccatc agggcctgag　　　　　　50

<210> SEQ ID NO 37
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 37
tgacgctgag caaagcagac tacgagaaac acaaagtcta cgcctgcgaa　　　　　　50

<210> SEQ ID NO 38
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 38
ctcgcccgtc acaaagagct tcaacagggg agagtgtgaa gtgcagctgg tggagtctg　59

<210> SEQ ID NO 39
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 39
gctgctgctg tggttccccg gctcgcgatg cgaaattgtg ttgacacagt c　　　　　51

<210> SEQ ID NO 40
<211> LENGTH: 52
<212> TYPE: DNA

```
<213> ORGANISM: Artificial Sequence
<220> FEATURE:
<223> OTHER INFORMATION: Oligonucleotide primer

<400> SEQUENCE: 40
aagatgaaga cagatggtgc agccaccgta cgtttaatct ccagtcgtgt cc          52

<210> SEQ ID NO 41
<211> LENGTH: 665
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 41
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Val Gln Leu Val Glu Ser Gly Gly Gly Leu
    210                 215                 220

Val Gln Pro Gly Arg Ser Leu Arg Leu Ser Cys Ala Ala Ser Gly Phe
225                 230                 235                 240

Thr Phe Asn Asp Tyr Ala Met His Trp Val Arg Gln Ala Pro Gly Lys
                245                 250                 255

Gly Leu Glu Trp Val Ser Thr Ile Ser Trp Asn Ser Gly Ser Ile Gly
            260                 265                 270

Tyr Ala Asp Ser Val Lys Gly Arg Phe Thr Ile Ser Arg Asp Asn Ala
        275                 280                 285

Lys Lys Ser Leu Tyr Leu Gln Met Asn Ser Leu Arg Ala Glu Asp Thr
    290                 295                 300

Ala Leu Tyr Tyr Cys Ala Lys Asp Ile Gln Tyr Gly Asn Tyr Tyr Tyr
305                 310                 315                 320

Gly Met Asp Val Trp Gly Gln Gly Thr Thr Val Thr Val Ser Ser Ala

```
                    325                 330                 335
Ser Thr Lys Gly Pro Ser Val Phe Pro Leu Ala Pro Ser Ser Lys Ser
                340                 345                 350

Thr Ser Gly Gly Thr Ala Ala Leu Gly Cys Leu Val Lys Asp Tyr Phe
            355                 360                 365

Pro Glu Pro Val Thr Val Ser Trp Asn Ser Gly Ala Leu Thr Ser Gly
370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Glu Glu Met
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665

<210> SEQ ID NO 42
<211> LENGTH: 106
<212> TYPE: PRT
<213> ORGANISM: Mus sp.

<400> SEQUENCE: 42

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30
```

```
Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 43
<211> LENGTH: 122
<212> TYPE: PRT
<213> ORGANISM: Homo sapiens

<400> SEQUENCE: 43

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 44
<211> LENGTH: 222
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 44

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
            210                 215                 220

<210> SEQ ID NO 45
<211> LENGTH: 119
<212> TYPE: PRT
<213> ORGANISM: Mus sp.

<400> SEQUENCE: 45

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 46
<211> LENGTH: 214
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95
```

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 107
<212> TYPE: PRT
<213> ORGANISM: Homo sapiens

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 48
<211> LENGTH: 672
<212> TYPE: PRT
<213> ORGANISM: Artificial Sequence
<220> FEATURE:
<223> OTHER INFORMATION: OKT3/Ofatumumab FIT8-Ig polypeptide

<400> SEQUENCE: 48

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

-continued

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Ser Glu Val Gln Leu
    210                 215                 220

Val Glu Ser Gly Gly Gly Leu Val Gln Pro Gly Arg Ser Leu Arg Leu
225                 230                 235                 240

Ser Cys Ala Ala Ser Gly Phe Thr Phe Asn Asp Tyr Ala Met His Trp
                245                 250                 255

Val Arg Gln Ala Pro Gly Lys Gly Leu Glu Trp Val Ser Thr Ile Ser
            260                 265                 270

Trp Asn Ser Gly Ser Ile Gly Tyr Ala Asp Ser Val Lys Gly Arg Phe
        275                 280                 285

Thr Ile Ser Arg Asp Asn Ala Lys Lys Ser Leu Tyr Leu Gln Met Asn
    290                 295                 300

Ser Leu Arg Ala Glu Asp Thr Ala Leu Tyr Tyr Cys Ala Lys Asp Ile
305                 310                 315                 320

Gln Tyr Gly Asn Tyr Tyr Tyr Gly Met Asp Val Trp Gly Gln Gly Thr
                325                 330                 335

Thr Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Leu Leu Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala

```
                500                 505                 510
Lys Thr Lys Pro Arg Glu Glu Gln Tyr Asn Ser Thr Tyr Arg Val Val
            515                 520                 525

Ser Val Leu Thr Val Leu His Gln Asp Trp Leu Asn Gly Lys Glu Tyr
            530                 535                 540

Lys Cys Lys Val Ser Asn Lys Ala Leu Pro Ala Pro Ile Glu Lys Thr
545                 550                 555                 560

Ile Ser Lys Ala Lys Gly Gln Pro Arg Glu Pro Gln Val Tyr Thr Leu
            565                 570                 575

Pro Pro Ser Arg Glu Glu Met Thr Lys Asn Gln Val Ser Leu Thr Cys
            580                 585                 590

Leu Val Lys Gly Phe Tyr Pro Ser Asp Ile Ala Val Glu Trp Glu Ser
            595                 600                 605

Asn Gly Gln Pro Glu Asn Asn Tyr Lys Thr Thr Pro Pro Val Leu Asp
            610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
            645                 650                 655

Leu His Asn His Tyr Thr Gln Lys Ser Leu Ser Leu Ser Pro Gly Lys
            660                 665                 670

<210> SEQ ID NO 49
<211> LENGTH: 3
<212> TYPE: PRT
<213> ORGANISM: Artificial Sequence
<220> FEATURE:
<223> OTHER INFORMATION: peptide linker sequence

<400> SEQUENCE: 49

Gly Gly Ser
1

<210> SEQ ID NO 50
<211> LENGTH: 3
<212> TYPE: PRT
<213> ORGANISM: Artificial Sequence
<220> FEATURE:
<223> OTHER INFORMATION: peptide linker sequence

<400> SEQUENCE: 50

Ser Gly Gly
1

<210> SEQ ID NO 51
<211> LENGTH: 3
<212> TYPE: PRT
<213> ORGANISM: Artificial Sequence
<220> FEATURE:
<223> OTHER INFORMATION: peptide linker sequence

<400> SEQUENCE: 51

Gly Gly Gly
1

<210> SEQ ID NO 52
<211> LENGTH: 4
<212> TYPE: PRT
<213> ORGANISM: Artificial Sequence
<220> FEATURE:
<223> OTHER INFORMATION: peptide linker sequence
```

```
<400> SEQUENCE: 52

Gly Gly Gly Ser
1

<210> SEQ ID NO 53
<211> LENGTH: 4
<212> TYPE: PRT
<213> ORGANISM: Artificial Sequence
<220> FEATURE:
<223> OTHER INFORMATION: peptide linker sequence

<400> SEQUENCE: 53

Ser Gly Gly Gly
1

<210> SEQ ID NO 54
<211> LENGTH: 5
<212> TYPE: PRT
<213> ORGANISM: Artificial Sequence
<220> FEATURE:
<223> OTHER INFORMATION: peptide linker sequence

<400> SEQUENCE: 54

Gly Gly Gly Gly Ser
1               5

<210> SEQ ID NO 55
<211> LENGTH: 8
<212> TYPE: PRT
<213> ORGANISM: Artificial Sequence
<220> FEATURE:
<223> OTHER INFORMATION: peptide linker sequence

<400> SEQUENCE: 55

Gly Gly Gly Gly Ser Gly Gly Ser
1               5

<210> SEQ ID NO 56
<211> LENGTH: 10
<212> TYPE: PRT
<213> ORGANISM: Artificial Sequence
<220> FEATURE:
<223> OTHER INFORMATION: peptide linker sequence

<400> SEQUENCE: 56

Gly Gly Gly Gly Ser Gly Gly Gly Gly Ser
1               5                   10

<210> SEQ ID NO 57
<211> LENGTH: 15
<212> TYPE: PRT
<213> ORGANISM: Artificial Sequence
<220> FEATURE:
<223> OTHER INFORMATION: peptide linker sequence

<400> SEQUENCE: 57

Gly Gly Gly Gly Ser Gly Gly Gly Gly Ser Gly Gly Gly Gly Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: peptide linker sequence

<400> SEQUENCE: 58
```

Ala Lys Thr Thr Pro Lys Leu Glu Glu Gly Glu Phe Ser Glu Ala Arg
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: peptide linker sequence

<400> SEQUENCE: 59

Ala Lys Thr Thr Pro Lys Leu Glu Glu Gly Glu Phe Ser Glu Ala Arg
1               5                   10                  15

Val

<210> SEQ ID NO 60
<211> LENGTH: 9
<212> TYPE: PRT
<213> ORGANISM: Artificial Sequence
<220> FEATURE:
<223> OTHER INFORMATION: peptide linker sequence

<400> SEQUENCE: 60

Ala Lys Thr Thr Pro Lys Leu Gly Gly
1               5

<210> SEQ ID NO 61
<211> LENGTH: 10
<212> TYPE: PRT
<213> ORGANISM: Artificial Sequence
<220> FEATURE:
<223> OTHER INFORMATION: peptide linker sequence

<400> SEQUENCE: 61

Ser Ala Lys Thr Thr Pro Lys Leu Gly Gly
1               5                   10

<210> SEQ ID NO 62
<211> LENGTH: 16
<212> TYPE: PRT
<213> ORGANISM: Artificial Sequence
<220> FEATURE:
<223> OTHER INFORMATION: peptide linker sequence

<400> SEQUENCE: 62

Lys Thr Thr Pro Lys Leu Glu Glu Gly Glu Phe Ser Glu Ala Arg Val
1               5                   10                  15

<210> SEQ ID NO 63
<211> LENGTH: 6
<212> TYPE: PRT
<213> ORGANISM: Artificial Sequence
<220> FEATURE:
<223> OTHER INFORMATION: peptide linker sequence

<400> SEQUENCE: 63

Ser Ala Lys Thr Thr Pro
1               5

<210> SEQ ID NO 64
<211> LENGTH: 10
<212> TYPE: PRT
<213> ORGANISM: Artificial Sequence
<220> FEATURE:
<223> OTHER INFORMATION: peptide linker sequence

```
<400> SEQUENCE: 64

Ser Ala Lys Thr Thr Pro Lys Leu Gly Gly
1               5                   10

<210> SEQ ID NO 65
<211> LENGTH: 6
<212> TYPE: PRT
<213> ORGANISM: Artificial Sequence
<220> FEATURE:
<223> OTHER INFORMATION: peptide linker sequence

<400> SEQUENCE: 65

Arg Ala Asp Ala Ala Pro
1               5

<210> SEQ ID NO 66
<211> LENGTH: 9
<212> TYPE: PRT
<213> ORGANISM: Artificial Sequence
<220> FEATURE:
<223> OTHER INFORMATION: peptide linker sequence

<400> SEQUENCE: 66

Arg Ala Asp Ala Ala Pro Thr Val Ser
1               5

<210> SEQ ID NO 67
<211> LENGTH: 12
<212> TYPE: PRT
<213> ORGANISM: Artificial Sequence
<220> FEATURE:
<223> OTHER INFORMATION: peptide linker sequence

<400> SEQUENCE: 67

Arg Ala Asp Ala Ala Ala Ala Gly Gly Pro Gly Ser
1               5                   10

<210> SEQ ID NO 68
<211> LENGTH: 27
<212> TYPE: PRT
<213> ORGANISM: Artificial Sequence
<220> FEATURE:
<223> OTHER INFORMATION: peptide linker sequence

<400> SEQUENCE: 68

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 69
<211> LENGTH: 6
<212> TYPE: PRT
<213> ORGANISM: Artificial Sequence
<220> FEATURE:
<223> OTHER INFORMATION: peptide linker sequence

<400> SEQUENCE: 69

Ser Ala Lys Thr Thr Pro
1               5

<210> SEQ ID NO 70
<211> LENGTH: 10
<212> TYPE: PRT
<213> ORGANISM: Artificial Sequence
<220> FEATURE:
```

```
<223> OTHER INFORMATION: peptide linker sequence

<400> SEQUENCE: 70

Ser Ala Lys Thr Thr Pro Lys Leu Gly Gly
1               5                   10

<210> SEQ ID NO 71
<211> LENGTH: 18
<212> TYPE: PRT
<213> ORGANISM: Artificial Sequence
<220> FEATURE:
<223> OTHER INFORMATION: peptide linker sequence

<400> SEQUENCE: 71

Ser Ala Lys Thr Thr Pro Lys Leu Glu Glu Gly Glu Phe Ser Glu Ala
1               5                   10                  15

Arg Val

<210> SEQ ID NO 72
<211> LENGTH: 5
<212> TYPE: PRT
<213> ORGANISM: Artificial Sequence
<220> FEATURE:
<223> OTHER INFORMATION: peptide linker sequence

<400> SEQUENCE: 72

Ala Asp Ala Ala Pro
1               5

<210> SEQ ID NO 73
<211> LENGTH: 12
<212> TYPE: PRT
<213> ORGANISM: Artificial Sequence
<220> FEATURE:
<223> OTHER INFORMATION: peptide linker sequence

<400> SEQUENCE: 73

Ala Asp Ala Ala Pro Thr Val Ser Ile Phe Pro Pro
1               5                   10

<210> SEQ ID NO 74
<211> LENGTH: 5
<212> TYPE: PRT
<213> ORGANISM: Artificial Sequence
<220> FEATURE:
<223> OTHER INFORMATION: peptide linker sequence

<400> SEQUENCE: 74

Thr Val Ala Ala Pro
1               5

<210> SEQ ID NO 75
<211> LENGTH: 12
<212> TYPE: PRT
<213> ORGANISM: Artificial Sequence
<220> FEATURE:
<223> OTHER INFORMATION: peptide linker sequence

<400> SEQUENCE: 75

Thr Val Ala Ala Pro Ser Val Phe Ile Phe Pro Pro
1               5                   10

<210> SEQ ID NO 76
<211> LENGTH: 6
<212> TYPE: PRT
<213> ORGANISM: Artificial Sequence
```

```
<220> FEATURE:
<223> OTHER INFORMATION: peptide linker sequence

<400> SEQUENCE: 76

Gln Pro Lys Ala Ala Pro
1               5

<210> SEQ ID NO 77
<211> LENGTH: 13
<212> TYPE: PRT
<213> ORGANISM: Artificial Sequence
<220> FEATURE:
<223> OTHER INFORMATION: peptide linker sequence

<400> SEQUENCE: 77

Gln Pro Lys Ala Ala Pro Ser Val Thr Leu Phe Pro Pro
1               5                   10

<210> SEQ ID NO 78
<211> LENGTH: 6
<212> TYPE: PRT
<213> ORGANISM: Artificial Sequence
<220> FEATURE:
<223> OTHER INFORMATION: peptide linker sequence

<400> SEQUENCE: 78

Ala Lys Thr Thr Pro Pro
1               5

<210> SEQ ID NO 79
<211> LENGTH: 13
<212> TYPE: PRT
<213> ORGANISM: Artificial Sequence
<220> FEATURE:
<223> OTHER INFORMATION: peptide linker sequence

<400> SEQUENCE: 79

Ala Lys Thr Thr Pro Pro Ser Val Thr Pro Leu Ala Pro
1               5                   10

<210> SEQ ID NO 80
<211> LENGTH: 6
<212> TYPE: PRT
<213> ORGANISM: Artificial Sequence
<220> FEATURE:
<223> OTHER INFORMATION: peptide linker sequence

<400> SEQUENCE: 80

Ala Lys Thr Thr Ala Pro
1               5

<210> SEQ ID NO 81
<211> LENGTH: 13
<212> TYPE: PRT
<213> ORGANISM: Artificial Sequence
<220> FEATURE:
<223> OTHER INFORMATION: peptide linker sequence

<400> SEQUENCE: 81

Ala Lys Thr Thr Ala Pro Ser Val Tyr Pro Leu Ala Pro
1               5                   10

<210> SEQ ID NO 82
<211> LENGTH: 6
<212> TYPE: PRT
<213> ORGANISM: Artificial Sequence
<220> FEATURE:
```

```
<223> OTHER INFORMATION: peptide linker sequence

<400> SEQUENCE: 82

Ala Ser Thr Lys Gly Pro
1               5

<210> SEQ ID NO 83
<211> LENGTH: 13
<212> TYPE: PRT
<213> ORGANISM: Artificial Sequence
<220> FEATURE:
<223> OTHER INFORMATION: peptide linker sequence

<400> SEQUENCE: 83

Ala Ser Thr Lys Gly Pro Ser Val Phe Pro Leu Ala Pro
1               5                   10

<210> SEQ ID NO 84
<211> LENGTH: 15
<212> TYPE: PRT
<213> ORGANISM: Artificial Sequence
<220> FEATURE:
<223> OTHER INFORMATION: peptide linker sequence

<400> SEQUENCE: 84

Gly Glu Asn Lys Val Glu Tyr Ala Pro Ala Leu Met Ala Leu Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: peptide linker sequence

<400> SEQUENCE: 85

Gly Pro Ala Lys Glu Leu Thr Pro Leu Lys Glu Ala Lys Val Ser
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: peptide linker sequence

<400> SEQUENCE: 86

Gly His Glu Ala Ala Ala Val Met Gln Val Gln Tyr Pro Ala Ser
1               5                   10                  15

<210> SEQ ID NO 87
<211> LENGTH: 664
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
```

-continued

```
               50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Pro
                     85                  90                  95
Phe Thr Phe Gly Pro Gly Thr Lys Val Asp Ile Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
                130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
                195                 200                 205
Ser Phe Asn Arg Gly Glu Cys Gln Val Gln Leu Val Gln Ser Gly Ala
210                 215                 220
Glu Val Lys Lys Pro Gly Ser Ser Val Lys Val Ser Cys Lys Ala Ser
225                 230                 235                 240
Gly Tyr Ser Phe Thr Asp Tyr His Ile His Trp Val Arg Gln Ala Pro
                245                 250                 255
Gly Gln Gly Leu Glu Trp Met Gly Val Ile Asn Pro Met Tyr Gly Thr
                260                 265                 270
Thr Asp Tyr Asn Gln Arg Phe Lys Gly Arg Val Thr Ile Thr Ala Asp
                275                 280                 285
Glu Ser Thr Ser Thr Ala Tyr Met Glu Leu Ser Ser Leu Arg Ser Glu
                290                 295                 300
Asp Thr Ala Val Tyr Tyr Cys Ala Arg Tyr Asp Tyr Phe Thr Gly Thr
305                 310                 315                 320
Gly Val Tyr Trp Gly Gln Gly Thr Leu Val Thr Val Ser Ser Ala Ser
                325                 330                 335
Thr Lys Gly Pro Ser Val Phe Pro Leu Ala Pro Ser Ser Lys Ser Thr
                340                 345                 350
Ser Gly Gly Thr Ala Ala Leu Gly Cys Leu Val Lys Asp Tyr Phe Pro
                355                 360                 365
Glu Pro Val Thr Val Ser Trp Asn Ser Gly Ala Leu Thr Ser Gly Val
                370                 375                 380
His Thr Phe Pro Ala Val Leu Gln Ser Ser Gly Leu Tyr Ser Leu Ser
385                 390                 395                 400
Ser Val Val Thr Val Pro Ser Ser Ser Leu Gly Thr Gln Thr Tyr Ile
                405                 410                 415
Cys Asn Val Asn His Lys Pro Ser Asn Thr Lys Val Asp Lys Lys Val
                420                 425                 430
Glu Pro Lys Ser Cys Asp Lys Thr His Thr Cys Pro Pro Cys Pro Ala
                435                 440                 445
Pro Glu Leu Leu Gly Gly Pro Ser Val Phe Leu Phe Pro Pro Lys Pro
                450                 455                 460
Lys Asp Thr Leu Met Ile Ser Arg Thr Pro Glu Val Thr Cys Val Val
465                 470                 475                 480
```

```
Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
            530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Leu Ser Pro Gly Lys
            660

<210> SEQ ID NO 88
<211> LENGTH: 108
<212> TYPE: PRT
<213> ORGANISM: Homo sapiens

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys
            100                 105

<210> SEQ ID NO 89
<211> LENGTH: 229
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 89

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys
225

<210> SEQ ID NO 90
<211> LENGTH: 126
<212> TYPE: PRT
<213> ORGANISM: Homo sapiens

<400> SEQUENCE: 90

Gln Val Gln Leu Val Glu Ser Gly Gly Val Val Gln Pro Gly Arg
1                5                  10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
            115                 120                 125

<210> SEQ ID NO 91
<211> LENGTH: 219
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 91

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 92
<211> LENGTH: 658
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser

```
            115                 120                 125
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys Gln Val Gln Leu Val Glu Ser Gly Gly
210                 215                 220

Gly Val Val Gln Pro Gly Arg Ser Leu Arg Leu Asp Cys Lys Ala Ser
225                 230                 235                 240

Gly Ile Thr Phe Ser Asn Ser Gly Met His Trp Val Arg Gln Ala Pro
                245                 250                 255

Gly Lys Gly Leu Glu Trp Val Ala Val Ile Trp Tyr Asp Gly Ser Lys
                260                 265                 270

Arg Tyr Tyr Ala Asp Ser Val Lys Gly Arg Phe Thr Ile Ser Arg Asp
            275                 280                 285

Asn Ser Lys Asn Thr Leu Phe Leu Gln Met Asn Ser Leu Arg Ala Glu
290                 295                 300

Asp Thr Ala Val Tyr Tyr Cys Ala Thr Asn Asp Asp Tyr Trp Gly Gln
305                 310                 315                 320

Gly Thr Leu Val Thr Val Ser Ala Ser Thr Lys Gly Pro Ser Val
                325                 330                 335

Phe Pro Leu Ala Pro Ser Ser Lys Ser Thr Ser Gly Gly Thr Ala Ala
                340                 345                 350

Leu Gly Cys Leu Val Lys Asp Tyr Phe Pro Glu Pro Val Thr Val Ser
            355                 360                 365

Trp Asn Ser Gly Ala Leu Thr Ser Gly Val His Thr Phe Pro Ala Val
370                 375                 380

Leu Gln Ser Ser Gly Leu Tyr Ser Leu Ser Ser Val Val Thr Val Pro
385                 390                 395                 400

Ser Ser Ser Leu Gly Thr Gln Thr Tyr Ile Cys Asn Val Asn His Lys
                405                 410                 415

Pro Ser Asn Thr Lys Val Asp Lys Lys Val Glu Pro Lys Ser Cys Asp
                420                 425                 430

Lys Thr His Thr Cys Pro Pro Cys Pro Ala Pro Glu Leu Leu Gly Gly
            435                 440                 445

Pro Ser Val Phe Leu Phe Pro Pro Lys Pro Lys Asp Thr Leu Met Ile
            450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
                485                 490                 495

Asn Ala Lys Thr Lys Pro Arg Glu Glu Gln Tyr Asn Ser Thr Tyr Arg
                500                 505                 510

Val Val Ser Val Leu Thr Val Leu His Gln Asp Trp Leu Asn Gly Lys
            515                 520                 525

Glu Tyr Lys Cys Lys Val Ser Asn Lys Ala Leu Pro Ala Pro Ile Glu
530                 535                 540
```

-continued

Lys Thr Ile Ser Lys Ala Lys Gly Gln Pro Arg Glu Pro Gln Val Tyr
545                 550                 555                 560

Thr Leu Pro Pro Ser Arg Glu Glu Met Thr Lys Asn Gln Val Ser Leu
            565                 570                 575

Thr Cys Leu Val Lys Gly Phe Tyr Pro Ser Asp Ile Ala Val Glu Trp
            580                 585                 590

Glu Ser Asn Gly Gln Pro Glu Asn Asn Tyr Lys Thr Thr Pro Pro Val
            595                 600                 605

Leu Asp Ser Asp Gly Ser Phe Phe Leu Tyr Ser Lys Leu Thr Val Asp
            610                 615                 620

Lys Ser Arg Trp Gln Gln Gly Asn Val Phe Ser Cys Ser Val Met His
625                 630                 635                 640

Glu Ala Leu His Asn His Tyr Thr Gln Lys Ser Leu Ser Leu Ser Pro
            645                 650                 655

Gly Lys

<210> SEQ ID NO 93
<211> LENGTH: 108
<212> TYPE: PRT
<213> ORGANISM: Homo sapiens

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 94
<211> LENGTH: 113
<212> TYPE: PRT
<213> ORGANISM: Homo sapiens

<400> SEQUENCE: 94

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
            50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

```
Ala Thr Asn Asp Asp Tyr Trp Gly Gln Gly Thr Leu Val Thr Val Ser
                100                 105                 110
Ser

<210> SEQ ID NO 95
<211> LENGTH: 221
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 96
<211> LENGTH: 118
<212> TYPE: PRT
<213> ORGANISM: Homo sapiens

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Ile Tyr Tyr Cys
            85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 97
<211> LENGTH: 214
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 107
<212> TYPE: PRT
<213> ORGANISM: Homo sapiens

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

-continued

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                      80

Glu Asp Phe Ala Val Tyr Tyr Cys Gln Gln Ser Ser Asn Trp Pro Arg
                85              90                  95

Thr Phe Gly Gln Gly Thr Lys Val Glu Ile Lys
            100             105
```